US011597775B2

(12) United States Patent
Loibner et al.

(10) Patent No.: US 11,597,775 B2
(45) Date of Patent: *Mar. 7, 2023

(54) PREPARATIONS AND METHODS FOR TREATING A GD2 POSITIVE CANCER

(71) Applicant: APEIRON BIOLOGICS AG, Vienna (AT)

(72) Inventors: Hans Loibner, Vienna (AT); Oliver Mutschlechner, Wiener Neudorf (AT); Ruth Ladenstein, Vienna (AT); Isabel Klier, Vienna (AT)

(73) Assignee: APEIRON BIOLOGICS AG, Vienna (AT)

(*) Notice: Subject to any disclaimer, the term of this patent is extended or adjusted under 35 U.S.C. 154(b) by 674 days.

This patent is subject to a terminal disclaimer.

(21) Appl. No.: 15/824,055

(22) Filed: Nov. 28, 2017

(65) Prior Publication Data

US 2018/0258183 A1 Sep. 13, 2018

Related U.S. Application Data

(63) Continuation of application No. 15/036,519, filed as application No. PCT/EP2014/075315 on Nov. 21, 2014, now Pat. No. 9,840,566, which is a continuation-in-part of application No. 14/182,776, filed on Feb. 18, 2014, now Pat. No. 10,294,305, and a continuation-in-part of application No. 14/086,696, filed on Nov. 21, 2013, now abandoned.

(30) Foreign Application Priority Data

Nov. 21, 2013 (CA) ................................ CA 2834000
Nov. 21, 2013 (EP) ..................................... 13193953

(51) Int. Cl.
*C07K 16/30* (2006.01)
*A61K 9/00* (2006.01)
*A61K 39/00* (2006.01)

(52) U.S. Cl.
CPC ........ *C07K 16/3084* (2013.01); *A61K 9/0019* (2013.01); *A61K 2039/505* (2013.01); *A61K 2039/545* (2013.01); *C07K 2317/24* (2013.01); *C07K 2317/734* (2013.01)

(58) Field of Classification Search
CPC .......... C07K 16/3084; A61K 2039/505; A61K 2039/545
See application file for complete search history.

(56) References Cited

U.S. PATENT DOCUMENTS

| 4,863,713 A * | 9/1989 | Goodwin ........... A61K 51/1093 424/1.57 |
| 7,833,525 B2 | 11/2010 | Shenoy et al. |
| 9,777,068 B2 | 10/2017 | Loibner et al. |
| 9,840,566 B2 | 12/2017 | Loibner et al. |
| 10,294,305 B2 | 5/2019 | Loibner et al. |
| 2004/0131610 A1* | 7/2004 | Thorpe ................. C07K 16/44 424/141.1 |
| 2012/0058978 A1 | 3/2012 | Stein et al. |
| 2012/0328524 A1 | 12/2012 | Nicolaides et al. |
| 2014/0170155 A1 | 6/2014 | Loibner et al. |
| 2015/0139942 A1 | 5/2015 | Loibner et al. |
| 2016/0304620 A1 | 10/2016 | Loibner et al. |
| 2018/0134801 A1 | 5/2018 | Loibner et al. |
| 2018/0258183 A1 | 9/2018 | Loibner et al. |
| 2020/0332021 A1 | 10/2020 | Loibner et al. |
| 2021/0221909 A1 | 7/2021 | Loibner et al. |

FOREIGN PATENT DOCUMENTS

| JP | 2006521085 | 9/2006 | |
| JP | 6693873 B | 5/2020 | |
| NZ | 701628 | 11/2014 | |
| WO | WO 2005/070967 | 8/2005 | |
| WO | WO-2007045465 A1 * | 4/2007 | ........... C07K 14/005 |
| WO | WO 2008/049643 | 5/2008 | |
| WO | WO 2011/160119 | 12/2011 | |
| WO | WO 2013/060867 | 5/2013 | |
| WO | WO 2013/189516 | 12/2013 | |
| WO | WO 2013/189554 | 12/2013 | |

OTHER PUBLICATIONS

Cheung et al. (International Journal of Oncology, 1998, vol. 12, pp. 1299-1306) (Year: 1998).*
Clinical Trials.Gov (Accession No. NCT01704716, version 1, Oct. 10, 2012) (Year: 2012).*
Seeger (Seminars in Cancer Biology, 2011, vol. 21, pp. 229-237) (Year: 2011).*
"High Risk Neuroblastoma Study 1 of SIOP-EUROPE (SIOPEN)", SIOP, Jul. 1, 2009, pp. 1-303, Retrieved from the Internet: URL:http://www.oncauvergne.fr/index.php?option=com_docman&task=doc_download&gid=928&Itemid= [retrieved on Mar. 27, 2014].
"Press Release: Oncology Alliance. Apeiron, CCRI and SIOPEN Join Forces against Neuroblastoma", Apeiron Biologies AG., Jun. 2011, 8 pages. Vienna. Retrieved from the internet: URL:http://www.life-sciences-germany.com/news/apeiron-ccri-siopen-neuroblastoma-biologics-group-forschungs-und-2001-97329.html [retrieved on Mar. 20, 2014].

(Continued)

*Primary Examiner* — Karen A. Canella
(74) *Attorney, Agent, or Firm* — Norton Rose Fulbright US LLP

(57) ABSTRACT

The present invention relates to preparations and methods for treating a GD2 positive cancer by administering a preparation comprising a chimeric or humanized anti-GD2 antibody to a patient, wherein the patient is not concomitantly treated with Interleukin-2 (IL-2 wherein a GD2 positive cancer is treated in the patient. Furthermore, the invention relates to preparations and methods for the treatment of a GD2 positive cancer in a patient, wherein a preparation comprising an anti-GD2 antibody is administered to the patient as a continuous infusion, without concomitantly administering IL-2. The present invention further relates to preparations and methods for the treatment of a GD2 positive cancer in a patient, wherein the one or more anti-GD2 antibody treatment periods is/are preceded, accompanied, and/or followed by one or more treatment periods with a retinoid.

14 Claims, 17 Drawing Sheets

Specification includes a Sequence Listing.

(56) References Cited

OTHER PUBLICATIONS

Aperion Biologics Website, "Managed Access Program," Jul. 26, 2017, pp. 1-3.
Balwierz et al., "Treatment results of children with neuroblastoma: report of Polish Pediatric Solid Tumor Group", Przegl Lek, 67: 387-92, 2010. (Abstract provided).
Batova et al., "The Ch14.18-GM-CSF fusion protein is effective at mediating antibody-dependent cellular cytotoxicity and complement-dependent cytotoxicity in vitro", Clin. Cancer Res., 5(12):4259-4263, 1999.
Beckman et al., "Antibody Constructs in Cancer Therapy", Cancer., 109(2): 170-179, 2007.
Castel et al., "Treatment of high-risk neuroblastoma with anti-GD2 antibodies", *Clinical and Translational Oncology*, 12(12): 788-793, 2010.
Cespdes et al., "Mouse models in oncogenesis and cancer therapy", Clin Transl Oncol., 8(5): 318-329, 2006.
Chames and Baty, "Bispecific antibodies for cancer therapy: the light at the end of the tunnel?", MAbs, 1(6):539-547, 2009.
Cheung et al., "Humanizing murine IgG3 anti-GD2 antibody m3F8 substantially improves antibody-dependent cell-mediated cytotoxicity while retaining targeting in vivo," *OncoImmunology*, 1:477-486, (2012).
Coping with Ch14.18, Children's Neuroblastoma Cancer Foundation, Revised Jul. 31, 2012 www.cncfhope.org.
Dennis, "Off by a whisker", Nature, 442: 739-741, 2006.
Drozynska et al., "Initial results of the treatment of six patients with high risk neuroblastoma in the years 2002-2006", Med Wieku Rozwoj, 11(3 pt 2): 325-30, 2011. (Abstract provided).
Frost et al., "A phase I/IB trial of murine monoclonal anti-GD2 antibody 14.G2a plus interleukin-2 in children with refractory neuroblastoma: a report of the Children's Cancer Group", Cancer, 80(2):317-333, 1997.
Fujimori et al., "A Modeling Analysis of Monoclonal Antibody Percolation Through Tumors: A Binding-Site Barrier", J Nuc Med., 31: 1191-1198, 1990.
Gains et al., "Ten challenges in the management of neuroblastoma", *Future Oncology*, 8(7): 839-858, 2012.
Gilman, A.L. et al: "Phase I Study of ch14.18 With Granulocyte-Macrophage Colony-Stimulating Factor and Interleukin-2 in Children With Neuroblastoma After Autologous Bone Marrow Transplantation or Stem-Cell Rescue: A Report From the Children's Oncology Group", Journal of Clinical Oncology, vol. 27, No. 1, (Nov. 24, 2008), pp. 85-91.
Handgretinger et al., "A phase I study of human/mouse chimeric antiganglioside GD2 antibody ch14.18 inpatients with neuroblastoma", Eur. J. Cancer, 31A(2):261-267, 1995.
Handgretinger, Rupert et al: "A phase I study of neuroblastoma with the anti-ganglioside GD2 antibody 14.G2a", Cancer Immunology and Immunotherapy, Springerverlag, Berlin, DE, vol. 35, No. 3, Jan. 1, 1992 (Jan. 1, 1992), pp. 199-204.
Idusogie et al., "Mapping of the C1q binding site on rituxan, a chimeric antibody with a human IgG1 Fc", J. Immunol., 164(8):4178-4184, 2000.
International Search Report issued in PCT Appl No. PCT/EP2012/061618, dated Jan. 7, 2013.
International Search Report issued in PCT Appl. No. PCT/EP2012/064970, dated Jan. 11, 2013.
Kowalczyk et al., "The GD2-specific 14G2a monoclonal antibody induce apoptosis and enhances cytotoxicity of chemotherapeautic drugs in IMR-32 human neuroblastoma cells", Cancer Letters, 281: 171-182, 2009.
Kushner et al., "Phase II trial of the anti-GD2 monoclonal antibody 3F8 and granulocyte-macrophage colony-stimulating factor for neuroblastoma", *Journal of Clinical Oncology*, 19(22): 4189-4194, 2001.
Ladenstein, et al., "Ch14.18 Antibody Produced in CHO Cells in Relapsed or Refractory Stage 4 Neuroblastoma Patients," *mAbs*, 5(5), 801-809, 2013.
Lode and Dobke, "A Phase I/II Dose Schedule Finding Study of ch14.18/CHO Continuous Infusion Combined with Subcutaneious Aldesleukin (=Proleukin) (IL-2) in Pateints with Primary refractory or Relapsed Neuroblastoma. A SIOPEN Study", 3 pages, 2012, <http://www.kinderkrebsinfo.de/health_professionals/clinical_trials/phase_i_ii_trials_in_the_gpoh/longterminfusion_study_lti_ch1418/index_eng.html>, retrieved Dec. 10, 2012.
Lode et al., "Long-term continuous infusion of anti-GD2 antibody CH14.18/CHO in relapsed/refractory neuroblastoma patients", *Journal for ImmunoTherapy of Cancer*, 1(Suppl 1): 244, 2013.
Mueller et al., "Enhancement of antibody-dependent cytotoxicity with a chimeric anti-GD2 antibody", J. Immunol., 144(4):1382-1386, 1990.
Mujoo et al., "Functional Properties and Effect on Growth Suppression of Human Neuroblastoma Tumors by Isotype Switch Variants of Monoclonal Antiganglioside GD2 Antibody 14.18", Cancer Res., 49: 2857-2861, 1989.
Murray et al., "Phase I trial of murine monoclonal antibody 14G2a administered by prolonged intravenous infusion in patients with neuroectodermal tumors", Journal of Clinical Oncology, 12(1):184-193, 1994.
Navid et al., "Anti-GD2 antibody therapy for GD2-expressing tumors", Curr. Cancer Drug Targets, 10(2):200-209, 2010.
NCT00072358, "Phase II Study of Anti-GD2 3F8 Antibody and GM-CSF for High Risk Neuroblastoma," *ClinicalTrials.gov archive*, version 2013-07-08.
Office Action issued in European Patent Application No. 13193953.0, dated Apr. 16, 2014.
Office Action issued in Japanese Patent Application No. 2015-517621, dated Jun. 28, 2016.
Ozkaynak, M. F.: "Phase I study of chimeric human/murine antiganglioside GD2 monoclonal antibody (ch14.18) with granulocyte-macrophage colony-stimulating factor in children with neuroblastoma immediately after hematopoietic stem-cell transplantation: A Children's Cancer Group study", Journal of Clinical Oncology, American Society of Clinical Oncology, US, vol. 18, No. 24, (Dec. 15, 2000), pp. 4077-4085.
Raffaghello et al., "Anti-GD2 monoclonal antibody immunotherapy: a promising strategy in the prevention of neuroblastoma relapse", Cancer Letters, 197: 205-209, 2003.
Rudnick et al., "Affinity and Avidity in Antibody-Based Tumor Targeting", Can Biotherp & Radiopharm., 24: 155-162, 2009.
Saleh et al., "Phase I trial of the murine monoclonal anti-GD2 antibody 14G2a in metastatic melanoma", Cancer Research, 52(16):4342-4347, 1992.
Shusterman et al., "Antitumor activity of hu14.18-IL2 in patients with relapsed/refractory neuroblastoma: a Children's Oncology Group (COG) phase II study", J Clin Oncol., 28(33):4969-4975, 2010.
Simon et al., "Long Term Outcome of High Risk Neuroblastoma Patients After Immunotherapy with Antibody CH14.18 or Oral Metronomic Chemotherapy," *BMC Cancer*, 11.21 (20122): 1-8.
Simon, "Consolidation Treatment With Chimeric Anti-GD2-Antibody ch14. 18 in Children Older than 1 Year With Metastatic Neuroblastoma", *Journal of Clinical Oncology*, 22(17): 3549-3557, 2004.
Talmadge et al., "Murine Medels to Evaluate Novel and Conventional Therapeutic Strategies for Cancer", Am J Pathol, 170(3): 793-804, 2007.
Thurber et al., "Antibody tumor penetration: Transport opposed by systemic and antigen-mediated clearance", Adv Drug Deliv Rev., 60: 1421-1434, 2008.
Voskoglou-Nomikos, "Clinical Predictive Value of the in Vitro Cell Line, Human Xenograft, and Mouse Allograft Preclinical Cancer Models1", Clin Can Res., 9: 4227-4239, 2003.
Vriesendorp et al., "Preclinical analysis of radiolabeled anti-GD2 immunoglobulin G", Cancer 18(12 Suppl): 2642-9, 1997.
Yu et al., "Anti-GD2 antibody with GM-CSF, interleukin-2, and isotretinoin for neuroblastoma", New England Journal of Medicine, 363(14):1324-1334, 2010.
Yu et al., "Phase I trial of a human-mouse chimeric anti-disialoganglioside monoclonal antibody ch14.18 in patients with

(56) References Cited

OTHER PUBLICATIONS refractory neuroblastoma and osteosarcoma", Journal of Clinical Oncology, 16(6):2169-2180, 1998.
Zeng et al., "Anti-neuroblastoma effect of ch14.18 antibody produced in CHO cells is mediated by NK-cells in mice", Molecular Immunology, 42(11):1311-1319, 2005.
Iida et al., "Two mechanisms of the enhanced antibody-dependent cellular cytotoxicity (ADCC) efficacy of non-fucosylated therapeutic antibodies in human blood." BMC Cancer, 9:58, 2009.
Longterminfusion Study (LTI). Jun. 13, 2012. Accessed online, URL: https://www.kinderkrebsinfo.de/health_professionals/clinical_trials/phase_i_ii_trials_in_ the_gpoh/longterminfusion_study_lti_ch1418/index.eng.html.
Official Notification from the Eurasian Patent Office issued in corresponding Application No. 201691055 dated Sep. 10, 2020.
Peipp et al., "Antibody fucosylation differently impacts cytotoxicity mediated by NK and PMN effector cells", Blood, 112(6): 2390-2399, 2008.
Search Report and Written Opinion from the Intellectual Property Office of Singapore issued in corresponding Patent Application No. 102016105320 dated Sep. 3, 2020.
Amrani et al., "Quantification of total dinutuximab concentrations in neuroblastoma patients with liquid chromatography tandem mass spectrometry", Anal Bioanal Chem, 410(23):5849-5858, 2018.
Dobrenkov and Cheung, "GD2-Targeted Immunotherapy and Radioimmunotherapy", Seminars in Oncology, 41(5):589-612, 2014. (Abstract Only).
Gillies et al, "High-level expression of chimeric antibodies using adapted cDNA variable region cassettes", Journal of Immunological Methods, 125(1-2):191-202, 1989. (Abstract Only).
Marachelian et al., "Comparative pharmacokinetics, safety, and tolerability of two sources of ch14.18 in pediatric patients with high-risk neuroblastoma following myeloablative therapy", Cancer Chemother Pharmacol, 77:405-412, 2016.
Mueller et al., "Tolerability, response and outcome of high-risk neuroblastoma patients treated with long-term infusion of anti-GD2 antibody ch14.18/CHO", MAbs, 10(1):55-61, 2018.
Mora, James; "Anti-GD2 mAbs for the treatment of high-risk neuroblastoma", Hospital Healthcare Europe, accessed online: <https://hospitalhealthcare.com/latest-issue-2018/anti-gd2-mabs-for-the-treatment-of-high-risk-neuroblastoma/>, Oct. 2018.
NCT00026312, "Isotretinoin With or Without Dinutuximab, Aldesleukin, and Sargramostim Following Stem Cell Transplant in Treating Patients With Neuroblastoma", ClinicalTrials.gov, v1, accessed online: <https://clinicaltrials.gov/ct2/show/study/NCT00026312>, Jun. 28, 2005.
Deng R. et al.: Monoclonal antibodies: what are the pharmacokinetic and pharmacodynamic considerations for drug development? Expert Opinion on Drug Metabolism & Toxicology, 2012. 8:2, 141-161, DOI 10.1517/17425255.2012.643868.

* cited by examiner

A
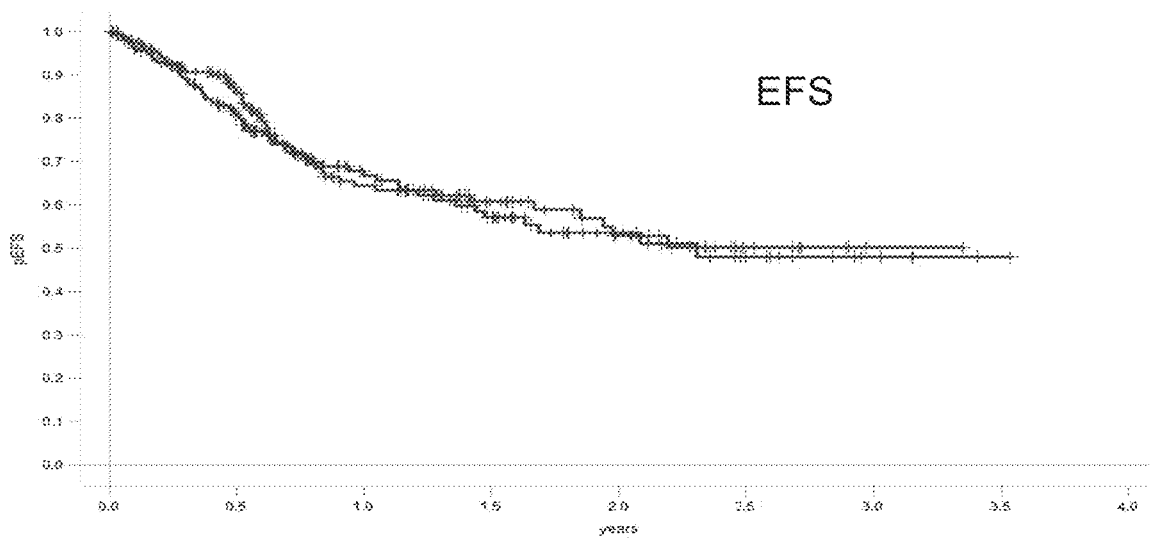
B
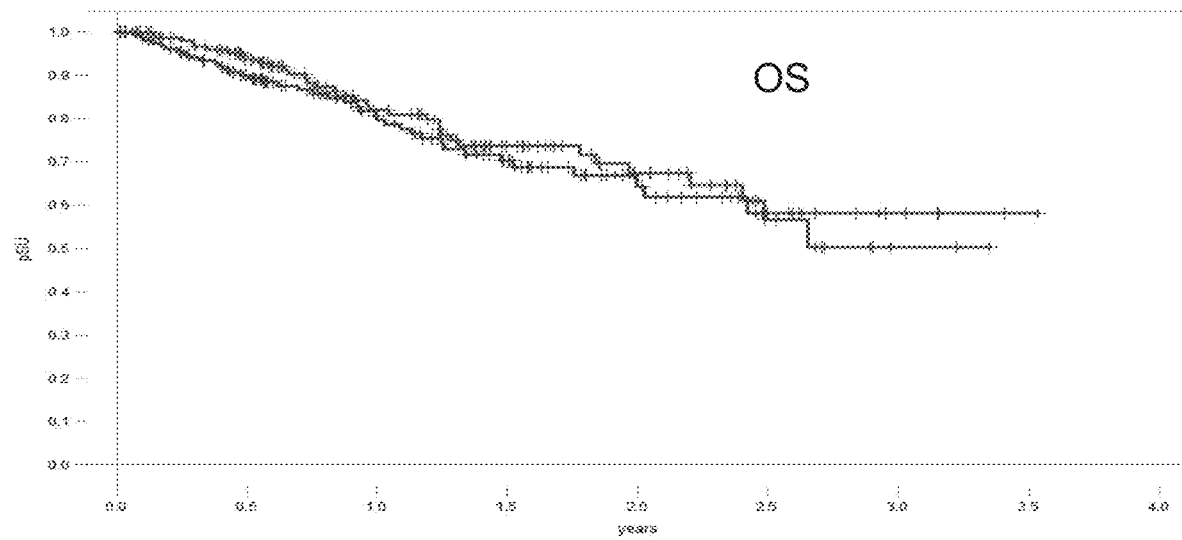
FIG. 1

A
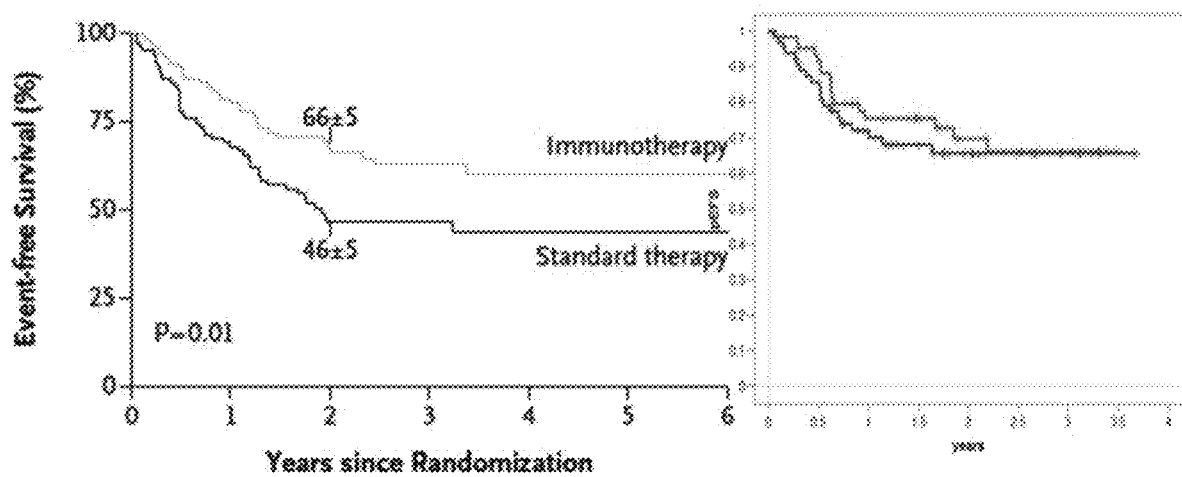
B
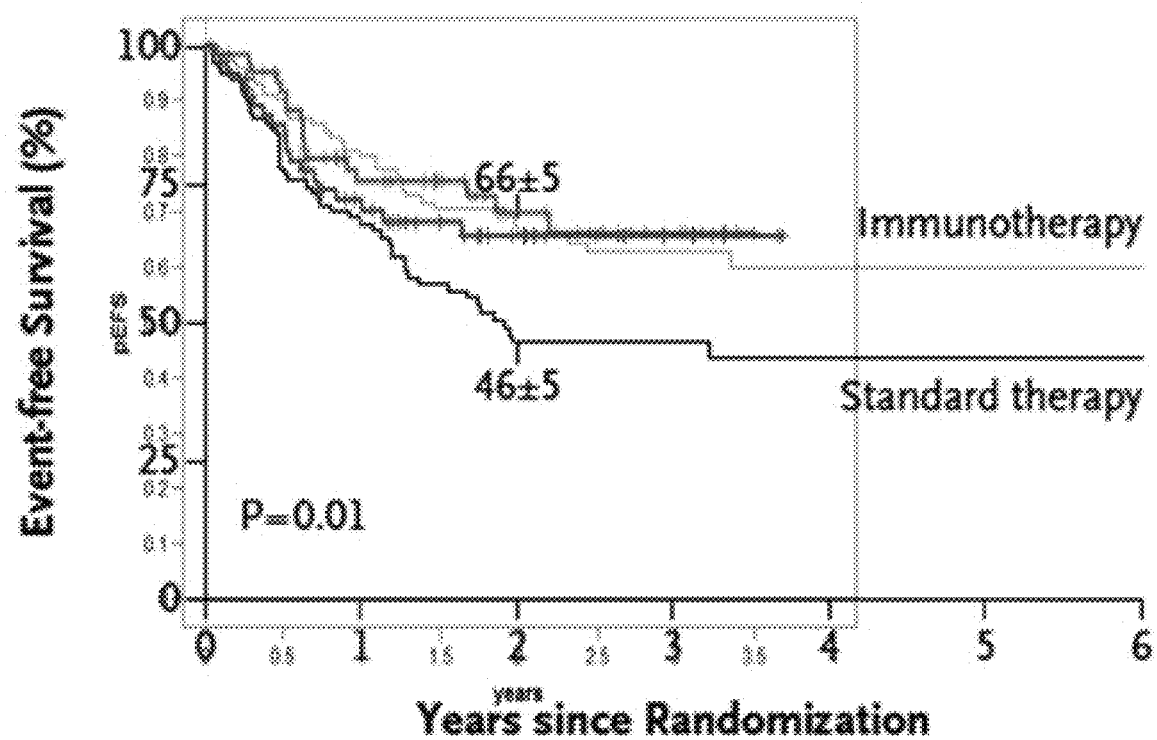
FIG. 2

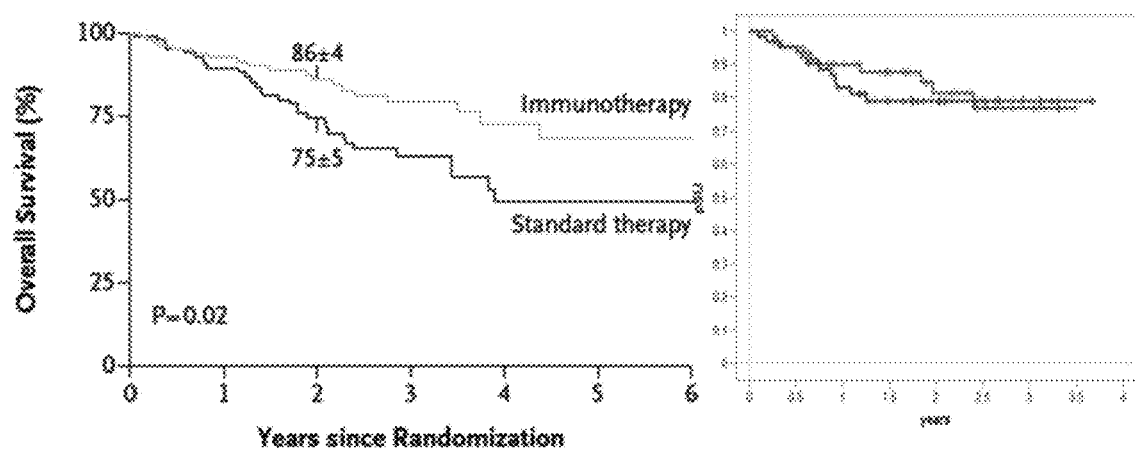
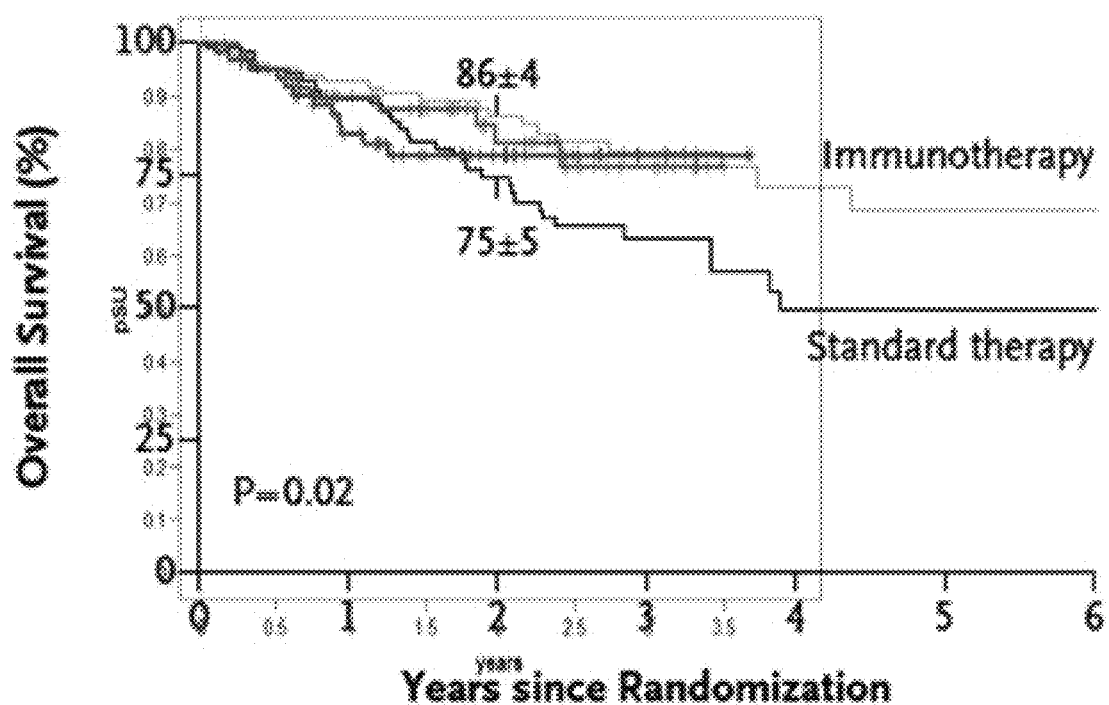
FIG. 3

| Toxicity | All Grades | | Grades 3-4 | |
|---|---|---|---|---|
| | % Patients ch14.18/CHO + 13-cis-RA | % Patients ch14.18/CHO + 13-cis-RA + IL2 | % Patients ch14.18/CHO + 13-cis-RA | % Patients ch14.18/CHO + 13-cis-RA + IL2 |
| Haemoglobin | 82% | 88% | 39% | 64% |
| WBC | 76% | 76% | 28% | 31% |
| General Condition | 72% | 83% | 18% | 40% |
| Fever | 72% | 79% | 14% | 37% |
| Granulocytes | 67% | 77% | 30% | 48% |
| Platelets | 63% | 79% | 33% | 59% |
| Skin | 59% | 72% | 5% | 9% |
| SGOT/SGPT | 55% | 60% | 14% | 19% |
| Infection | 52% | 61% | 25% | 30% |
| Allergy | 50% | 58% | 8% | 17% |
| Nausea/Vomiting | 48% | 66% | 4% | 8% |
| Diarrhoea | 45% | 63% | 5% | 20% |
| Constipation | 37% | 26% | 0% | 2% |
| Hypotension | 24% | 29% | 7% | 14% |
| Stomatitis | 15% | 22% | 2% | 2% |
| Hypertension | 12% | 5% | 4% | 0% |
| Creatinin | 10% | 16% | 1% | 1% |
| Haematuria | 10% | 10% | 0% | 0% |
| Glomular filtration rate | 7% | 6% | 2% | 0% |
| Central neuro | 7% | 16% | 2% | 6% |
| Bilirubin | 7% | 17% | 2% | 4% |
| Ototoxicities | 7% | 11% | 2% | 5% |
| Proteinuria | 7% | 6% | 0% | 0% |
| Periph. neuro | 7% | 13% | 1% | 2% |
| Pulmo. tox. | 4% | 17% | 2% | 3% |
| Cardiac function | 3% | 4% | 2% | 2% |
| Echo LV/SV | 2% | 5% | 2% | 1% |
| VOD | 1% | 3% | 0% | 0% |
| Haemor. cyst | 0% | 2% | 0% | 0% |

FIG. 4

| Toxicity | Cycle 1 | | Cycle 2 | | Cycle 3 | | Cycle 4 | | Cycle 5 | | Cycle 6 | |
|---|---|---|---|---|---|---|---|---|---|---|---|---|
| | ch14.18/CHO + 13-cis-RA + IL2 | ch14.18/CHO + 13-cis-RA | ch14.18/CHO + 13-cis-RA + IL2 | ch14.18/CHO + 13-cis-RA | ch14.18/CHO + 13-cis-RA + IL2 | ch14.18/CHO + 13-cis-RA | ch14.18/CHO + 13-cis-RA + IL2 | ch14.18/CHO + 13-cis-RA | ch14.18/CHO + 13-cis-RA + IL2 | ch14.18/CHO + 13-cis-RA | 13-cis-RA (ch14.18/CHO treatment arm) | 13-cis-RA (ch14.18/CHO + IL2 treatment arm) |
| Haemoglobin | 78% | 82% | 89% | 76% | 89% | 73% | 86% | 66% | 81% | 37% | 49% |
| WBC | 66% | 69% | 66% | 54% | 54% | 40% | 46% | 32% | 45% | 12% | 16% |
| General Condition | 67% | 83% | 55% | 46% | 72% | 44% | 62% | 40% | 62% | 18% | 31% |
| Fever | 65% | 77% | 56% | 43% | 72% | 39% | 69% | 34% | 67% | 9% | 12% |
| Granulocytes | 47% | 60% | 59% | 50% | 72% | 46% | 65% | 36% | 61% | 22% | 31% |
| Platelets | 57% | 73% | 46% | 27% | 63% | 20% | 57% | 18% | 61% | 15% | 19% |
| Skin | 47% | 60% | 35% | 33% | 49% | 35% | 37% | 28% | 49% | 13% | 23% |
| SGOT/SGPT | 43% | 48% | 39% | 37% | 58% | 36% | 49% | 32% | 54% | 18% | 31% |
| Infection | 35% | 44% | 33% | 21% | 33% | 21% | 27% | 21% | 32% | 13% | 18% |
| Allergy | 34% | 45% | 24% | 24% | 36% | 17% | 28% | 13% | 29% | 2% | 3% |
| Nausea/Vomiting | 34% | 49% | 25% | 15% | 42% | 15% | 29% | 13% | 31% | 6% | 7% |
| Diarrhoea | 28% | 50% | 24% | 16% | 32% | 12% | 27% | 12% | 30% | 8% | 4% |
| Constipation | 19% | 15% | 17% | 12% | 10% | 11% | 7% | 9% | 9% | 5% | 1% |
| Hypotension | 9% | 16% | 14% | 14% | 19% | 10% | 9% | 10% | 9% | 0% | 0% |
| Stomatitis | 8% | 12% | 7% | 6% | 10% | 4% | 7% | 1% | 9% | 1% | 2% |
| Hypertension | 9% | 4% | 6% | 3% | 2% | 3% | 2% | 3% | 3% | 1% | 1% |
| Creatinin | 6% | 6% | 2% | 2% | 15% | 5% | 10% | 5% | 10% | 4% | 4% |
| Haematuria | 7% | 3% | 4% | 3% | 4% | 3% | 3% | 2% | 7% | 1% | 0% |
| Glomerular filtration rate | 2% | 1% | 1% | 0% | 0% | 0% | 0% | 2% | 3% | 7% | 6% |
| Central neuro | 4% | 10% | 4% | 2% | 2% | 3% | 3% | 2% | 1% | 0% | 1% |
| Bilirubin | 4% | 9% | 2% | 3% | 7% | 3% | 6% | 0% | 5% | 0% | 1% |
| Ototoxicities | 3% | 0% | 3% | 0% | 9% | 3% | 0% | 2% | 3% | 5% | 13% |
| Proteinuria | 3% | 4% | 7% | 1% | 2% | 1% | 2% | 2% | 5% | 0% | 0% |
| Periph. neuro | 4% | 9% | 3% | 2% | 5% | 1% | 2% | 1% | 7% | 0% | 2% |
| Pulmo. tox. | 5% | 14% | 1% | 1% | 8% | 0% | 3% | 0% | 4% | 0% | 2% |
| Cardiac function | 2% | 3% | 0% | 2% | 1% | 0% | 0% | 0% | 0% | 0% | 0% |
| Echo LV/SV | 1% | 3% | 0% | 3% | 1% | 1% | 1% | 0% | 0% | 0% | 0% |
| VOD | 0% | 2% | 0% | 3% | 1% | 0% | 0% | 0% | 0% | 0% | 0% |
| Haemor. cyst | 0% | 2% | 0% | 0% | 0% | 0% | 0% | 0% | 0% | 0% | 0% |

% Patients

FIG. 5

A
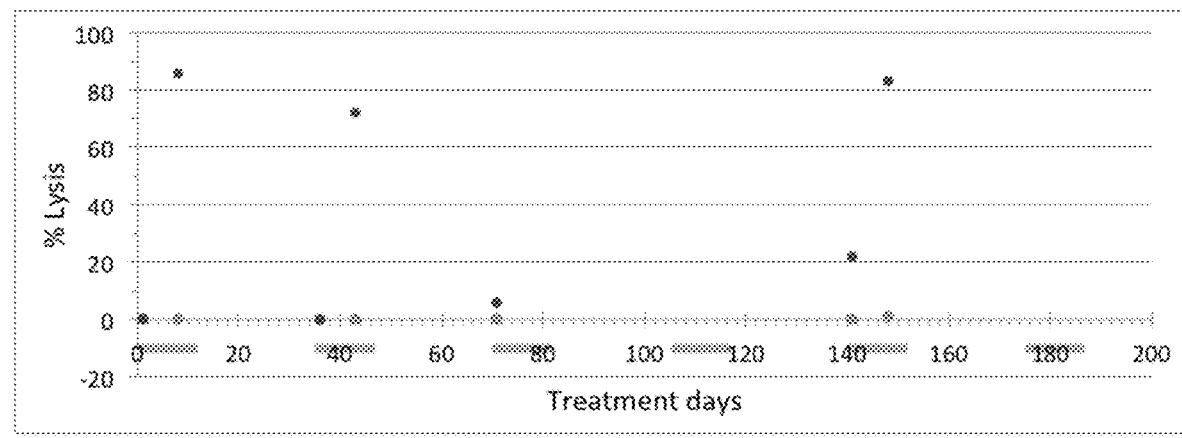
B
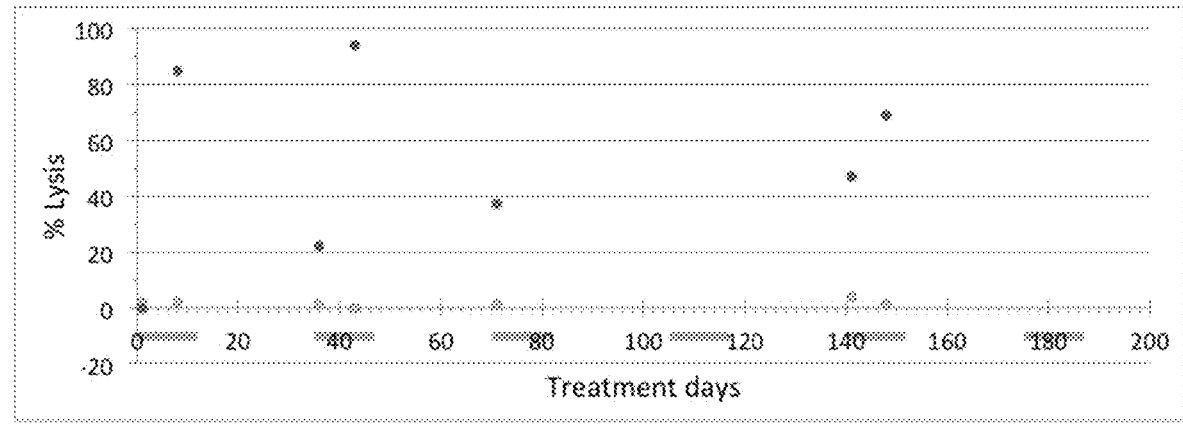
FIG. 16

A
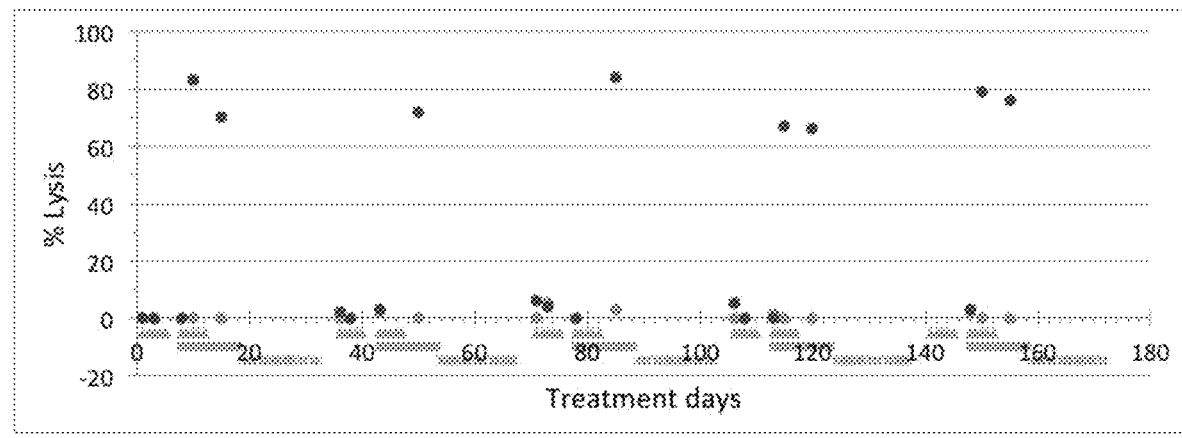
B
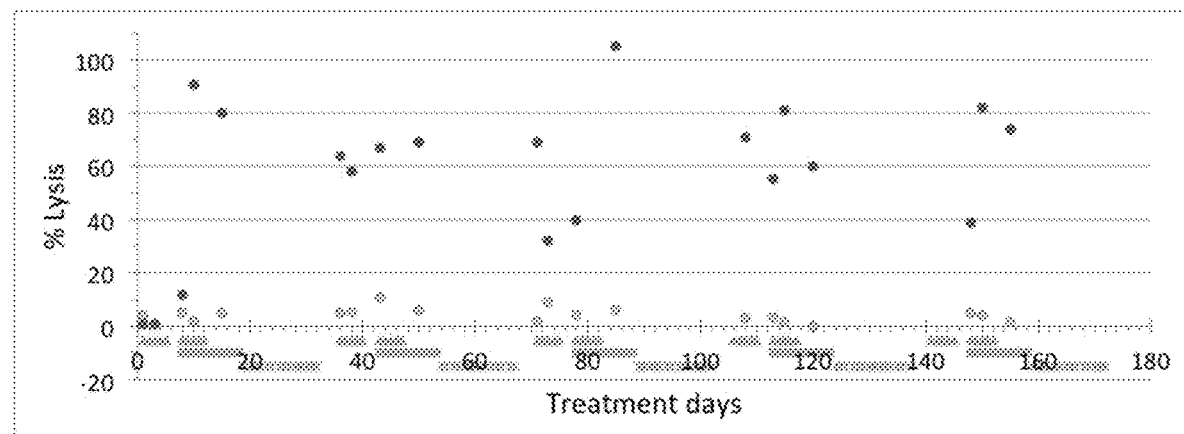
FIG. 17

SEQUENCE LISTING

```
<160> NUMBER OF SEQ ID NOS: 4

<210> SEQ ID NO 1
<211> LENGTH: 723
<212> TYPE: DNA
<213> ORGANISM: Artificial
<220> FEATURE:
<223> OTHER INFORMATION: monoclonal antibody chain

<400> SEQUENCE: 1
atggaagccc cagcgcagct tctcttcctc ctgctactct ggctcccaga taccactgga      60
gaaatagtga tgacgcagtc tccagccacc ctgtctgtgt ctccagggga aagagccacc     120
ctctcctgca gatctagtca gagtcttgta caccgtaatg gaaacaccta tttacattgg     180
tacctgcaga agccaggcca gtctccaaag ctcctgattc acaaagtttc caaccgattt     240
tctggggtcc cagacaggtt cagtggcagt ggatcaggga cagatttcac actcaagatc     300
agcagagtgg aggctgagga tctgggagtt tatttctgtt ctcaaagtac acatgttcct     360
ccgctcacgt tcggtgctgg gaccaagctg gagctgaaac gaactgtggc tgcaccatct     420
gtcttcatct tcccgccatc tgatgagcag ttgaaatctg gaactgcctc tgttgtgtgc     480
ctgctgaata acttctatcc cagagaggcc aaagtacagt ggaaggtgga taacgccctc     540
caatcgggta actcccagga gagtgtcaca gagcaggaca gcaaggacag cacctacagc     600
ctcagcagca ccctgacgct gagcaaagca gactacgaga aacacaaagt ctacgcctgc     660
gaagtcaccc atcagggcct gagctcgccc gtcacaaaga gcttcaacag gggagagtgt     720
tag                                                                   723

<210> SEQ ID NO 2
<211> LENGTH: 1389
<212> TYPE: DNA
<213> ORGANISM: Artificial
<220> FEATURE:
<223> OTHER INFORMATION: monoclonal antibody chain
```

<400> SEQUENCE: 2

```
atgggatgga cctggatctt tattttaatc ctgtcggtaa ctacaggtgt ccactctgag      60
gtccaactgc tgcagtctgg acctgagctg gagaagcctg gcgcttcagt gatgatatcc     120
tgcaaggctt ctggttcctc attcactggc tacaacatga actgggtgag cagaacatt     180
ggaaagagcc ttgaatggat tggagctatt gatccttact atggtggaac tagctacaac     240
cagaagttca gggcagggc acattgact gtagacaaat cgtccagcac agcctacatg       300
cacctcaaga gcctgacatc tgaggactct gcagtctatt actgtgtaag cggaatggag     360
tactggggtc aaggaaccct cagtcaccgt cctcagcct ccaccaaggg cccatcggtc      420
ttccccctgg caccctcctc aagagcacc tctgggggca gcggccct gggctgcctg        480
gtcaaggact acttccccga accggtgacg gtgtcgtgga actcaggcgc cctgaccagc     540
ggcgtgcaca ccttcccggc tgtcctacag tcctcaggac tctactccct cagcagcgtg     600
gtgaccgtgc cctccagcag cttgggcacc cagacctaca tctgcaacgt gaatcacaag     660
cccagcaaca ccaaggtgga caagagagtt gagcccaaat cttgtgacaa aactcacaca     720
tgcccaccgt gcccagcacc tgaactcctg gggggaccgt cagtcttcct cttcccccca     780
aaacccaagg acaccctcat gatctcccgg acccctgagg tcacatgcgt ggtggtggac     840
gtgagccacg aagaccctga ggtcaagttc aactggtacg tggacggcgt ggaggtgcat     900
aatgccaaga caaagccgcg ggaggagcag tacaacagca cgtaccgtgt ggtcagcgtc     960
ctcaccgtcc tgcaccagga ctggctgaat ggcaaggagt acaagtgcaa ggtctccaac    1020
aaagccctcc cagcccccat cgagaaaacc atctccaaag ccaaagggca gccccgagaa    1080
ccacaggtgt acaccctgcc cccatcccgg gaggagatga ccaagaacca ggtcagcctg    1140
acctgcctgg tcaaaggctt ctatcccagc gacatcgccg tggagtggga gagcaatggg    1200
cagccggaga acaactacaa gaccacgcct cccgtgctgg actccgacgg ctccttcttc    1260
ctctatagca agctcaccgt ggacaagagc aggtggcagc aggggaacgt cttctcatgc    1320
tccgtgatgc atgaggctct gcacaaccac tacacgcaga agagcctctc cctgtccccg    1380
ggtaaatga                                                            1389
```

<210> SEQ ID NO 3
<211> LENGTH: 240
<212> TYPE: PRT
<213> ORGANISM: Artificial
<220> FEATURE:
<223> OTHER INFORMATION: monoclonal antibody chain

<400> SEQUENCE: 3

```
Met Glu Ala Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ser Ser Gln Ser
        35                  40                  45

Leu Val His Arg Asn Gly Asn Thr Tyr Leu His Trp Tyr Leu Gln Lys
    50                  55                  60

Pro Gly Gln Ser Pro Lys Leu Leu Ile His Lys Val Ser Asn Arg Phe
65                  70                  75                  80

Ser Gly Val Pro Asp Arg Phe Ser Gly Ser Gly Ser Gly Thr Asp Phe
                85                  90                  95
```

```
Thr Leu Lys Ile Ser Arg Val Glu Ala Glu Asp Leu Gly Val Tyr Phe
            100                 105                 110

Cys Ser Gln Ser Thr His Val Pro Pro Leu Thr Phe Gly Ala Gly Thr
            115                 120                 125

Lys Leu Glu Leu Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240

<210> SEQ ID NO 4
<211> LENGTH: 462
<212> TYPE: PRT
<213> ORGANISM: Artificial
<220> FEATURE:
<223> OTHER INFORMATION: monoclonal antibody chain

<400> SEQUENCE: 4

Met Gly Trp Thr Trp Ile Phe Ile Leu Ile Leu Ser Val Thr Thr Gly
1               5                   10                  15

Val His Ser Glu Val Gln Leu Leu Gln Ser Gly Pro Glu Leu Glu Lys
            20                  25                  30

Pro Gly Ala Ser Val Met Ile Ser Cys Lys Ala Ser Gly Ser Ser Phe
        35                  40                  45

Thr Gly Tyr Asn Met Asn Trp Val Arg Gln Asn Ile Gly Lys Ser Leu
    50                  55                  60

Glu Trp Ile Gly Ala Ile Asp Pro Tyr Tyr Gly Gly Thr Ser Tyr Asn
65                  70                  75                  80

Gln Lys Phe Lys Gly Arg Ala Thr Leu Thr Val Asp Lys Ser Ser Ser
                85                  90                  95

Thr Ala Tyr Met His Leu Lys Ser Leu Thr Ser Glu Asp Ser Ala Val
            100                 105                 110

Tyr Tyr Cys Val Ser Gly Met Glu Tyr Trp Gly Gln Gly Thr Ser Val
            115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
210                 215                 220
```

```
Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
            245                 250                 255

Leu Phe Pro Pro Lys Pro Lys Asp Thr Leu Met Ile Ser Arg Thr Pro
        260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
            355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
            405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
    450                 455                 460
```

PREPARATIONS AND METHODS FOR TREATING A GD2 POSITIVE CANCER

CROSS-REFERENCE TO RELATED APPLICATIONS

This application is a continuation of U.S. patent application Ser. No. 15/036,519, filed May 13, 2016, which is a national phase application under 35 U.S.C. § 371 of International Application No. PCT/EP2014/075315 filed 21 Nov. 2014, which claims priority to European Patent Application No. 13193953.0 filed 21 Nov. 2013, Canadian Patent Application No. 2834000 filed 21 Nov. 2013, U.S. patent application Ser. No. 14/086,696 filed 21 Nov. 2013, and U.S. patent application Ser. No. 14/182,776 filed 18 Feb. 2014. The entire contents of each of the above-referenced disclosures is specifically incorporated by reference herein without disclaimer.

FIELD OF THE INVENTION

The present invention relates to preparations and methods for treating a GD2 positive cancer by administering a preparation comprising an anti-GD2 antibody to a patient, wherein the patient is not concomitantly treated with Interleukin-2 (IL-2). In particular, the invention relates to preparations and methods for treating a GD2 positive cancer by administering a preparation comprising a chimeric or humanized anti-GD2 antibody to a patient, wherein the patient is not concomitantly treated with Interleukin-2 (IL-2), and in certain embodiments also not treated with Granulocyte-macrophage colony-stimulating factor (GM-CSF) and/or one or more other cytokines. Furthermore, the invention relates to preparations and methods for the treatment of a GD2 positive cancer in a patient, wherein a preparation comprising an anti-GD2 antibody is administered to the patient as a continuous infusion for one or more days, without concomitantly administering IL-2. The invention further relates to preparations and methods for treating a GD2 positive cancer in a patient by administering a preparation comprising an anti-GD2 antibody to the patient without concomitantly administering IL-2, and wherein one or more treatment periods with the antibody is/are preceded, accompanied, and/or followed by one or more treatment periods with a retinoid. The invention also relates to preparations and methods for treating a GD2 positive cancer by administering a preparation comprising an anti-GD2 antibody as a continuous infusion for 24 hours per day to a patient, wherein the patient is not concomitantly treated with Interleukin-2 (IL-2), and wherein one or more treatment periods with the antibody may be preceded, accompanied, and/or followed by one or more treatment periods with a retinoid.

BACKGROUND TO THE INVENTION

Neuroblastoma, after brain cancer, is the most frequent solid cancer in children under five years of age. In high-risk neuroblastoma, more than half of the patients receiving standard therapy have a relapse and ultimately die from the disease. 90% of cases occur between ages zero to six. The worldwide incidence in industrialized countries is around 2000 cases per year.

Monoclonal antibodies against specific antigens are increasingly being used in oncology. The entirely different mode of action compared to cytotoxic therapies have made them a valuable asset as is shown by forerunners like trastuzumab, cetuximab, bevacizumab, rituximab and others. The disialoganglioside GD2 is a glycosphingolipid expressed primarily on the cell surface. GD2 expression in normal tissues is rare and primarily restricted to the central nervous system (CNS), peripheral nerves and melanocytes. In cancerous cells, GD2 is uniformly expressed in neuroblastomas and most melanomas and to a variable degree in bone and soft-tissue sarcomas, small cell lung cancer, renal cell carcinoma, and brain tumors (Navid et al., Curr Cancer Drug Targets 2010; 10:200-209). Because of the relatively tumor-selective expression combined with its presence on the cell surface, GD2 represents a promising target for antibody-based cancer immunotherapy.

Accordingly, several anti-GD2 antibodies are subject to preclinical or clinical investigation in neuroblastoma, melanoma and other GD2-related cancers.

APN311 is a formulation of the chimeric monoclonal anti-GD2 antibody ch14.18 recombinantly produced in Chinese hamster ovary (CHO) cells, which is the standard mammalian cell line for production of commercially available antibodies. In a Phase I clinical study in relapsed/refractory neuroblastoma patients remissions were achieved with this antibody as single agent. A Phase III trial comprising treatment with APN311 was initiated in 2006 by the International Society of Pediatric Oncology European Neuroblastoma (SIOPEN) and is presently investigating the effects on event-free and overall survival related to treatment with APN311 together with isotretinoin, i.e. cis-retinoic acid (cis-RA), with or without s.c. IL-2. In a comparable US study using a treatment package of 4 drugs, namely a related antibody produced in SP2/0 murine hybridoma cells together with i.v. Interleukin-2 (IL-2 or IL2), Granulocyte-macrophage colony-stimulating factor (GM-CSF) and isotretinoin, interesting survival improvement was seen in children with neuroblastoma in complete remission following initial therapies and no evidence of disease.

APN301 is a formulation of an immunocytokine comprising a humanized anti-GD2 antibody (hu14.18) and IL-2 as a fusion protein. The antibody portion specifically binds to the GD2 antigen that is strongly expressed on neuroblastoma and several other cancers. IL-2 is a cytokine that recruits multiple immune effector cell types. In neuroblastoma patients, APN301 is designed to localize GD2-positive tumor cells via the antibody component. The fused IL-2 then stimulates the patient's immune system against the tumor by activation of both, NK and T cells, whereas the Fc portion of the antibody is designed to trigger tumor cell killing by antibody-dependent cellular cytotoxicity (ADCC) and complement-dependent cytotoxicity (CDC). The immunocytokine has shown activity in a Phase II clinical study in children with relapsed/refractory neuroblastoma (Shusterman et al.; JCO 2010 28(33):4969-75.) and was also tested in a Phase I/II study in late stage malignant melanoma, showing immune activation.

Other anti-GD2 antibodies in research or development are, for example, the monoclonal antibody 3F8 (murine in phase II, as well as humanized in phase I), and 8B6 (specific to 0-acetylated GD2, preclinical). Furthermore, anti-idiotypic antibodies such as e.g. 4B5, 1A7, and A1G4 have been under investigation as potential tumor vaccines, however, their development seems to be abandoned. WO 2008/049643 also describes anti-idiotypic antibodies, which mimic GD2 epitopes, i.e. GD2 mimotopes.

Another version of the 14.18 anti-GD2 antibody is hu14.18K322A as described in WO2005/070967, which has a point mutation in the Fc region in order to reduce CDC, but maintain ADCC, e.g. by expression in a cell line suitable for enhancing ADCC, such as YB2/0. The reduction in CDC is considered to result in reduced pain associated with the antibody treatment.

Anti-tumor activity of antibodies generally occurs via either complement dependent cytotoxicity (CDC or complement fixation) or through antibody dependent cell-mediated cytotoxicity (ADCC). These two activities are known in the art as "effector functions" and are mediated by antibodies, particularly of the IgG class. All of the IgG subclasses except IgG4 (IgG1, IgG2, IgG3) mediate ADCC and complement fixation to some extent, with IgG1 and IgG3 being most potent for both activities. ADCC is believed to occur when Fc receptors on natural killer (NK) cells and/or other Fc receptor bearing immune cells (effector cells) bind to the Fc region of antibodies bound to antigen on a cell's surface. Fc receptor binding signals the effector cell to kill the target cell. CDC is believed to occur by multiple mechanisms; one mechanism is initiated when an antibody binds to an antigen on a cell's surface. Once the antigen-antibody complex is formed, the C1q molecule is believed to bind the antigen-antibody complex. C1q then cleaves itself to initiate a cascade of enzymatic activation and cleavage of other complement proteins, which then bind the target cell surface and facilitate its death through, for example, cell lysis and/or ingestion by macrophages.

It is believed that antibody-dependent cellular cytotoxicity (ADCC) plays an important role in immunotherapy. Unfortunately, ADCC is often depressed in cancer patients. Cytokines are considered to augment ADCC by direct activation of immune cells or by enhancement of tumor-associated antigens (TAA) on tumor cells. For example, Aldesleukin (IL-2) causes activation of natural killer (NK) cells, generation of lymphokine-activated killer (LAK) cells, and augments ADCC. Aldesleukin (IL-2) has been effective at inducing measurable antitumor responses in patients with renal cell carcinoma and melanoma. Furthermore, GM-CSF has been shown both in vitro and in vivo to enhance antitumor immunity through direct activation of monocytes, macrophages, dendritic cells, and antibody-dependent cellular cytotoxicity (ADCC), and indirect T cell activation via TNF, interferon and interleukin 1 (IL-1). GM-CSF is considered to enhance functions of cells critical for immune activation against tumor cells, alone or with other cytokines or monoclonal antibodies.

Thus, in current clinical trials investigating anti-GD2 antibodies, in particular ch14.18, the antibody treatment is combined with cytokine treatment (and retinoid treatment), especially with IL-2 and/or GM-CSF. Accordingly, the prior art teaches that it is advantageous to administer cytokines to GD-2 positive cancer patients, in particular in combination with anti-GD2 antibody treatment.

In contrast, a key aspect of the invention is that such patients can be treated with an anti-GD2 antibody without IL-2, especially without any cytokine treatment.

The treatment with one or more cytokines in combination with the antibody may have severe side effects, such as e.g. fever, allergic reactions, hypotension, capillary leak syndrome etc., which may even lead to death. The accompanying cytokine treatment even potentiates adverse events of the antibody treatment, e.g. pain, since there is a synergy in adverse effects of both drugs. However, with the preparations and methods of the present invention, it is possible to completely omit any cytokine(s). Thus, the present invention results in substantially reduced adverse effects of the treatment with the antibody.

BRIEF DESCRIPTION OF THE INVENTION

In a first aspect, the present invention relates to preparations comprising an anti-GD2 antibody for use in the treatment of a GD2 positive cancer in a patient, wherein the preparation comprising a chimeric or humanized anti-GD2 antibody is administered to the patient without concomitantly administering IL-2, and wherein a GD2 positive cancer is treated.

Furthermore, the invention relates to preparations and methods for the treatment of a GD2 positive cancer in a patient, wherein a preparation comprising a chimeric or humanized anti-GD2 antibody is administered to the patient as a continuous infusion for 24 hours per day without concomitantly administering IL-2. The present invention further relates to preparations and methods for the treatment of a GD2 positive cancer in a patient, wherein a preparation comprising a chimeric or humanized anti-GD2 antibody is administered to the patient without concomitantly administering IL-2, and wherein the one or more anti-GD2 antibody treatment periods is/are preceded, accompanied, and/or followed by one or more treatment periods with a retinoid. In certain embodiments, the patient is not treated with GM-CSF and/or one or more other cytokines, especially not within the same treatment cycle.

The invention is further defined by the specific embodiments and the claims. All embodiments of the invention as further described herein relate to all aspects of the invention equally and all of these aspects may be combined, e.g. the first with the second or third, the first with the second and third, the second with the third, to form a preparation for a method of the combined elements of these aspects; or to form combined methods.

BRIEF DESCRIPTION OF THE FIGURES

FIG. 1 shows Kaplan-Meier curves of the event-free survival (EFS, (A)) and overall survival (OS, (B)) data (in percent over time) of 328 neuroblastoma patients treated with APN311 and isotretinoin, but without IL-2 (in red) and patients treated with APN311 and isotretinoin and IL-2 (in blue).

FIG. 2 shows the comparison of the EFS data (in percent over time) of 128 patients of Example 2 who had a complete response (CR) at start of treatment ((A), the diagram on the right) with the EFS data (in percent over time) of Yu et al. 2010, New England Journal of Medicine 363:1324-1334 ((A), the diagram on the left, also comprising data of complete responders). (B) shows a chart overlay for comparison.

FIG. 3 shows the comparison of the OS data (in percent over time) of 128 patients of Example 2 who had a complete response (CR) at start of treatment ((A), the diagram on the right) with the OS data (in percent over time) of Yu et al. 2010 ((A), the diagram on the left). (B) shows a chart overlay for comparison.

FIGS. 4 and 5 show overview tables of the toxicities (FIG. 4: all grades of toxicities versus grade 3 and 4 only; FIG. 5: all grades of toxicities for each treatment cycle) observed in percent of total evaluated patients treated in the respective schedules with and without IL-2.

FIG. 7: grades 3 and 4 only) observed in all treatment cycles in percent of total evaluated patients treated in the respective schedules with and without IL-2.

FIG. 16 shows results of a complement-dependent cytotoxicity (CDC) assay (blue dots, (A)) and a whole blood test (red dots, WBT, (B)) of blood samples of a neuroblastoma patient during treatment with an anti-GD2 antibody, but without IL-2 and cis-retinioc acid treatment. The purple and grey dots are aliquots of patient samples treated with an anti-id antibody for differentiation of any potential non-specific lysis (i.e. target cell lysis that is not mediated by the antibody). The orange bars indicate the treatment periods with the antibody.

FIG. 17 shows results of a complement-dependent cytotoxicity (CDC) assay (blue dots, (A)) and a whole blood test (red dots, WBT, (B)) of blood samples of a neuroblastoma patient during treatment with an anti-GD2 antibody and with a usual IL-2 dose and cis-retinioc acid treatment. The purple and grey dots are aliquots of patient samples treated with an anti-id antibody for differentiation of any potential non-specific lysis (i.e. target cell lysis that is not mediated by the antibody). The orange bars indicate the treatment periods with the antibody, the green triangles the IL-2 treatment periods, and the light blue asterisks the cis-retinioc acid treatment periods.

DETAILED DESCRIPTION OF THE INVENTION

Figure 6:
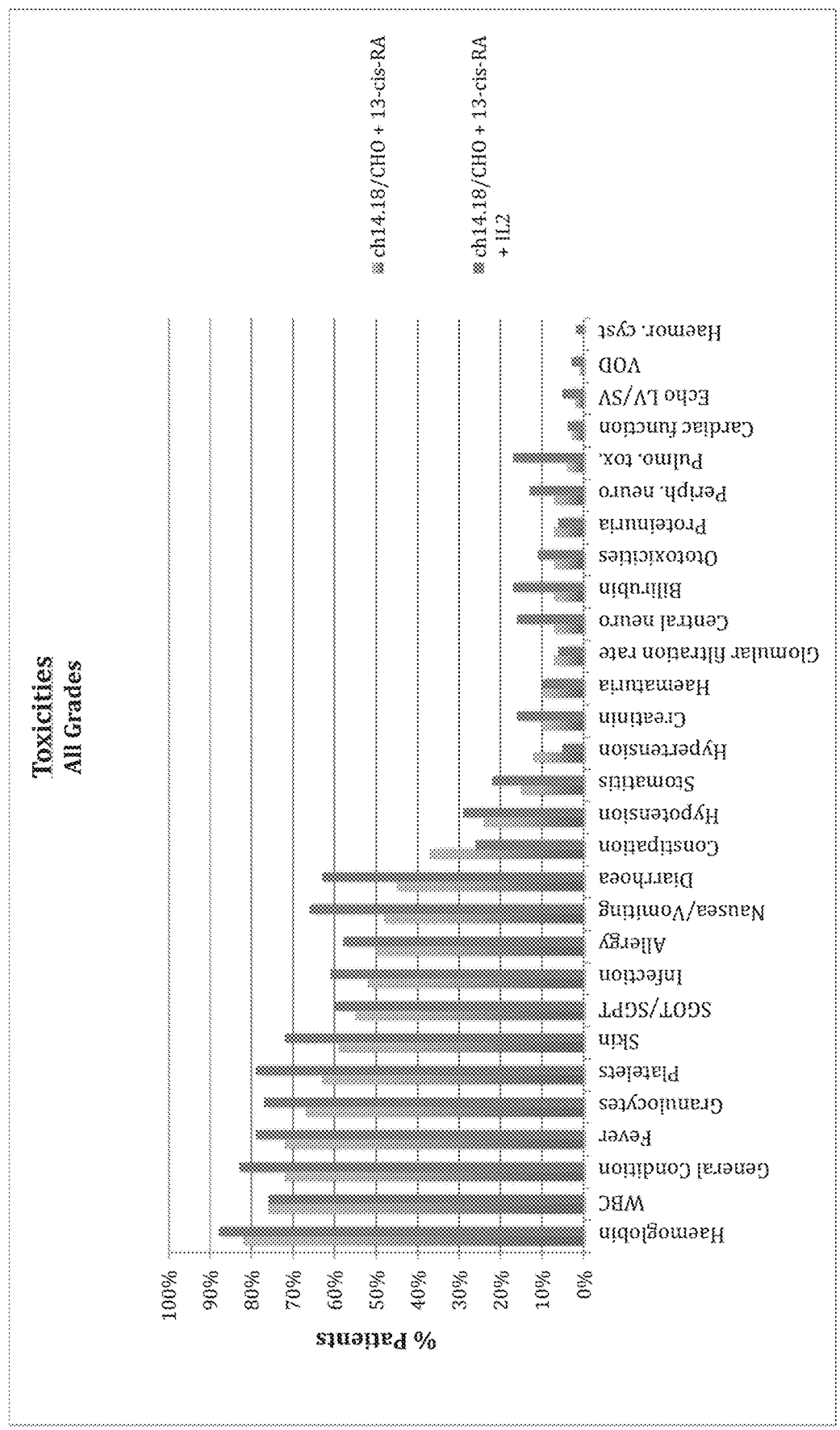
FIGS. 6 and 7 show the respective charts of toxicities (FIG. 6: all grades of toxicities.

It has surprisingly turned out that treatment with one or more cytokines in combination with an anti-GD2 antibody and a retinoid does not provide any clinical benefit over the treatment with the anti-GD2 antibody and a retinoid, but without IL-2, or without IL-2 and without GM-CSF, or even without any cytokine. Furthermore, it turned out that a treatment schedule without IL-2 or other cytokines combined with continuous infusion of a preparation comprising an anti-GD2 antibody is highly advantageous, in particular with regard to reduced side effects, especially pain.

In one aspect, the invention concerns a preparation comprising an anti-GD2 antibody (also referred to as antibody preparation) for use in the treatment of a GD2 positive cancer in a patient, wherein the preparation comprising an anti-GD2 antibody is administered to the patient without concomitantly administering IL-2, and wherein a GD2 positive cancer is treated in the patient.

In another aspect, the invention comprises a method of treating a GD2 positive cancer in a patient comprising administering a preparation comprising an anti-GD2 antibody to the patient without concomitantly administering IL-2, and wherein a GD2 positive cancer is treated in the patient.

In another aspect, the invention comprises a use of an anti-GD2 antibody in the preparation of a medicament for the methods as specified herein.

In certain embodiments, the anti-GD2 antibody is administered to the patient as a continuous infusion for 24 hours per day. In certain embodiments, the anti-GD2 antibody is administered to the patient as a continuous infusion for one or more days. In some embodiment, the patient is treated one or more times with a retinoid preceding, accompanying, and/or following the administration of the anti-GD2 antibody. In some embodiments, the anti-GD2 antibody is a chimeric or humanized anti-GD2 antibody.

The term "patient" as used herein shall mean a human subject suffering from a GD2 positive cancer. The term "treatment" or "treating" as used herein shall mean that a drug or treatment is administered to patient in need thereof. The term "a GD2 positive cancer is treated in the patient" shall mean that a therapeutic effect as further defined below is reached in said patient.

The terms "concomitantly treated with" or "concomitantly administering" as used herein shall mean that one treatment (e.g. with an anti-GD2 antibody and/or a preparation comprising an anti-GD2 antibody, referred to as antibody treatment) is preceded, accompanied, and/or followed by the other one or more treatments (such as e.g. treatment with one or more analgesics, and/or one or more other drugs or treatments), in particular within the same treatment cycle and/or within the same overall treatment time (e.g. in which the anti-GD2 antibody is administered). The treatment period of a concomitant treatment may or may not overlap with the other treatment period (e.g. the antibody treatment period), either partially or entirely. Accordingly, the treatment period of a concomitant treatment (e.g. the analgesic treatment) may precede, accompany, and/or follow the treatment period with the other treatment (e.g. the antibody treatment period). In one embodiment, the treatment periods of concomitant treatments are within the same treatment cycle.

Accordingly, the terms "not concomitantly treated with", "without concomitantly administering" or "not concomitantly administering" as used herein shall mean that one treatment is not preceded, accompanied, and or followed by the one or more other treatments, respectively. In one embodiment, the above defined terms shall mean that a patient is not treated with said drug or treatment (i.e. that said drug or treatment is not administered to said patient) within the same treatment cycle and/or within the same overall treatment time. Accordingly, the treatment period of such a non-concomitant treatment (e.g. cytokine treatment) may not overlap with the other treatment period (e.g. the antibody treatment period), either partially or entirely. In an embodiment, the treatment period of a non-concomitant treatment may not precede, accompany, and/or or follow the treatment period with the other treatment (e.g. the antibody treatment period). In one embodiment, the treatment periods of non-concomitant treatments are not within the same treatment cycle. However, a patient who is not concomitantly treated with a drug or treatment (e.g. one or more cytokines) may have been treated with said drug or treatment (e.g. one or more cytokines) in previous treatment cycles and/or previous overall treatment times.

The term "cytokines" as used herein shall mean proteins, peptides, or glycoproteins which act as hormonal regulators or signaling molecules at nanomolar to picomolar concentrations and help in cell signaling. In an embodiment, the one or more cytokines are selected from immunomodulating agents, such as e.g. interleukins and/or interferons. In an embodiment, the one or more cytokines are selected from the group consisting of IL-2, GM-CSF, Granulocyte colony-stimulating factor (G-CSF), IL-12, and/or IL-15. In one embodiment, the one or more cytokines are not fused to an antibody, in particular not to an anti-GD2 antibody.

The term "reduced dose" or "low-dose" as used herein refers to a dose of the respective drug that is significantly lower, e.g. at least 10%, 20%, 30%, 40%, 50%, 60%, 70%, 80%, 90%, or 100% (or any range in between these doses) lower than the usual dose of the same drug administered in the same or similar setting, i.e. in the same or similar patient groups with the same or similar treatment(s). The usual dose may be the dose that has frequently been used in the past and/or is mainly used in the same or similar setting, i.e. in the same or similar patient groups with the same or similar treatment(s). The dose may be reduced by reducing the daily dose, and/or by reducing the frequency and/or duration of administration. For example, for a 50% reduced dose, the respective drug may be administered in the same frequency or duration as usual, but with only half of the usual daily dose, or the respective drug may be given in the usual daily dose, but e.g. only on every second day, if it has usually been given every day. In another example, 50% of the usual daily dose may be given every second day instead of the usual daily administration, thus, resulting in a reduced dose that is 75% lower than the usual dose. Accordingly, a person skilled in the art can easily determine suitable doses and administration schedules according to the invention.

A "treatment period" with a specific preparation or treatment as used herein means the period of time in which said specific preparation or treatment is administered to the patient within one treatment cycle, e.g. the time period of subsequent treatment days. For example, if the preparation comprising a cytokine is usually administered for 5 consecutive days, followed by one or more days of no administration of the preparation comprising a cytokine, then the treatment period with the preparation comprising a cytokine comprises 5 days. In another example, if the preparation comprising the anti-GD2 antibody is administered continuously over 24 h for 10 consecutive days, followed by one or more days of no administration of the preparation comprising the anti-GD2 antibody, then the treatment period with the preparation comprising the anti-GD2 antibody comprises 10 days. In another example, if isotretinoin is administered twice a day for 14 days, followed by one or more days of no isotretinoin administration, then the treatment period with isotretinoin comprises 14 days. Any such treatment periods may be repeated, entirely or partially overlap with other treatment periods with other drugs or treatments, and/or may be preceded and/or followed by periods of no treatment. For example, a treatment cycle may comprise two 5-day treatment periods with IL-2, the second of which is overlapping with a 10-day (or 14-, 15-, or 21-day) treatment period with ch14.18 (APN311), followed by a 14-day treatment period with isotretinoin.

The terms "combined" or "combination" as used herein in relation to treatment periods shall mean that two or more treatment periods with the same and/or different drugs or treatments are comprised in one treatment cycle. Said two or more treatment periods with different drugs or treatments may partially or entirely overlap, or may not overlap. Any such treatment periods may be combined with (or separated by) one or more intervals of no treatment with the same and/or different drugs or treatments.

The term "treatment cycle" as used herein means a course of one or more treatments or treatment periods that is repeated on a regular schedule, optionally with periods of rest (no treatment) in between. For example, a treatment given for one week followed by three weeks of rest is one treatment cycle. In one embodiment, one treatment cycle comprises one treatment period with the preparation comprising an anti-GD2 antibody. The treatment cycle comprising one treatment period with the preparation comprising an anti-GD2 antibody may further comprise one or more treatment periods with one or more other drugs or treatments (except for cytokine treatment), such as e.g. retinoids, and/or analgesics. Any such treatment periods with one or more drugs or treatments within one treatment cycle may entirely and/or partially overlap. A treatment cycle may also comprise one or more time periods without any treatment. The periods of rest may e.g. be at least 1 day, or 2, 3, 4, 5, 6, 7, 8, 9, 10, 12, 13, or 14 days or more. Alternatively or in combination, the periods of rest may e.g. be at most 8 weeks, 7 weeks, 6 weeks, 5 weeks, 4 weeks, 3 weeks, 2 weeks, 1 week or less. Each treatment in a treatment cycle may preferably be a treatment according to the first, second, third or any combined aspect as defined in the brief description. The treatment schedule according to the invention may comprise 1 or more treatment cycles, in particular two or more, or 3, 4, 5, 6, 7, 8, 9, 10, 11, 12, 13, 14, 15, 16, 17, 18, 19, or 20 or more treatment cycles.

The terms "overall treatment time" or "overall treatment period" as used herein shall mean the continuous treatment period comprising one or more subsequent treatment cycles. A treatment cycle may be repeated, either identically or in an amended form, e.g. with a different dose or schedule, or with one or more different and/or additional treatments (e.g. with one or more other analgesics). The overall treatment time may comprise at least 1, or 2 or more cycles, e.g. up to 10 or up to 20 or even more treatment cycles. In one embodiment, the overall treatment time comprises 1, 2, 3, 4, 5, 6, 7, 8, 9, 10, 11, 12, 13, 14, 15, 16, 17, 18, 19, or 20 cycles or more. As described above, treatment cycles may comprise time periods of no treatment (intervals in which no treatment is administered to the patient, i.e. no antibody, no cytokine, and no other drug). Thus, as used herein, the overall treatment time may also comprise said intervals of no treatment within a treatment cycle and/or between treatment cycles. In one embodiment, a treatment cycle may directly follow after the previous treatment cycle, i.e. with no time period in between treatment cycles. However, the end of a treatment cycle may comprise a time period of no treatment, before the next treatment cycle begins. Example overall treatment times are e.g. at least 6 months, 8 months, 10 months, 12 months, 14 months, 16 months, 18 months, 20 months, 22 months, 24 months, 26 months, 30 months or more.

If a range is given herein, any such range shall include any range in between the given ranges (i.e. the lower and the upper limit of the range). For example, if a range is given of e.g. 1 to 5 days, this shall include 1, 2, 3, 4, and 5 days. The same applies to any other ranges, including but not limited to other time periods (e.g. infusion time in hours), any dose ranges (e.g. per $m^2$ body surface area, per kg body weight, per day, per treatment cycle etc.), infusion rates, concentrations, percentages, factors, ratios, and numbers.

The anti-GD2 antibody or the antibody preparation may be administered to a patient in need thereof. In one embodiment, the patient is a GD2 positive cancer patient. A GD2 positive cancer is a type of cancer, in which GD2 is expressed on tumor cells. GD2 positive cancers are, for example, neuroblastoma, glioblastoma, medulloblastoma, astrocytoma, melanoma, small-cell lung cancer, desmoplastic small round cell tumor, osteosarcoma, rhabdomyosarcoma, and/or other soft tissue sarcomas. In an embodiment, the patient has been diagnosed with neuroblastoma, in particular high risk neuroblastoma. In one embodiment, the patient has been diagnosed with stage 4 neuroblastoma (according to the International Neuroblastoma Staging System (INSS)). In an embodiment, the patient has been diagnosed with minimal residual disease. In an embodiment, the patient has been diagnosed as a complete responder, i.e. as a patient showing a complete response to treatment. In another embodiment, the patient has been diagnosed with relapsed or refractory disease. In one embodiment, the patient suffers from primary refractory or relapsed high risk-neuroblastoma, or from minimal residual disease in high-risk neuroblastoma. The patient may have previously been treated or may be simultaneously treated with one or more other therapies, such as e.g. surgery, chemotherapy, radiation, myeloablative therapy, metaiodobenzylguanidine scintigraphy (mIBG), vaccine therapy, stem cell transplantation, and/or retinoid treatment (e.g. with isotretinoin).

In an embodiment, the patient is not enrolled in a clinical trial of phase I, II or III. In another embodiment, the patient is not enrolled in any clinical trial. In particular, the patient is not enrolled in any clinical trial in any country of the world. Accordingly, the patient is not participating in any systematic investigation and/or officially granted (e.g. by any competent national or regional health authority) tests in medical research and drug development that generate safety and efficacy data for any drug or treatment. In an embodiment, the patient is not participating in any systematic investigation and/or officially granted (e.g. by any competent national or regional health authority) testing for any health interventions (including diagnostics, devices, etc.). The former clinical trials described in the prior art with an anti-GD2 antibody without concomitant treatment with IL-2 and/or any other cytokine have been done to investigate general effects, adverse effects, and doses of the antibody as a basis for further investigation. However, the prior art clearly teaches to finally treat patients with an anti-GD2 antibody in combination with at least one cytokine, especially IL-2. Accordingly, any currently used treatment regimes with an anti-GD2 antibody comprise at least one cytokine, in particular IL-2, also in combination with GM-CSF (see e.g. Yu et al., cited above).

In an embodiment, the anti-GD2 antibody according to the invention specifically binds to the GD2 antigen. GD2 is a disialoganglioside expressed on tumors of neuroectodermal origin. The antibody can be selected from the group of recombinant or artificial, including single chain antibodies, mammalian antibodies, human or humanized antibodies. It may comprise or be selected from constant and/or variable portions of an antibody in particular selected from Fc, Fc-like, Fv, Fab, F(ab)$_2$, Fab', F(ab')$_2$, scFv, scfc, VHH. However, any such antibody fragment should comprise the Fc portion that is responsible for complement binding, and thus, can mediate the natural (or in vivo) effector functions. Preferably the antibody comprises a light and heavy chain of an antibody. The antibody may comprise one or two antigen binding regions, which may bind the same or different antigen, e.g. GD2, that may be bound specifically. The inventive antibodies can be directed—e.g. generated by immunization against—the antigens as defined above. The anti-GD2 antibody may be a humanized or chimeric GD2 antibody, e.g. a humanized or chimeric 14.18, 3F8 or 8B6 antibody, or a murine antibody with the same specificity, or an antigen-binding fragment of any of these which mediates the natural effector functions. In one embodiment, the antibody is not a 14G2a antibody. The anti-GD2 antibody may have one or more amino acid modifications, such as e.g. a modified Fc region. In one embodiment, the anti-GD2 antibody is hu14.18K322A. In another embodiment, the anti-GD2 antibody is a chimeric 14.18 antibody. In one embodiment, the anti-GD2 antibody is encoded by the nucleic acid sequence of SEQ ID NO:1 and/or 2, and/or by the amino acid of SEQ ID NO: 3 and/or 4, or fragments or homologs thereof. In one embodiment, the anti-GD2 antibody is encoded by the amino acid of SEQ ID NO: 3 and/or 4, or fragments or homologs thereof.

The term "fragments or homologs thereof" shall mean any such fragment or homolog of the respective sequence having the same or similar native qualitative activity. In one embodiment, the fragments or homologs have at least 70, 75, 80, 85, 90, 95, 96, 97, 98, or 99% of native qualitative activity. In one embodiment, the fragments or homologs have at least 80, 85, 90, 95, 96, 97, 98, or 99% of sequence identity.

In one embodiment, the anti-GD2 antibody has the light chain nucleotide sequence of SEQ ID NO:1 (see also Example 1) and the heavy chain nucleotide sequence of SEQ ID NO:2 (see also Example 1). In one embodiment, the anti-GD2 antibody has the light chain amino acid sequence of SEQ ID NO:3 (see also Example 1) and the heavy chain amino acid sequence of SEQ ID NO:4 (see also Example 1). The relative molecular mass of the antibody comprising of two light and two heavy chains may be approximately 150,000 Dalton. In one embodiment, the preparation comprising the anti-GD2 antibody is APN311. In one embodiment, the anti-GD2 antibody is dinutuximab. The anti-GD2 antibody may be expressed in CHO cells, in SP2/0 cells, or in other suitable cell lines, such as e.g. HEK-293, MRC-5, Vero, PerC6, or NS0. In an embodiment, the anti-GD2 antibody is a 14.18 antibody. In one embodiment, the anti-GD2 antibody is a chimeric 14.18 antibody expressed in SP2/0 cells (ch14.18/SP2/0). In another embodiment, the anti-GD2 antibody is a chimeric 14.18 antibody expressed in CHO cells (ch14.18/CHO). In an embodiment, the anti-GD2 antibody may also be a fragment or a homolog of the antibody encoded by SEQ ID NOs:1, 2, 3, and/or 4, with the same or similar native qualitative activity.

In certain embodiments, the anti-GD2 antibody is not fused to any other moiety. In certain embodiments, the anti-GD2 antibody is not an immunocytokine. In certain embodiments, the preparation comprising an anti-GD2 antibody does not comprise an immunocytokine. In certain embodiments, the patient is not concomitantly treated with an immunocytokine, in particular not within the same treatment cycle and/or within the same overall treatment time comprising the antibody treatment.

The preparation comprising an anti-GD2 antibody may further comprise salts and WFI, and optionally amino acids, in particular basic amino acids, such as e.g. histidine, arginine and/or lysine. In one embodiment, the preparation comprising an anti-GD2 antibody may further comprise a buffer, e.g. phosphate buffered saline, comprising said salts and WFI. The preparation comprising an anti-GD2 antibody may further comprise stabilizing agents, preservatives and other carriers or excipients. In one embodiment, the preparation comprising an anti-GD2 antibody comprises an anti-GD2 antibody (e.g. ch14.18) and further comprises sucrose, polysorbate 20, histidine, and hydrochloric acid. In an embodiment, the antibody is ch14.18/CHO, the preparation comprising the antibody is APN311 (in an amended formulation), and said preparation comprises 4.5 mg/mL antibody, 50 mg/mL sucrose, 0.1 mg/mL polysorbate 20, and 3.1 mg/mL histidine. The preparation comprising an anti-GD2 antibody may be freeze-dried. The reconstituted solution may have a pH of 6±0.5. In one embodiment, the preparation comprising an anti-GD2 antibody further comprises sucrose, L-arginine, citric acid monohydrate, polysorbate 20, and hydrochloric acid. In an embodiment, said preparation comprises 4 mg/mL anti-GD2 antibody, 20 mg/mL sucrose, 13.9 mg/mL L-arginine, 2 mg/mL polysorbate 20, and 2.1 mg/mL citric acid monohydrate. In an embodiment, said preparation is freeze-dried, can be reconstituted in 4 mL of 0.9% sodium chloride, and the resulting solution has a pH of 5.5 (pH can be adjusted with hydrochloric acid (HCL)). In one embodiment, the preparation comprising an anti-GD2 antibody does not comprise stabilising agents, preservatives and other excipients. The preparation comprising an anti-GD2 antibody may be added to an infusion bag, e.g. an infusion bag containing normal saline, i.e. a physiologic NaCl solution (0.9%), optionally with human serum albumin (HAS, also referred to as human albumin). In an example, the infusion bag comprises normal saline and 0.25-5% human serum albumin, or any range in between these concentrations. In an example, the infusion bag comprises a final volume of 250 ml NaCl 0.9% and 5 ml human albumin 20%, or 100 ml NaCl 0.9% and 5 ml human albumin 20%, or 50 ml NaCl 0.9% and 2 ml human albumin 20%.

The anti-GD2 antibody or the preparation comprising an anti-GD2 antibody may be administered in daily antibody doses of 1 to 30 mg/m$^2$, 1 to 35 mg/m$^2$, 1 to 50 mg/m$^2$, or 1 to 60 mg/m$^2$, e.g. 1, 2, 3, 4, 5, 6, 7, 7.5, 8, 9, 10, 12, 13, 14, 15, 16, 17, 17.5, 18, 19, 20, 25, 30, 32, 35, 40, 45, 50, or 60 mg/m$^2$ or any range in between these doses. In an embodiment, the anti-GD2 antibody or the preparation comprising an anti-GD2 antibody is administered in daily antibody doses of 7, 7.5, 8, 9, 10, 12, 13, 14, 15, 16, 17, 17.5, 18, 19, 20, 25, 30, 32, or 35 mg/m$^2$ or any range in between these doses. For example, a daily dose of 10 mg/m$^2$ means that the patient receives 10 mg anti-GD2 antibody per m$^2$ of body surface per day. As used herein, a dose (e.g. given in mg or microgram) refers to the dose of the active ingredient, i.e. to the amount of active ingredient in the preparation. For example, the given dose may refer to the amount of anti-GD2 antibody in the preparation comprising an anti-GD2 antibody, or the cytokine in the preparation comprising the cytokine, or the morphine or other analgesic in the preparation comprising morphine or other analgesics etc. As specified in the example above, a daily dose of 10 mg/m$^2$ means that the patient receives 10 mg anti-GD2 antibody (optionally contained in a certain volume of the preparation comprising the anti-GD2 antibody) per m$^2$ of body surface per day. As used herein, a dose given per m$^2$ means per m$^2$ of body surface area (BSA) of the patient. As used herein, a dose given per kg means per kg of body weight of the patient.

In some embodiments, the preparation comprising an anti-GD2 antibody is administered in daily doses of 1 to 15, 1 to 20, 1 to 25, 1 to 30, or 1 to 35 mg/m$^2$, or any range in between these daily doses. In certain embodiments, the preparation comprising an anti-GD2 antibody is administered in daily doses of less than 50, 40, 30 or 25 mg/m$^2$. In certain embodiments, the preparation comprising an anti-GD2 antibody is administered in daily doses of up to 7, 10, 15, 17.5 or 20 mg/m$^2$. In one embodiment, the antibody preparation is administered in a dose of 15, 17.5, 20, or 25 mg/m$^2$/day for 4 days. In one embodiment, the antibody preparation is administered in a dose of 50 mg/m$^2$/day for 4 days. The anti-GD2 antibody may be administered in a dose of 10, 20, 25, 50, 60, 65, 68, 70, 75, 80, 100, 120, 150, 200, 210, 250, or 300 mg/m$^2$/cycle or any range in between these doses. The total dose per patient per treatment cycle may be defined as the predetermined overall patient dose.

In some embodiments, the preparation comprising an anti-GD2 antibody is administered as an intravenous infusion over 5 h or more per day, e.g. 5.75 h or more per day, 8 h or more per day, 10 h or more per day, or up to 20 h per day, or up to 24 h per day, or any range in between these time periods, e.g. for 4 or 5 days or more. In other embodiments, the preparation comprising an anti-GD2 antibody is administered as a continuous intravenous infusion over 24 h per day. In certain embodiments, the anti-GD2 antibody is administered as a continuous intravenous infusion over 24 h per day until the predetermined overall patient dose has been administered. In certain embodiments, the anti-GD2 antibody is administered as a continuous intravenous infusion over 24 h per day for one or more days, e.g. for 4, 5, 10, 14, 15, or for up to 21 or more days.

In some embodiments, the preparation comprising an anti-GD2 antibody is administered for a treatment period until a certain therapeutic effect has been reached. In some embodiments, the therapeutic effect may be an increase in immune response to the tumor, as determined, for example, by an increase in immune system biomarkers (e.g. blood parameters, such as lymphocyte counts and/or NK cell numbers; and/or cytokines). In some embodiments, the therapeutic effect may be a reduction in tumor markers (e.g. catecholamines). In some embodiments, the therapeutic effect may be determined by methods such as metaiodobenzylguanidine scintigraphy (mIBG), magnetic resonance imaging (MRI) or X-ray computed tomography (CT), and/or bone marrow histology (assessed by aspirate or trephine biopsy), and/or CDC assays and/or WBTs.

In certain embodiments, the therapeutic effect may be defined as stable disease (i.e. no further increase in lesions, tumor tissue and/or size), partial response (i.e. reduction in lesions, tumor tissue and/or size), and/or complete response (i.e. complete remission of all lesions and tumor tissue.

Complete Response (CR) may be further defined as follows:
Complete disappearance of all measurable and evaluable disease,
no new lesions,
no disease-related symptoms, and/or
no evidence of evaluable disease, including e.g. normalization of markers and/or other abnormal lab values.

In some embodiments, all measurable, evaluable, and non-evaluable lesions and sites must be assessed using the same technique as baseline.

Partial Response (PR) may be further defined as follows:
Applies only to patients with at least one measurable lesion.
Greater than or equal to 50% decrease under baseline in the sum of products of perpendicular diameters of all measurable lesions.
No progression of evaluable disease.
No new lesions.

In some embodiments, all measurable and evaluable lesions and sites must be assessed using the same techniques as baseline.

The preparation comprising an anti-GD2 antibody may be administered as described in PCT/EP2012/061618 or PCT/EP2012/064970. For example, the preparation comprising an anti-GD2 antibody may be administered as continuous intravenous infusion for 24 hours per day. Accordingly, in one aspect, the invention relates to a preparation comprising an anti-GD2 antibody for use in the treatment of a GD2 positive cancer in a patient, wherein the preparation comprising an anti-GD2 antibody is administered to the patient as a continuous infusion for one or more days and for one, two or more treatment cycles, without concomitantly administering IL-2. In another aspect, the invention relates to a preparation comprising an anti-GD2 antibody for use in the treatment of a GD2 positive cancer in a patient, wherein the preparation comprising an anti-GD2 antibody is administered to the patient as a continuous infusion without concomitantly administering IL-2, and wherein the anti-GD2 antibody is not a 14G2a antibody, or wherein the anti-GD2 antibody is a chimeric or humanized anti-GD2 antibody.

The preparation comprising an anti-GD2 antibody may be administered for 4, 5, 10, 14, 15, or 21 consecutive days or any range in between these periods. The preparation comprising an anti-GD2 antibody may also be administered for 1, 2, 3, 4, 5, 6, 7, 8, 9, 10, 11, 12, 13, 14, 15, 16, 17, 18, 19, 20, 21, or more consecutive days. In certain embodiments, the preparation comprising an anti-GD2 antibody is administered over the entire treatment cycle, e.g. for 35 days. In some embodiments, the preparation comprising an anti-GD2 antibody is administered as a continuous intravenous infusion for the overall treatment time, e.g. over 5 treatment cycles with 35 days each, i.e. over 180 days in total. The daily antibody dose may be reduced accordingly, so that the predetermined patient dose of the antibody is administered. In one embodiment, the predetermined patient dose of the antibody is 100 mg/m$^2$/cycle. In one embodiment, the overall treatment time comprises 5 cycles. Accordingly, in this example, the antibody dose per overall treatment time is 500 mg/m$^2$. In an embodiment, this total antibody dose of 500 mg/m$^2$ per overall treatment time is administered over 180 days, i.e. in 2.77 mg/m$^2$/day. The preparation comprising an anti-GD2 antibody may be administered as a continuous intravenous infusion over a time period of 24 hours per day. For such continuous infusion, an osmotic mini-pump may be used. In one embodiment, the preparation comprising an anti-GD2 antibody is administered as continuous intravenous infusion for 24 hours per day for 4, 5, 10, 14, 15 or 21 consecutive days or any range in between these periods, in daily doses as specified above (e.g. 7, 10, 15, 17.5, 20, or 25 mg/m$^2$/day), e.g. 15, 17.5, 20, or 25 mg/m$^2$/day for 4 days, 20 mg/m$^2$/day for 5 days, 10 mg/m$^2$/day for 10 days, 15 mg/m$^2$/day for 10 days, 7 mg/m$^2$/day for 14 days, 15 mg/m$^2$/day for 14 days, 10 mg/m$^2$/day for 15 days, 7 mg/m$^2$/day for 21 days, or 10 mg/m$^2$/day for 21 days or any range in between these doses. In certain embodiments, the preparation comprising an anti-GD2 antibody is not administered as continuous intravenous infusion for 5 days in a daily dose of 40 mg/m$^2$. In certain embodiments, the preparation comprising an anti-GD2 antibody is not administered as continuous intravenous infusion for 5 days, i.e. not as a 120-hour-infusion. In some embodiments, the preparation comprising an anti-GD2 antibody is administered as continuous intravenous infusion for more than 5 days. In some embodiments, the preparation comprising an anti-GD2 antibody is administered as continuous intravenous infusion for 6 or more days.

In one embodiment, the preparation comprising the anti-GD2 antibody is APN311 and is administered in a dose of 10 mg/m$^2$/day for 10 days. In one embodiment, the preparation comprising the anti-GD2 antibody is APN311 and is administered in a dose of 10 mg/m$^2$/day for 10 consecutive days for 1, 2, 3, 4, 5, or 6 or more treatment cycles.

According to the present invention, the patient is not concomitantly treated with IL-2. In certain embodiments, the patient is not concomitantly treated with IL-2 nor GM-CSF. In certain embodiments, the patient is not concomitantly treated with any cytokine. Accordingly, the term "the patient is not concomitantly treated with IL-2, GM-CSF, and/or another cytokine" comprises the respective treatment schedules as described above, i.e. without IL-2, without IL-2 and without GM-CSF, and/or without any cytokine. In an embodiment, the patient is not concomitantly treated with IL-2, GM-CSF, and/or another cytokine within the same treatment cycle. In an embodiment, the patient is not concomitantly treated with IL-2, GM-CSF, and/or another cytokine within the same overall treatment time. In some embodiments, the patient may have been treated with IL-2, GM-CSF, and/or one or more other cytokines in one or more previous treatment cycles and/or overall treatment periods. In some embodiments, the patient has not been treated with IL-2, GM-CSF, and/or one or more other cytokines in one or more previous treatment cycles and/or overall treatment periods. In an embodiment, the antibody treatment period is not preceded, accompanied, and/or followed by one or more treatment periods with IL-2, GM-CSF, and/or one or more other cytokines, i.e. the preparation comprising an anti-GD2 antibody is administered to the patient without concomitantly administering IL-2, GM-CSF, and/or one or more other cytokines. In one embodiment, the treatment period with the preparation comprising an anti-GD2 antibody is not accompanied by one or more treatment periods with a cytokine (or a preparation comprising one or more cytokines), in particular not within the same treatment cycle and/or within the same overall treatment time (comprising the antibody treatment). For example, the patient is not concomitantly treated with Granulocyte colony-stimulating factor (G-CSF), GM-CSF, IL-2, IL-12, and/or IL-15. In an embodiment, the preparation comprising an anti-GD2 antibody is administered to the patient without concomitantly administering IL-2. In an embodiment, the preparation comprising an anti-GD2 antibody is administered to the patient without concomitantly administering GM-CSF. In an embodiment, IL-2 and/or GM-CSF (or a preparation comprising IL-2 and/or GM-CSF) is not administered to the patient within the same treatment cycle that comprises the antibody treatment period(s). In an embodiment, the preparation comprising an anti-GD2 antibody is administered to the patient without concomitantly administering IL-2 and/or GM-CSF. In an embodiment, the preparation comprising an anti-GD2 antibody is administered to the patient without concomitantly administering a cytokine.

The treatment period with the preparation comprising an anti-GD2 antibody may be preceded, accompanied, and/or followed by one or more treatment periods with a retinoid (or a preparation comprising a retinoid). In an embodiment, the one or more treatment periods with the preparation comprising an anti-GD2 antibody is/are followed by one or more treatment periods with a retinoid. Said one or more treatment periods with a retinoid may follow within the same one or more treatment cycles comprising one or more antibody treatment periods, or thereafter, i.e. after the end of the one or more treatment cycles comprising the one or more antibody treatment period, in particular, after the end of the last treatment cycle comprising one or more antibody treatment periods, i.e. at the end of the overall treatment time with the antibody. Accordingly, in an embodiment, there is a time period in between the antibody treatment period and the retinoid treatment period, which may be a time period of no treatment, or may comprise one or more treatment periods with one or more other drugs or treatments.

In one embodiment, the one or more treatment periods with the preparation comprising an anti-GD2 antibody is/are followed by one or more treatment periods with a retinoid within the same treatment cycle. In one embodiment, the treatment cycle comprises at least one treatment period with the preparation comprising an anti-GD2 antibody and at least one treatment period with a retinoid. In an embodiment, the treatment cycle may further comprise one or more time periods of no treatment. In one embodiment, the treatment cycle comprises at least one treatment period with the preparation comprising an anti-GD2 antibody followed by at least one treatment period with a retinoid. In an embodiment, the treatment cycle may comprise at least one time period of no treatment in between the at least one treatment period with the preparation comprising an anti-GD2 antibody and the at least one treatment period with a retinoid.

In one embodiment, the retinoid is a retinoic acid (RA), e.g. isotretinoin (cis-RA). The retinoid may be a first generation retinoid (e.g. retinol, retinal, tretinoin (retinoic acid, Retin-A), isotretinoin, and alitretinoin), a second generation retinoid (e.g. etretinate and its metabolite acitretin), and/or a third generation retinoid (e.g. tazarotene, bexarotene and Adapalene). The retinoid may also be a retinoid derivative, in particular a synthetic retinoid derivative, such as e.g. fenretinide. The preceding or following one or more treatment periods with a retinoid may be a treatment period without antibody and/or IL-2 (or other cytokine) administration.

Any such treatment period may be repeated. Any such treatment period may be followed by an interval of no treatment, either with the same and/or with different drugs or treatments. In one embodiment, the interval may be an interval free of any treatment. In another embodiment, the interval is free of administration of the same preparation or treatment, however, other preparations or treatments may be administered during the interval.

Furthermore, the treatment according to the present invention may be preceded and/or accompanied by a treatment with one or more analgesics (or a preparation comprising one or more analgesics), such as e.g. non-steroidal anti-inflammatory drugs (NSAIDs, e.g. indometacin), and/or one or more opioids, and/or one or more other analgesics, or any combination thereof. In one embodiment, the analgesic is an opioid, e.g. morphine and/or morphine derivatives, such as e.g. hydromorphone. Other opioids are, for example, tramadol, pethidine, codeine, piritramide, levomethadone, as well as fentanyl, alfentanil, remifentanil and sufentanil.

As described above, an anti-GD2 antibody has usually been administered to a patient in combination with one or more cytokines (in the usual doses), especially IL-2 and/or GM-CSF. However, the combination of the antibody treatment with the usual cytokine treatment has potentiated side effects of the antibody treatment, in particular pain. Thus, the treatment with one or more analgesics, especially morphine, was required. It has now surprisingly turned out that anti-GD2 antibody treatment is efficient even without cytokine treatment. Accordingly, by the total omission of any cytokine treatment the pain side effect (and other side effects) can be significantly reduced and thus, the administration of morphine and/or other analgesics can be reduced as well. With the preparations and methods of the invention, it is possible to reduce the dose, to change the route of administration (e.g. from intravenous infusion to oral), to reduce the duration of the analgesic treatment period(s), and/or to change the kind of preparation of the one or more analgesics. Thus, the present invention even allows for an outpatient management, at least for a part of the treatment cycle, of patients on treatment with a preparation comprising an anti-GD2 antibody.

In one embodiment, with an administration schedule according to the invention, i.e. the administration of an anti-GD2 antibody without concomitantly administering IL-2, GM-CSF, and/or another cytokine, the side effects are substantially reduced compared to a treatment schedule comprising concomitant treatment with IL-2, GM-CSF, and/or one or more other cytokines. In another embodiment, the side effect of pain is substantially reduced compared to a treatment schedule comprising concomitant treatment with IL-2, GM-CSF, and/or one or more other cytokines.

Accordingly, in an embodiment, the dose of the one or more analgesics, especially morphine, is reduced within the overall treatment time, within a treatment cycle, during the antibody treatment period within a treatment cycle, from one antibody treatment day to the next antibody treatment day within a treatment cycle, and/or from one treatment cycle to the next.

The dose of analgesics can be further reduced by a long-term infusion of the anti-GD2 antibody, e.g. as continuous i.v. infusion over 24 h per day, as described in PCT/EP2012/061618 and PCT/EP2012/064970, and as described herein. Thus, the analgesic dose can be substantially reduced in an inventive treatment schedule with no IL-2, and in certain embodiments also with no GM-CSF, and in certain embodiments with no other cytokine, in combination with a continuous infusion of the antibody. The term "with no other cytokine" or "with no cytokine" as used herein shall mean that no IL-2 and no GM-CSF is used, and also no other cytokine, i.e. no cytokine is used at all in the respective treatment schedule and/or for the defined treatment time, e.g. within the same treatment cycle and/or within the same overall treatment time. Accordingly, in some embodiments no IL-2 is used. In some embodiments, no IL-2 and no GM-CSF is used. In some embodiments, no cytokine is used. Thus, the term "with no IL-2, and in certain embodiments with no GM-CSF, and in certain embodiments with no other cytokine" shall mean the respective embodiments as described above, namely treatments (e.g. treatment periods, treatment cycles, and/or overall treatment times) without IL-2, without IL-2 and without GM-CSF, and/or without any cytokine.

The one or more analgesics may be administered orally. The one or more analgesics may also be administered as intravenous infusion, especially as continuous intravenous infusion for 24 hours per day. The treatment period with the one or more analgesics may precede and/or accompany the treatment period with the preparation comprising an anti-GD2 antibody.

In some embodiments, the one or more analgesics may be selected from GABA-analogues, such as e.g. gabapentin. Accordingly, the patient may be treated with gabapentin, e.g. three days prior to the start of the antibody treatment period.

The following doses and examples of analgesic treatment are usual doses that may be reduced as described herein. Usually, in this setting Gabapentin is administered orally in a dose of 10 mg/kg/dose once, twice or three times a day. Gabapentin may be given in a dose of up to 300 mg/kg/dose. Gabapentin is available and may be administered as oral solution containing 250 mg/5 mL of gabapentin, or in capsules (100 mg, 300 mg, and 400 mg). The gabapentin treatment may be administered instead of or in addition to the treatment with morphine and/or other analgesics. Furthermore, the patient may be treated with paracetamol (10 to 15 mg/kg/dose, every 4 hours or four times a day, orally or intravenously), ibuprofen (5 to 10 mg/kg/dose orally every 6 to 12 hours), metamizol (10 to 15 mg/kg/dose orally every 4 hours), diphenhydramine (0.5 to 1 mg/kg/dose orally or intravenously), and/or indometacin (e.g. 0.3 to 0.5 mg/kg/dose, or 25 or 50 mg/dose, orally or intravenously every 6 hours). Said treatment with paracetamol, ibuprofen, metamizol, and/or indometacin may be administered instead of in addition to the treatment with morphine and/or gabapentin, and/or other analgesics.

In some embodiments, morphine is used as analgesic, optionally in combination with one or more other analgesics. As an example, some usual morphine doses administered before and/or during a treatment period with a preparation comprising an anti-GD2 antibody are given in table 1. In this example of usual doses, the ch14.18/CHO (APN311) is given as an 8 hour infusion per day on 5 subsequent days in a dose of 20 mg/m$^2$/day and thus 100 mg/m$^2$/cycle, and IL-2 is given s.c. in 6 MIU/m$^2$/day for 5 consecutive days two times per cycle (i.e. 60 MIU/m$^2$/cycle), for 5 cycles, and morphine hydrochloride is given on each antibody treatment day (i.e. each day of a treatment cycle on which the preparation comprising an anti-GD2 antibody is administered to the patient) in a bolus dose of 0.05 mg/kg/h for 2 hours prior to starting the APN311 infusion, in an infusion rate of 0.03 mg/kg/h for 8 hours during the APN311 infusion, and in an interval infusion rate of 0.01 mg/kg/h for 14 hours on the first day of APN311 treatment, and for 4 hours on subsequent treatment days, if tolerated (with an interval of 10 hours with no morphine treatment). The dose was increased (e.g. increase in infusion rate during antibody infusion) and/or additional bolus doses were administered on an as needed basis. Accordingly, the prescribed morphine dose was at least 0.38 mg/kg per day, at least 2 mg/kg per treatment cycle (comprising 5 antibody treatment days), and at least 10 mg/kg per overall treatment time (comprising three cycles).

TABLE 1

Morphine infusion schedule
Prepare 10 mg morphine in 40 mL glucose 5% (0.25 mg = 1 mL)

| | duration of morphine infusion (h) | morphine infusion rate (mg/kg/h) | morphine dose mg/kg |
|---|---|---|---|
| pre-infusion | 2 | 0.05 | 0.1 |
| infusion during APN311 treatment | 8 | 0.03 | 0.24 |
| interval infusion | 14 or 4 | 0.01 | 0.14 or 0.04 |
| total dose per treatment day (mg/kg/24 h) | | | 0.48 or 0.38 |

In another example of usual doses, APN311 is given as an 8 hour infusion per day on 5 subsequent days for 3 cycles in a dose of 10, 20, and 30 mg/m$^2$/day and 50, 100, 150 mg/m$^2$/cycle, and IL-2 is given s.c. in 6 MIU/m$^2$/day for 5 consecutive days two times per cycle (i.e. 60 MIU/m$^2$/cycle), and morphine hydrochloride is given on each antibody treatment day in a bolus dose of 0.5-1.0 mg/kg/dose (just prior to the start of infusion of the antibody), and in a rate of 0.05 mg/kg/hour continuous infusion during the APN311 infusion. The dose is increased (e.g. increase in infusion rate during antibody infusion) and/or additional bolus doses are administered on an as needed basis. Accordingly, the prescribed morphine dose (or usual morphine dose) is at least 0.9 mg/kg per day, at least 4.5 mg/kg per treatment cycle (comprising 5 antibody treatment days), and at least 13.5 mg/kg per overall treatment time (comprising three cycles).

In other examples of usual treatment with ch14.18 and one or more cytokines, morphine has been administered in infusion rates up to 1.2 mg/kg/h over 24 hours.

In still another example of usual doses, ch14.18/Sp2/0 is given in a dose of 25 mg/m$^2$/day on four consecutive days. In one embodiment, each dose of ch14.18/Sp2/0 is infused i.v. over 5.75 or more (maybe extended to up to 20 h), or 10 hours or more (maybe extended to up to 20 h), starting at 1.25 mg/m$^2$/h×0.5 h, then 2.5 mg/m$^2$/h×0.5 h, and optionally further increasing the infusion rate to then 3.75 mg/m$^2$/h×0.5 h, and then to 5 mg/m$^2$/h for the remaining dose, if tolerated. IL-2 is given every second cycle (e.g. cycle 2 and 4) as a continuous i.v. infusion over 4 days (96 h) in 3 MIU/m$^2$/day in week 1 of the treatment cycle and in 4.5 MIU/m$^2$/day in week 2 of the treatment cycle (i.e. 30 MIU/m$^2$/cycle). GM-CSF is given s.c. in a daily dose of 250 mcg/m$^2$. In an embodiment, each treatment cycle starts on day 0, and day 0 of a treatment cycle is the first day of treatment with the respective cytokine. The overall treatment time may comprise 1, 2, 3, 4, or 5 or more treatment cycles. Tables 2, 3, and 4 show examples of usual treatment schedules.

TABLE 2

Schema for the usual administration of 5 cycles of ch14.18/Sp2/0, cytokines, and isotretinoin (retinoic acid or RA).

| Cycle 1 | Cycle 2 | Cycle 3 | Cycle 4 | Cycle 5 |
|---|---|---|---|---|
| Ch14.18 | Ch14.18 | Ch14.18 | Ch14.18 | Ch14.18 |
| GM-CSF | Aldesleukin (IL-2) | GM-CSF | Aldesleukin (IL-2) | GM-CSF |
| RA | RA | RA | RA | RA |

In said example of usual doses, ch14.18/SP2/0 treatment is administered every 28 days at 25 mg/m$^2$/day×4 days for all 5 cycles; GM-CSF at 250 micrograms/m$^2$/day for 14 days; Aldesleukin (IL-2) at 3 MIU/m$^2$/day for first week, and at 4.5 MIU/m$^2$/day for second week.

TABLE 3

Treatment schema for cycles with GM-CSF

| Day | 0 | 1 | 2 | 3 | 4 | 5 | 6 | 7 | 8 | 9 | 10 | 11 | 12 | 13 | 14-23 | 24 |
|---|---|---|---|---|---|---|---|---|---|---|---|---|---|---|---|---|
| GM-CSF | X | X | X | X | X | X | X | X | X | X | X | X | X | X | | Begin Cycle 2&4 |
| ch14.18 | | | | ⇑ | ⇑ | ⇑ | ⇑ | | | | | | | | | |
| RA | | | | | | | | | | | ⇑ | ⇑ | ⇑ | ⇑ | ⇑ | |

Note:
In variation to the treatment schema above, the RA treatment is started on day 11 of the first cycle, but according to the schema on day 10 of the third and fifth cycle. Accordingly, in variation to the treatment schema above, day 24 of the first treatment cycle is also the last day of RA treatment of the first cycle.

In said example of usual doses, GM-CSF is given at 250 micrograms/m$^2$/day as subcutaneous injection (strongly recommended) or i.v. as a 2 hour infusion daily from Day 0 through 13 (daily with the infusion of ch14.18/SP2/0 and for 3 days before and 7 days after the antibody treatment).

TABLE 4

Treatment schema for cycles with Aldesleukin (IL-2)

| Day | 0 | 1 | 2 | 3 | 4-6 | 7 | 8 | 9 | 10 | 11-13 | 14 | 15 | 16 | 17 | 18-27 |
|---|---|---|---|---|---|---|---|---|---|---|---|---|---|---|---|
| IL-2 | X | X | X | X | | X | X | X | X | | | | | | |
| ch14.18 | | | | | | ⇧ | ⇧ | ⇧ | ⇧ | | | | | | |
| RA | | | | | | | | | | | ⇧ | ⇧ | ⇧ | ⇧ | ⇧ |

On days 28-31 of the Aldesleukin cycles no treatment is administered. On day 32, the next treatment cycle (with GM-CSF) is started (day 32=day 0 of the following cycle).

As an example of usual doses, Aldesleukin (Interleukin-2, IL-2) may be given in a dose of 3 MIU/m$^2$/day by continuous infusion (using a CADD® Ambulatory Infusion Pump or a similar infusion pump) for 4 days (on Days 0-3) during the first week of each cycle. During the second week of each cycle, Aldesleukin (IL-2) may be given at 4.5 MIU/m$^2$/day for 4 days (on Days 7 to 10, with the infusion of ch14.18/SP2/0). Aldesleukin may be continuously infused i.v. over 96 hours through a catheter via an ambulatory infusion pump in 5% dextrose in water (may contain 0.1% human serum albumin if needed), total volume dependent upon the pump.

A sixth treatment cycle may be added with 14 days of no treatment (starting on day 24 of the fifth cycle, which is day 0 of the sixth cycle) followed by 14 days of the administration of isotretinoin only.

In an example of usual doses in this setting (i.e. with the treatments as described above), hydroxyzine (1 mg/kg; max dose 50 mg) or diphenhydramine (0.5-1.0 mg/kg; max dose 50 mg) are given i.v. over 10 minutes to start 20 minutes prior to ch14.18/SP2/0 infusion; acetaminophen (10 mg/kg; max dose 650 mg) p.o. is given 20 minutes prior to ch14.18/SP2/0 infusion; and/or a morphine sulfate loading dose of 50 mcg/kg is given immediately prior to ch14.18/SP2/0 administration and then continued with morphine sulfate drip with an infusion rate of 20-50 micrograms/kg/h to continue for two hours after completion of the ch14.18/SP2/0 infusion. Additionally, other narcotics such as hydromorphone or fentanyl may be used. Alternatively, lidocaine infusion may be used in conjunction with an i.v. bolus of morphine, if required. The administration guidelines for lidocaine infusion are shown below:

Administration of lidocaine (in usual doses):
a. Give lidocaine i.v. bolus at 2 mg/kg in 50 cc normal saline (NS) over 30 min prior to the start of ch14.18/SP2/0 infusion.
b. At the beginning of ch14.18/SP2/0 infusion, start i.v. lidocaine infusion at 1 mg/kg/h and continue until two hours after the completion of ch14.18/SP2/0 infusion.
c. May give morphine i.v. bolus 25-50 microgram/kg every 2 h, if needed.

In said example of usual doses, one may also consider the administration of gabapentin with loading doses of morphine, and give morphine infusion/bolus as needed; may start with gabapentin 10 mg/kg/day and titrate up to 30-60 mg/kg/day depending on the clinical response.

In said example of usual doses, doses of hydroxyzine (or diphenhydramine) and acetaminophen can be repeated every 6 h, if needed; i.v. or p.o.

In said example of usual doses, additional morphine doses can be given during the ch14.18/SP2/0 infusion to treat neuropathic pain followed by an increase in the morphine sulfate infusion rate, but patients should be monitored closely. If patients cannot tolerate morphine (e.g., itching), fentanyl or hydromorphone can be substituted for morphine. Alternatively, lidocaine infusion may be used in conjunction with i.v. bolus of morphine, if needed.

The term "morphine dose" as used herein refers to the amount of morphine (in mg or mcg) per kg of body weight of the patient. Accordingly, if it is referred to a daily morphine dose, it is the amount of morphine (in mg or mcg) per kg of body weight of the patient per day, or if it is referred to a morphine dose per hour, it is the amount of morphine (in mg or mcg) per kg of body weight of the patient per hour (or morphine infusion rate), or if it is referred to a morphine dose per treatment cycle, it is the amount of morphine (in mg or mcg) per kg of body weight of the patient per treatment cycle, or if it is referred to a morphine dose per overall treatment time, it is the amount of morphine (in mg or mcg) per kg of body weight of the patient per overall treatment time.

In some embodiments, the morphine and/or other analgesics may be administered in a usual daily dose, but with a reduced frequency of administration, e.g. only every other day, if it has usually been administered each day. In another example, in which the morphine and/or other analgesics have usually been administered as continuous i.v. infusion over several days, either the infusion time per day may be reduced (resulting in a non-continuous infusion), or the total duration of the continuous infusion is reduced, i.e. the number of continuous infusion days.

In some embodiments, the daily dose of the one or more analgesics on one or more antibody treatment days (i.e. a day of a treatment cycle on which the preparation comprising an anti-GD2 antibody is administered to the patient) in a treatment cycle according to the invention (with no IL-2, and in certain embodiments with no IL-2 and no GM-CSF, and in certain embodiments with no cytokine treatment) is lower than the usual daily dose administered on one or more antibody treatment days in a usual treatment cycle (with usual cytokine treatment).

In some embodiments, the daily dose of the one or more analgesics on one or more analgesic treatment days (i.e. a day of a treatment cycle on which one or more analgesics, e.g. morphine, is administered to the patient, which may also be days prior to of after antibody administration) in a treatment cycle according to the invention (with no IL-2, and in certain embodiments with no IL-2 and no GM-CSF, and in certain embodiments with no cytokine treatment) is lower than the usual daily dose administered on one or more analgesic treatment days in a usual treatment cycle (with usual cytokine treatment).

In certain embodiments, the dose (e.g. the daily dose) of the one or more analgesics (e.g. morphine) is reduced over time, e.g. within the overall treatment time, within a treatment cycle, during the antibody treatment period within a treatment cycle, from one antibody or analgesic treatment day to the next antibody or analgesic treatment day within a treatment cycle, and/or from one treatment cycle to the next. In some embodiments, the analgesics dose, in particular the morphine dose, is continuously reduced within a treatment cycle, during the antibody treatment period within a treatment cycle, and/or from one antibody or analgesic/morphine treatment day to the next antibody or analgesic/morphine treatment day within a treatment cycle.

In some embodiments, the daily morphine dose administered during one or more days of administration of the antibody in an infusion schedule with no IL-2, and in certain embodiments with no GM-CSF (and with no IL-2), and in certain embodiments also with no other cytokine according to the invention, and/or the morphine dose of all antibody or morphine treatment days is lower than the daily morphine dose during administration of the antibody with the usual doses of one or more cytokines. In certain embodiments, the daily morphine dose or the morphine dose per cycle administered in an antibody infusion schedule with no IL-2, and in certain embodiments with no GM-CSF, and in certain embodiments with no cytokine is 90% or less, 80% or less, 70% or less, 60% or less, or 50% or less, or 40% or less, or 30% or less, or 20% or less, or 10% or less of the morphine dose administered in or prescribed for an antibody infusion schedule with usual cytokine doses. In some embodiments, the daily morphine dose administered during one or more days of continuous intravenous infusion of the antibody with no IL-2, and in certain embodiments also with no GM-CSF, and in certain embodiments also with no other cytokine according to the invention and/or of all antibody or morphine treatment days is lower than 0.9, 0.72, 0.48, 0.38, 0.4375, and/or 0.205 mg/kg/day.

In some embodiments, morphine is administered only for some but not all days on which the antibody is administered, e.g. only on the first 1, 2, 3, 4, 5, 6, or 7 days of antibody administration with no IL-2, and in certain embodiments with no GM-CSF, and in certain embodiments with no other cytokine. In some embodiments, no morphine is administered on one or more days of antibody administration, or even within the entire treatment cycle. In some embodiments, morphine is administered only in some but not all treatment cycles.

In some embodiments, the morphine infusion rate, i.e. the morphine amount per kg body weight of the patient (or morphine dose) per hour, administered during one or more hours or days of the intravenous infusion of the antibody with no IL-2, and in certain embodiments with no GM-CSF, and in certain embodiments with no other cytokine according to the invention and/or of all hours or days of morphine treatment is lower than the standard morphine infusion rate prescribed for a schedule with usual cytokine doses, and/or lower than the morphine infusion rate in the examples with usual cytokine doses described above. In some embodiments, the morphine infusion rate administered during one or more days of intravenous infusion of the antibody with no IL-2, and in certain embodiments with no GM-CSF, and in certain embodiments with no other cytokine according to the invention and/or of all antibody or morphine treatment days is lower than 50, 40, 30, 20, 10, and/or 5 mcg/kg/h, and/or lower than any range in between these infusion rates. In some embodiments, the morphine infusion rate administered during one or more days of intravenous infusion of the antibody with no IL-2, and in certain embodiments with no GM-CSF, and in certain embodiments with no other cytokine according to the invention and/or of all antibody or morphine treatment days is lower than 50 mcg/kg/h in the first and optionally any following treatment cycles, lower than 40 mcg/kg/h in the second and optionally any following treatment cycles, lower than 30 mcg/kg/h in the third and optionally any following treatment cycles, lower than 20 mcg/kg/h in the fourth and optionally any following treatment cycles, and/or lower than 10 mcg/kg/h in the fifth and optionally any following treatment cycles.

In certain embodiments, the morphine dose per treatment cycle administered during one or more treatment cycles comprising the intravenous infusion of the antibody with no IL-2, and in certain embodiments with no GM-CSF, and in certain embodiments with no other cytokine according to the invention is lower than the morphine dose per treatment cycle in an infusion schedule with usual cytokine treatment, e.g. 90%, 80%, 70%, or less in the first treatment cycle; 80%, 70%, 60%, or less in the second treatment cycle; 60%, 50%, 40%, or less in the third treatment cycle; 45%, 35%, 25%, or less in the fourth treatment cycle; and/or 30%, 20%, 10% or less in the fifth treatment cycle. In certain embodiments, the morphine dose per treatment cycle of the second and any following treatment cycles administered during one or more treatment cycles comprising the intravenous infusion of the antibody with no IL-2, and in certain embodiments with no GM-CSF, and in certain embodiments with no other cytokine according to the invention is lower than the morphine dose per treatment cycle in an antibody infusion schedule with usual cytokine doses. In certain embodiments, the morphine dose of said treatment cycle and any following treatment cycles, and/or of the overall treatment time is lower than the morphine dose per treatment cycle in a usual infusion schedule. In some embodiments, the morphine dose per treatment cycle administered during one or more treatment cycles comprising the intravenous infusion of the antibody with no IL-2, and in certain embodiments with no GM-CSF, and in certain embodiments with no other cytokine according to the invention is lower than 7.2, 4.8, 4.5, 2, 1.75, and/or 0.82 mg/kg/cycle, or lower than any range in between these doses.

In some embodiments, the morphine dose of the overall treatment time in an inventive infusion schedule (i.e. applying a intravenous infusion of the antibody with no IL-2, and in certain embodiments with no GM-CSF, and in certain embodiments with no other cytokine according to the invention) is lower than the morphine dose of the overall treatment time in a usual infusion schedule (i.e. an antibody infusion schedule with the usual cytokine dose(s)). In one embodiment, the morphine dose of the overall treatment time in an inventive infusion schedule is 90% or less, 80% or less, 70% or less, 60% or less, or 50% or less, 40% or less, 30% or less, 20% or less, 10% or less, of the morphine dose of the overall treatment time in a usual infusion schedule, and/or lower than any range in between these doses. In some embodiments, the morphine dose of the overall treatment time in an inventive infusion schedule without cytokine treatment is lower than 43.2, 28.8, 13.5, 10, 8.75, and/or 4.1 mg/kg/overall treatment time, and/or lower than any range in between these doses.

In some embodiments, the reference morphine doses in usual infusion schedules, as referred to herein in comparison to the morphine doses in infusion schedules according to the present invention, refer to the standard morphine doses for said schedule, or morphine doses prescribed for said schedule (e.g. as specified in the clinical study protocols). In some embodiments, the reference morphine doses as referred to herein refers to the morphine dose administered on the first day of treatment with the preparation comprising an anti-GD2 antibody in a treatment cycle with an inventive and/or usual antibody infusion schedule, and is referred to as "starting morphine dose".

Accordingly, the term "reference morphine dose" as used herein shall comprise the morphine doses of treatment schedules other than those according to the present invention (e.g. with cytokine treatment), and/or starting morphine doses (e.g. of treatment schedules with or without cytokine treatment); and shall encompass all examples of such morphine doses as referred to herein in comparison to the other morphine doses in antibody infusion schedules with no IL-2, and in certain embodiments with no IL-2 and with no GM-CSF, and in certain embodiments with no cytokine according to the present invention.

In certain embodiments, the reference morphine dose per hour infusion, i.e. the reference infusion rate, during the administration period of the antibody is 50 mcg/kg/h. In certain embodiments, the reference morphine dose per hour infusion, i.e. the reference infusion rate, during the administration period of the antibody is 30 mcg/kg/h. In certain embodiments, the reference morphine dose is 50, 40, 30, and/or 20 mcg/kg/h. In certain embodiments, the reference morphine dose is 0.9, 0.72, 0.48, 0.38, 0.4375, and/or 0.205 mg/kg/day. In certain embodiments, the reference morphine dose is 7.2, 4.8, 4.5, 2, 1.75, and/or 0.82 mg/kg/cycle. In certain embodiments, the reference morphine dose is 43.2, 28.8, 13.5, 10, 8.75, and/or 4.1 mg/kg/overall treatment time. In certain embodiments, the reference indometacin dose is 0.3 to 0.5 mg/kg/dose, or 25 or 50 mg/dose, orally or intravenously every 6 hours. In some embodiments, the reference morphine doses in usual infusion schedules (with cytokine treatment), as referred to above in comparison to the morphine doses in inventive infusion schedules (without cytokine treatment), refer to the morphine doses as actually administered to the patients (e.g. the respective mean of the morphine doses administered to all treated patients of a group treated in the same setting).

The morphine doses in inventive infusion schedules, as referred to herein in comparison to the morphine doses in usual infusion schedules, may refer to the reduced standard morphine doses for said inventive schedule, or reduced morphine doses prescribed for said schedule (e.g. as specified in the clinical study protocols). In certain embodiments, the reduced morphine dose in an inventive infusion schedule per hour infusion, i.e. the infusion rate, during one or more hours or days of the inventive administration of the antibody with no IL-2, and in certain embodiments with no GM-CSF, and in certain embodiments with no cytokine is lower than 50 mcg/kg/h. In certain embodiments, the morphine dose per hour infusion, i.e. the infusion rate, during one or more hours or days of the inventive administration of the antibody is lower than 30 mcg/kg/h. In some embodiments, the morphine doses in inventive infusion schedules, as referred to above in comparison to the morphine doses in usual infusion schedules, refer to the morphine doses as actually administered to the patients (e.g. the respective mean of the morphine doses administered to all treated patients of a group treated in the same setting).

In general, individual analgesic doses may vary depending on the individual patient's pain tolerance. Dosing may be adapted to obtain optimal analgesia.

The treatment period with the preparation comprising an anti-GD2 antibody may be combined with one or more treatment periods with a retinoid, one or more treatment periods with an analgesic, one or more treatment periods with another drug or treatment (except for cytokine treatment), and/or one or more treatment periods with no treatment. In one embodiment, the treatment period with the preparation comprising an anti-GD2 antibody combined with one or more of any such other treatment periods represent one treatment cycle. Accordingly, in an embodiment a treatment cycle comprises a treatment period with the preparation comprising an anti-GD2 antibody and optionally one or more treatment periods with other drugs, agents, and/or treatments (except for cytokine treatment). Any such treatment periods within one treatment cycle may partially and/or entirely overlap, as further described herein.

In one embodiment, a patient who is treated with the antibody is also treated with a retinoid (e.g. isotretinoin), and optionally morphine, and/or one or more morphine derivatives, and/or one or more other analgesics. In one embodiment, the treatment period with the preparation comprising an anti-GD2 antibody is not preceded and/or followed by a treatment period with one or more cytokines. In one embodiment, the treatment period with the preparation comprising an anti-GD2 antibody is not accompanied by a treatment period with morphine and/or one or more analgesics. In one embodiment, the treatment period with the preparation comprising an anti-GD2 antibody is not accompanied by a treatment period with one or more cytokines. In one embodiment, the treatment period with the preparation comprising an anti-GD2 antibody is not preceded and/or followed by a treatment period with one or more cytokines and not accompanied by a treatment period with one or more cytokines.

In one embodiment, one treatment cycle comprises 28 to 49 days, e.g. 28, 35, 42, or 49 days or any range in between these periods. The treatment cycle starts with the day when the patient first receives any of the treatments comprised in said cycle (may be designated as day 0 or day 1), e.g. the administration of an preparation comprising an anti-GD2 antibody, and/or any other preparation or treatment (except for cytokine treatment).

The treatment period with the anti-GD2 antibody may be preceded, accompanied, and/or followed by a treatment period with a retinoid (e.g. isotretinoin), either directly or with an interval of one or more days of no treatment, e.g. 1, 2, 3, 4, or 5 days of no treatment. In one embodiment, the retinoid (e.g. isotretinoin) is administered orally twice a day in a dose of 160 mg/m$^2$/day (in equal doses, i.e. 2×80 mg/m$^2$). In one embodiment, the retinoid (e.g. isotretinoin) is administered for 14 days, e.g. from day 1 to day 14 of a treatment cycle, or from day 19 to day 32 of the treatment cycle. The treatment period with the retinoid (e.g. isotretinoin) may be followed by an interval of one or more days of no treatment, e.g. 1, 2, 3, 4, or 5 days of no treatment.

In one embodiment, the treatment cycle comprises one 14-day treatment period with the retinoid (e.g. isotretinoin), e.g. on days 1 to 14 of the treatment cycle, followed by 7 days of no treatment (day 15-21 of the treatment cycle), and a 5-day treatment period with the anti-GD2 antibody (e.g. with 20 mg/m$^2$/day infused over 8 hours to administer a dose of 100 mg/m$^2$/cycle), e.g. on days 22 to 26 of the treatment cycle, before the next cycle begins on day 29, which is then day 1 of the next treatment cycle. In other embodiments, the treatment cycle comprises one 14-day treatment period with a retinoid (e.g. isotretinoin), e.g. on days 1 to 14 of the treatment cycle, followed by one 5-day treatment period with the anti-GD2 antibody (e.g. with 20 mg/m$^2$/day infused over 8 hours to administer a dose of 100 mg/m$^2$/cycle), e.g. on days 22 to 28 of the treatment cycle, before the next cycle begins on day 29, which is then day 1 of the next treatment cycle.

In one embodiment, the treatment cycle comprises one 10-day treatment period with the anti-GD2 antibody (e.g. with 10 or 15 mg/m$^2$/day to administer a dose of 100 or 150 mg/m$^2$/cycle), e.g. on days 8 to 17 of the treatment cycle, and one 14-day treatment period with a retinoid (e.g. isotretinoin), e.g. on days 19 to 32 of the treatment cycle, followed by 3 days of no treatment, before the next cycle begins on day 36, which is then day 1 of the second treatment cycle.

In one embodiment, the treatment cycle comprises one 14-day treatment period with the anti-GD2 antibody (e.g. with 7 or 15 mg/m²/day to administer a dose of 100 or 210 mg/m²/cycle), e.g. on days 8 to 21 of the treatment cycle, and one 14-day treatment period with a retinoid (e.g. isotretinoin), e.g. on days 26 to 39 of the treatment cycle, followed by 3 days of no treatment, before the next cycle begins on day 43, which is then day 1 of the second treatment cycle.

In one embodiment, the treatment cycle comprises one 15-day treatment period with the anti-GD2 antibody (e.g. with 10 mg/m²/day to administer a dose of 150 mg/m²/cycle), e.g. on days 8 to 22 of the treatment cycle, and one 14-day treatment period with a retinoid (e.g. isotretinoin), e.g. on days 26 to 39 of the treatment cycle, followed by 3 days of no treatment, before the next cycle begins on day 43, which is then day 1 of the second treatment cycle.

In one embodiment, the treatment cycle comprises one 21-day treatment period with the anti-GD2 antibody (e.g. with 7 or 10 mg/m²/day to administer a dose of 150 or 210 mg/m²/cycle), e.g. on days 8 to 28 of the treatment cycle, and one 14-day treatment period with a retinoid (e.g. isotretinoin), e.g. on days 33 to 46 of the treatment cycle, followed by 3 days of no treatment, before the next cycle begins on day 50, which is then day 1 of the second treatment cycle.

In one embodiment, the treatment cycle comprises one 4-day treatment period with the preparation comprising the anti-GD2 antibody (e.g. ch14.18/SP2/0), for example administered in a dose of 25, 20, 17.5, or 15 mg/m²/day, e.g. on days 3 to 6 of a 24-day treatment cycle beginning with day 0, or on days 7 to 10 of a 32-day treatment cycle beginning with day 0, e.g. for 5 cycles; and one treatment period with RA, e.g. isotretinoin on days 10 to 23 of a treatment cycle beginning with day 0, or on days 14 to 27 of a treatment cycle beginning with day 0. In an embodiment, the treatment schedule is as specified in Table 2, 3 and/or 4, but with no IL-2, and in certain embodiments with no IL-2 and no GM-CSF, and in certain embodiments with no cytokine doses. Accordingly, in an embodiment, the treatment schedule is as specified in Table 2, 3 and/or 4, but with no cytokine.

The treatment cycle may be repeated, either identically or in an amended form, e.g. with a different dose or schedule, or with different additional treatments (e.g. with one or more other analgesics). Thus, the overall treatment time (e.g. the time period comprising all subsequent treatment cycles, or the overall continuous treatment period) may comprise at least 1, or 2 or more cycles, or 10 or more cycles. In one embodiment, the preparation comprising an anti-GD2 antibody is administered to the patient in two or more treatment cycles. In an embodiment, the preparation comprising an anti-GD2 antibody is administered to the patient as a continuous infusion in two or more treatment cycles. In an embodiment, the preparation comprising an anti-GD2 antibody is administered to the patient as a continuous infusion in two or more treatment cycles without concomitantly administering IL-2. In an embodiment, the preparation comprising an anti-GD2 antibody is administered to the patient as a continuous infusion without concomitantly administering IL-2 in 1, 2, 3, 4, 5, 6, 7, 8, 9, 10, 11, 12, 13, 14, 15, 16, 17, 18, 19, or 20 cycles, or more. In one embodiment, the overall treatment time comprises 1, 2, 3, 4, 5, 6, 7, 8, 9, 10, 11, 12, 13, 14, 15, 16, 17, 18, 19, or 20 cycles, or more. The overall treatment time may even comprise up to 20 or more treatment cycles. As described above, treatment cycles may comprise time periods of no treatment (intervals in which no treatment is administered to the patient, i.e. no antibody, no cytokine, no other drug). Thus, as used herein, the overall treatment time may also comprise said intervals of no treatment within treatment cycles.

In one embodiment, the 35, 42, or 49 day treatment cycle as specified above is repeated at least 4 or 5 times, so that the overall continuous treatment period comprises at least 5 or 6 treatment cycles.

The effect of the antibody treatment without one or more cytokines may be determined by a complement dependent cytolysis (CDC) assay or a whole blood test (WBT). The WBT is an assay in which the target cells or target components (i.e. cells, liposomes or other cell-like compartments to be lysed) are contacted with appropriately anti-coagulated whole blood from the patient. The CDC assay can be, for example, a standard CDC assay as known in the art (e.g. as described in Indusogie et al., J Immunol 2000; 164(8):4178-84; Zeng et al. Molecular Immunology 2005; 42(11):1311-9; or in WO2005/070967). The CDC assay and/or the WBT may be done with GD2 positive target cells, such as tumor cell lines of the GD2 positive cancer to be treated. For example, if the patient to be treated suffers from neuroblastoma, the cell line may be a neuroblastoma cell line, such as e.g. LAN-1 human neuroblastoma cells. In another example, if the patient to be treated suffers from melanoma, the cell line may be a melanoma cell line, such as e.g. M21 human melanoma cells. In still another example, the target cells of the CDC assay and/or the WBT are tumor cells obtained from the patient, i.e. autologous tumor cells of the patient. In another embodiment, the target component of the CDC assay and/or WBT is a liposome displaying GD2 on the surface. The target cells or target components are labeled with a signaling component, e.g. with a radioactive component, such as 51Cr, or with a fluorescent component, such as calcein. The signaling component is comprised by the target cell or target component, i.e. is inside of the target cell or target component (e.g. a liposome packed with the signaling component and displaying GD2 on the surface), and is released upon lysis of the target cell or target component. Thus, the signaling component provides the assay readout. The target cells or components loaded with the signaling compound are contacted with the whole blood, serum, or plasma in a certain ratio. The whole blood, plasma, or serum may be diluted for the CDC or WBT, e.g. in a ratio of 1:2 or higher, e.g. 1:4, 1:5, or 1:10, or any range in between these ratios prior to adding it to the sample. However, it may also be added to the sample un-diluted. The final concentration of the whole blood, plasma, or serum in the CDC or WBT sample may e.g. be in the range of 10 to 50%. Target cell or target component lysis can be measured by release of said signaling component by a scintillation counter or spectrophotometry. For example, the target cell or target component lysis can be measured by determining the amount of 51Cr released into the supernatant by a scintillation counter. The percentage of lysis may be determined by the following equation: 100×(experimental release−spontaneous release)/(maximum release−spontaneous release).

For the CDC assay, the cytolytic components (or effector components) are provided by serum or appropriately anti-coagulated plasma obtained from the patient or donor comprising the complement system components. For the WBT, the cytolytic components (or effector components) are provided by appropriately anti-coagulated whole blood obtained from the patient or donor comprising the complement system components as well as all cellular components, and also any further components comprised in whole blood which might be relevant to the target cell lysis, as well as the interplay of all components (e.g. complement activation is known to activate certain effector cells such as granulocytes) For the CDC and/or WBT, the serum, plasma, or whole blood may be added to the target cells or target components in different dilutions.

Furthermore, one or more samples of the CDC assay and/or WBT may be spiked with an anti-GD2 antibody in different concentrations, e.g. for generation of a standard curve.

In another embodiment, one or more anti-idiotypic (anti-id) anti-GD2 antibodies recognizing the variable domain of anti-GD2 antibodies may be added to a sample to inhibit the target cell lysis mediated by the antibody, e.g. as a negative control or to prove specificity of the assay and that the target cell lysis measured without the anti-id antibody is antibody-mediated or antibody dependent.

In certain embodiments, the increased level of cytolysis after the one or more initial antibody treatment days (compared to the level of cytolysis prior to antibody treatment) is maintained over the entire treatment cycle. In some embodiments, said increased level of cytolysis is maintained over the overall treatment time, i.e. even for time periods, where the patient is not treated with the preparation comprising an anti-GD2 antibody, i.e. in the intervals between the treatment periods with the preparation comprising an anti-GD2 antibody (if any, i.e. if the patient is not treated continuously over the overall treatment time with the preparation comprising an anti-GD2 antibody).

In one embodiment, the level of cytolysis (level of target cell lysis, e.g. measured in a CDC assay or WBT) of a blood sample of a patient treated according to the present invention is increased compared to the level of cytolysis prior to the first treatment period with the preparation comprising the antibody over the entire time period starting from the end of the first antibody treatment period to the end of the last treatment cycle, i.e. even between the time periods of antibody treatment. In one embodiment, said level of cytolysis is at least 10%, 20%, 30%, 40%, 50%, 60%, 70%, 80%, 90% or 100%, or any range in between these levels, over the entire time period starting from the end of the first antibody treatment period to the end of the last treatment cycle. In an embodiment, the level of cytolysis after the first, second, third, fourth, fifth, sixth, seventh, eighths, ninths, and/or tenth treatment period with the anti-GD2 antibody is at least 10%, 20%, 30%, 40%, 50%, 60%, 70%, 80%, 90% or 100%, or any range in between these levels. In an embodiment, the level of cytolysis prior to the second, third, fourth, fifth, sixth, seventh, eighths, ninths, and/or tenth treatment period with the anti-GD2 antibody is at least 10%, 20%, 30%, 40%, 50%, 60%, 70%, 80%, 90% or 100%, or any range in between these levels.

EXAMPLES

Example 1: APN311 Sequences and Related Data

APN311 Sequence Data

TABLE 5

| | Molecular Weight (MW) and pI (calculated) | | | | |
|---|---|---|---|---|---|
| | pI[1] | MW [D][1] | No. of AS | Conditions | 2D-DIGE[2] |
| Antibody | 8.61 | 144701.10 | 1324 | non-reducing | x |
| Antibody (1/2) | 8.58 | 72359.56 | 662 | reducing | x |
| Heavy Chain | 8.58 | 48306.59 | 442 | reducing | x |
| Light Chain | 8.48 | 24070.98 | 220 | reducing | x |

[1] Calculated via http://web.expasy.org/compute_pi/
[2] Due to the molecular weight of the dyes, shifts to slightly higher molecular weights are to be expected for 2D-DIGE Nucleotide Sequence (cDNA, Incl. Leader)

"TAG" works as a "stop codon" and therefore is not translated into the peptide sequence.

```
Light Chain (SEQ ID NO:1):

1 ~~ATG GAA ACC CCA GCG CAG CTT CTC TTC CTC CTG CTA CTC TGG CTC CCA GAT ACC ACT GGA~~

61 GAA ATA GTG ATG ACG CAG TCT CCA GCC ACC CTG TCT GTG TCT CCA GGG GAA AGA GCC ACC

121 CTC TCC TGC AGA TCT AGT CAG ACT CTT GTA CAC CGT AAT GGA AAC ACC TAT TTA CAT TGG

181 TAC CTG CAG AAG CCA GGC CAG TCT CCA AAG CTC CTG ATT CAC AAA GTT TCC AAC CGA TTT

241 TCT GGG GTC CCA GAC AGG TTC AGT GGC ACT GGA TCA GGG ACA GAT TTC ACA CTC AAG ATC

301 AGC AGA GTG GAG GCT GAG GAT CTG GGA GTT TAT TTC TGT TCT CAA AGT ACA CAT GTT CCT

361 CCG CTC ACG TTC GGT GCT GGG ACC AAG CTG GAG CTG AAA CGA ACT GTG GCT GCA CCA TCT

421 GTC TTC ATC TTC CCG CCA TCT GAT GAG CAG TTG AAA TCT GGA ACT GCC TCT GTT GTG TGC

481 CTG CTG AAT AAC TTC TAT CCC AGA GAG GCC AAA GTA CAG TGG AAG GTG GAT AAC GCC CTC

541 CAA TCG GGT AAC TCC CAG GAG AGT GTC ACA GAG CAG GAC AGC AAG GAC AGC ACC TAC AGC

601 CTC AGC AGC AGC CTG ACG CTG AGC AAA GCA GAC TAC GAG AAA CAC AAA GTC TAC GCC TGC

661 GAA GTC ACC CAT CAG GGC CTG AGC TCG CCC GTC ACA AAG AGC TTC AAC AGG GGA GAG TGT

721 ~~TAG~~
```

-continued

Heavy Chain (SEQ ID NO:2):

```
   1 ATG GGA TGG ACC TGG ATC TTT ATT TTA ATC CTG TCG GTA ACT ACA GGT GTC CAC TCT GAG
  61 GTC CAA CTG CTG CAG TCT GGA CCT GAG CTG GAG AAG CCT GGC GCT TCA GTG ATG ATA TCC
 121 TGC AAG GCT TCT GGT TCC TCA TTC ACT GGC TAC AAC ATG AAC TGG GTG AGG CAG AAC ATT
 181 GGA AAG AGC CTT GAA TGG ATT GGA GCT ATT GAT CCT TAC TAT GGT GGA ACT AGC TAC AAC
 241 CAG AAG TTC AAG GGC AGG GCC ACA TTG ACT GTA GAC AAA TCG TCC AGC ACA GCC TAC ATG
 301 CAC CTC AAG AGC CTG ACA TCT GAG GAC TCT GCA GTC TAT TAC TGT GTA AGC GGA ATG GAG
 361 TAC TGG GGT CAA GGA ACC TCA GTC ACC GTC TCC TCA GCC TCC ACC AAG GGC CCA TCG GTC
 421 TTC CCC CTG GCA CCC TCC TCC AAG AGC ACC TCT GGG GGC ACA GCG GCC CTG GGC TGC CTG
 481 GTC AAG GAC TAC TTC CCC GAA CCG GTG ACG GTG TCG TGG AAC TCA GGC GCC CTG ACC AGC
 541 GGC GTG CAC ACC TTC CCG GCT GTC CTA CAG TCC TCA GGA CTC TAC TCC CTC AGC AGC GTG
 601 GTG ACC GTG CCC TCC AGC AGC TTG GGC ACC CAG ACC TAC ATC TGC AAC GTG AAT CAC AAG
 661 CCC AGC AAC ACC AAG GTG GAC AAG AGA GTT GAG CCC AAA TCT TGT GAC AAA ACT CAC ACA
 721 TGC CCA CCG TGC CCA GCA CCT GAA CTC CTG GGG GGA CCG TCA GTC TTC CTC TTC CCC CCA
 781 AAA CCC AAG GAC ACC CTC ATG ATC TCC CGG ACC CCT GAG GTC ACA TGC GTG GTG GTG GAC
 841 GTG AGC CAC GAA GAC CCT GAG GTC AAG TTC AAC TGG TAC GTG GAC GGC GTG GAG GTG CAT
 901 AAT GCC AAG ACA AAG CCG CGG GAG GAG CAG TAC AAC AGC ACG TAC CGT GTG GTC AGC GTC
 961 CTC ACC GTC CTG CAC CAG GAC TGG CTG AAT GGC AAG GAG TAC AAG TGC AAG GTC TCC AAC
1021 AAA GCC CTC CCA GCC CCC ATC GAG AAA ACC ATC TCC AAA GCC AAA GGG CAG CCC CGA GAA
1081 CCA CAG GTG TAC ACC CTG CCC CCA TCC CGG GAG GAG ATG ACC AAG AAC CAG GTC AGC CTG
1141 ACC TGC CTG GTC AAA GGC TTC TAT CCC AGC GAC ATC GCC GTG GAG TGG GAG AGC AAT GGG
1201 CAG CCG GAG AAC AAC TAC AAG ACC ACG CCT CCC GTG CTG GAC TCC GAC GGC TCC TTC TTC
1261 CTC TAT AGC AAG CTC ACC GTG GAC AAG AGC AGG TGG CAG CAG GGG AAC GTC TTC TCA TGC
1321 TCC GTG ATG CAT GAG GCT CTG CAC AAC CAC TAC ACG CAG AAG AGC CTC TCC CTG TCC CCG
1381 GGT AAA TGA
``` nucleotide 1 to 60 (striked out): leader sequence
last nucleotide (striked out): stop codon PEPTIDE SEQUENCE (Incl. Signal Peptide)
The signal peptide is split off during post translational processing and is not part of the final recombinant protein anymore.

Light Chain (SEQ ID NO:3):

```
   1  M E A P A Q L L F L L L L W L P D T T G
  21  E I V M T Q S P A T L S V S P G E R A T
  41  L S C R S S Q S L V H R N G N T Y L H W
  61  Y L Q K P G Q S P K L L I H K V S N R F
  81  S G V P D R F S G S G S G T D F T L K I
 101  S R V E A E D L G V Y F C S Q S T H V P
 121  P L T F G A G T K L E L K R T V A A P S
 141  V F I F P P S D E Q L K S G T A S V V C
 161  L L N N F Y P R E A K V Q W K V D N A L
 181  Q S G N S Q E S V T E Q D S K D S T Y S
 201  L S S T L T L S K A D Y E K H K V Y A C
 221  E V T H Q G L S S P V T K S F N R G E C
```

Heavy Chain (SEQ ID NO:4):

```
   1  M G W T W I F I L I L S V T T G V H S E
  21  V Q L L Q S G P E L E K P G A S V M I S
  41  C K A S G S S F T G Y N M N W V R Q N I
  61  G K S L E W I G A I D P Y Y G G T S Y N
```

-continued

```
 81  Q K F K G R A T L T V D K S S S T A Y M

101  H L K S L T S E D S A V Y Y C V S G M E

121  Y W G Q G T S V T V S S A S T K G P S V

141  F P L A P S S K S T S G G T A A L G C L

161  V K D Y F P E P V T V S W N S G A L T S

181  G V H T F P A V L Q S S G L Y S L S S V

201  V T V P S S S L G T Q T Y I C N V N H K

221  P S N T K V D K R V E P K S C D K T H T

241  C P P C P A P E L L G G P S V F L F P P

261  K P K D T L M I S R T P E V T C V V V D

281  V S H E D P E V K F N W Y V D G V E V H

301  N A K T K P R E E Q Y N S T Y R V V S V

321  L T V L H Q D W L N G K E Y K C K V S N

341  K A L P A P I E K T I S K A K G Q P R E

361  P Q V Y T L P P S R E E M T K N Q V S L

381  T C L V K G F Y P S D I A V E W E S N G

401  Q P E N N Y K T T P P V L D S D G S F F

421  L Y S K L T V D K S R W Q Q G N V F S C

441  S V M H E A L H N H Y T Q K S L S L S P

461  G K
``` amino acid 1 to 20 (striked out): leader sequence

Two GMP compliant batches of the ch14.18/CHO (APN311) antibody have been produced. These two batches of the drug that have been produced are Lot T651204-A (containing 4.3 ml (4.6 mg/ml) antibody) and Lot T900310-A (containing 4.5 ml (4.5 mg/ml) antibody. The APN311 monoclonal antibody bulk preparation is manufactured as a concentrate for the preparation of IV infusions.

TABLE 6

Composition of the final APN311 preparation

| | |
|---|---|
| Product Name | Mouse-human chimeric monoclonal anti-GD2 IgG1 antibody (ch 14.18/CHO; APN311) |
| Content | 4.25-4.75 mg/ml (the exact content per mL may slightly vary from lot to lot and is given on each vial) |
| Buffer | 20 mM histidine, 5% saccharose, 0.01% Tween 20, WFI |
| pH Value | 5.5-6.5 |
| Excipient | None |

Preparation Guide

The antibody must be prepared under sterile conditions. The appropriate volume of ch14.18/CHO antibody (APN311) should be withdrawn from the vials. It is recommended that the antibody solution is filtered (0.2 to 1.2 µm) before injection into the patient either by using an in-line filter during infusion (as some centres do routinely) or by filtering the solution with a particle filter (e.g. filter Nr. MF1830, Impromediform, Germany). The volume of the antibody is added to an infusion bag containing NaCl 0.9% and 1% human serum albumin (HSA), e.g. 100 ml NaCl 0.9% and 5 ml human serum albumin 20%.

Calculation of the Quantity of Ch14.18/CHO (APN311) to be Diluted

The amount of ch14.18/CHO (APN311) to be administered is calculated as follows: Dosage: 10 mg/m$^2$/day, day 8-17, as 24 h infusion.

Example calculation: If a patient has a body surface area (BSA) of 0.7, he/she needs 7 mg (10×0.7) per day, or 70 mg for ten treatment days (one cycle).

Example 2: Patients Treated with APN311 without IL-2 (and without Other Cytokines) in Comparison to Data of Yu et al. 2010, NEJM (Cited Above)

The data underlying this example have been generated in the High Risk Neuroblastoma Study 1.5 of SIOP-Europe (SIOPEN), EudraCT number 2006-001489-17. Patients with high risk neuroblastoma after myeloablative therapy (MAT) and autologous stem cell rescue (ASCR), and as the case may be, also other treatments, such as radiation, other chemotherapies, surgery etc., have received up to 5 cycles of 20 mg/m$^2$/day ch14.18/CHO administered as an 8 hour i.v. infusion for 5 consecutive days (days 22 to 26 of the treatment cycle) in 28-day cycles. This corresponds to a total dose of 100 mg/m$^2$/cycle ch14.18/CHO. cis-RA has been administered orally twice a day in a dose of 160 mg/m$^2$/day on days 1 to 14 of the treatment cycle (in two equal doses per day, i.e. 2×80 mg/m$^2$). In one group, no IL-2 has been administered during a treatment cycle and during the overall treatment time. The patients of the other group received IL-2 at a dose of 6×10$^6$ IU/m$^2$/day on days 15 to 19 and 22 to 26 of a treatment cycle. The patients were treated in 6 treatment cycles, wherein treatment cycles 1 to 5 were as described above, and the sixth treatment cycle comprised the treatment period with isotretinoin only (no antibody and no IL-2 administered).

Event-free and overall survival was analyzed. EFS and OS were also analyzed in the subgroup of patients who presented as complete responders at the start of antibody treatment (no evidence of tumor by any applied examination). The EFS and OS data of this subgroup has been compared to the EFS and OS data of a treatment schedule with antibody, IL-2 and GM-CSF, and isotretinoin (cis-RA), as described in Yu et al. (NEJM 2010, cited above), and are included in Table 7.

The patients in Yu et al. have been treated with ch14.18/Sp2/0 given in a dose of 25 mg/m$^2$/day on four consecutive days, each dose of ch14.18/Sp2/0 is infused i.v. over 5.75 hours or 10 h (may have been extended to up to 20 h for anticipated toxicities). IL-2 is given every second cycle (e.g. cycle 2 and 4) as a continuous i.v. infusion over 4 days (96 h) in 3 MIU/m$^2$/day in week 1 of the treatment cycle and in 4.5 MIU/m$^2$/day in week 2 of the treatment cycle (i.e. 30 MIU/m$^2$/cycle). GM-CSF is given s.c. in a daily dose of 250 mcg/m$^2$ for 14 days (from Day 0 through 13). The overall treatment time comprises 5 treatment cycles. See also Tables 2, 3, and 4 for the respective treatment schedules. The EFS and OS Figures of Yu et al. that are depicted here in FIGS. 2 and 3 for comparison include only the complete responders of the above described treatment. Therefore, only the subgroup of complete responders to the inventive treatment have been used for direct comparison.

TABLE 7

2-year event-free survival (EFS) and overall survival (OS) of complete responders (CR) of APN311-302 in comparison to Yu et al. (NEJM 2010, cited above) in percent

|  | 2y EFS in % | 2y OS in % |
| --- | --- | --- |
| Subgroup of CR at start of randomization in APN311-302 study: APN311 + cis-RA | 70 | 81 |
| NEJM 2010: ch14.18 + IL2 + GM-CSF + cis-RA | 66 | 86 |
| NEJM 2010: cis RA only | 46 | 75 |

Figure 7:
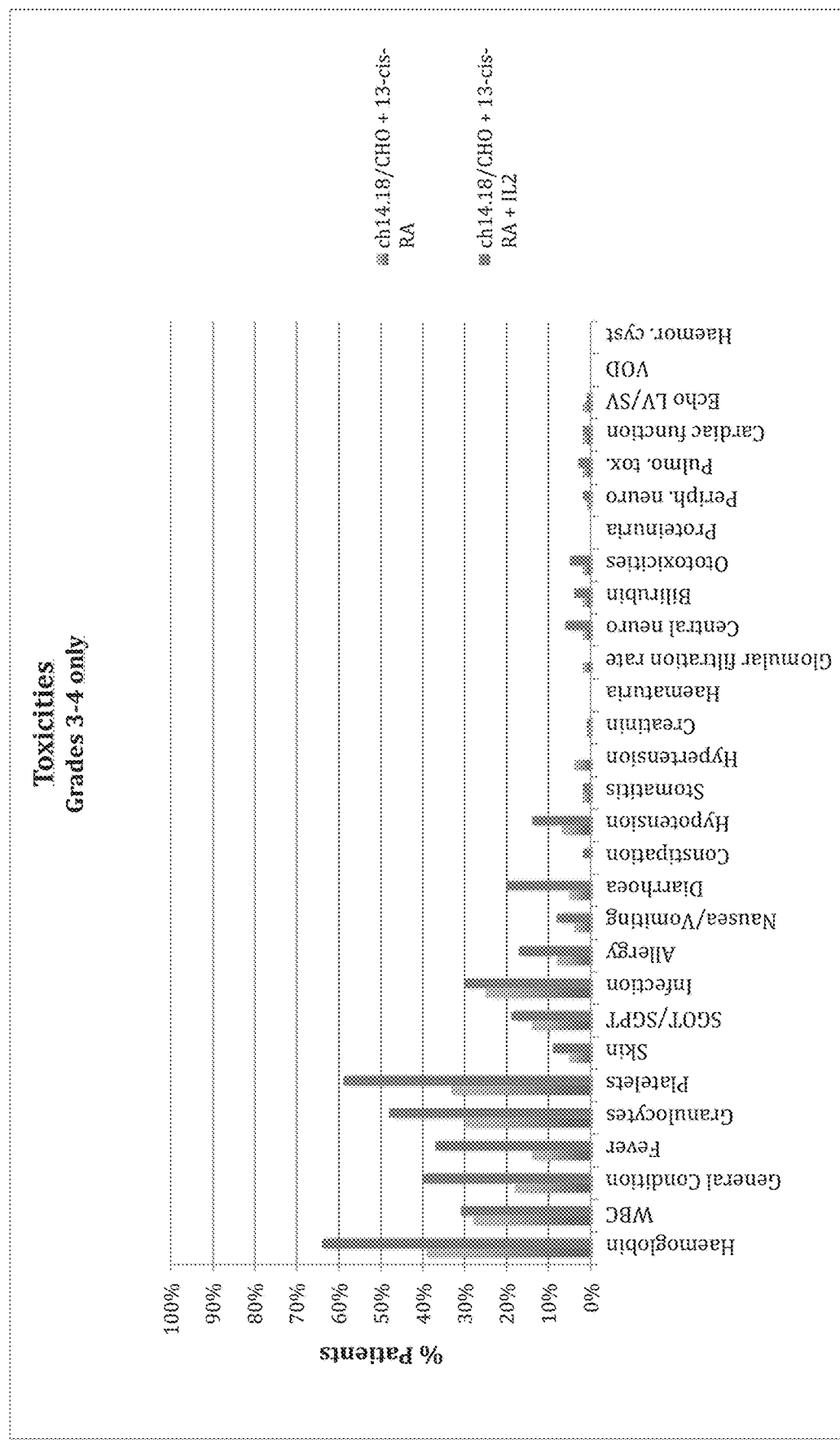
Figure 8:
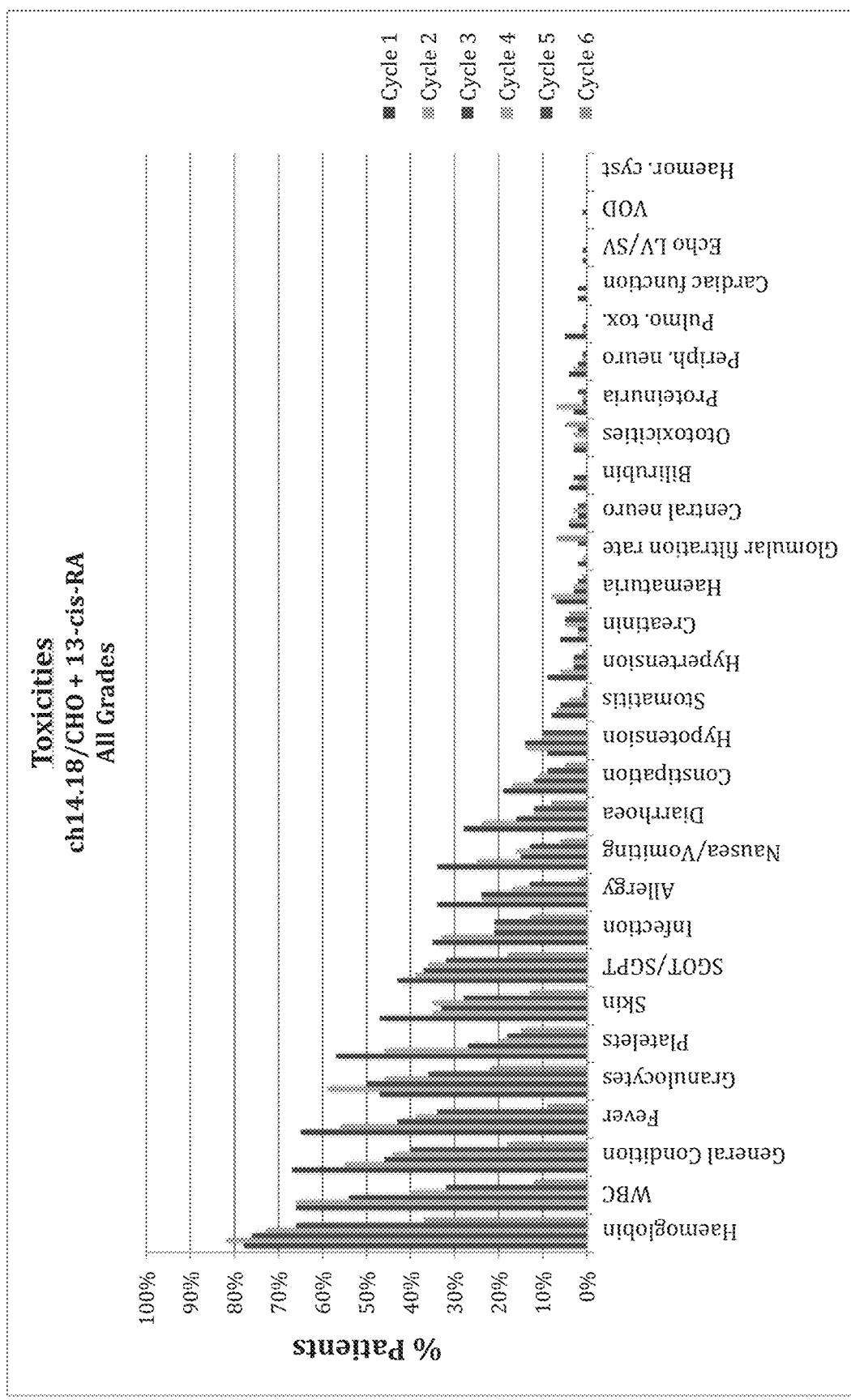
FIGS. 8 and 9 show charts of all grade toxicities per treatment cycle in percent of total evaluated patients treated in the respective schedules with IL-2 (FIG. 9) and without IL-2 (FIG. 8).
Figure 9:
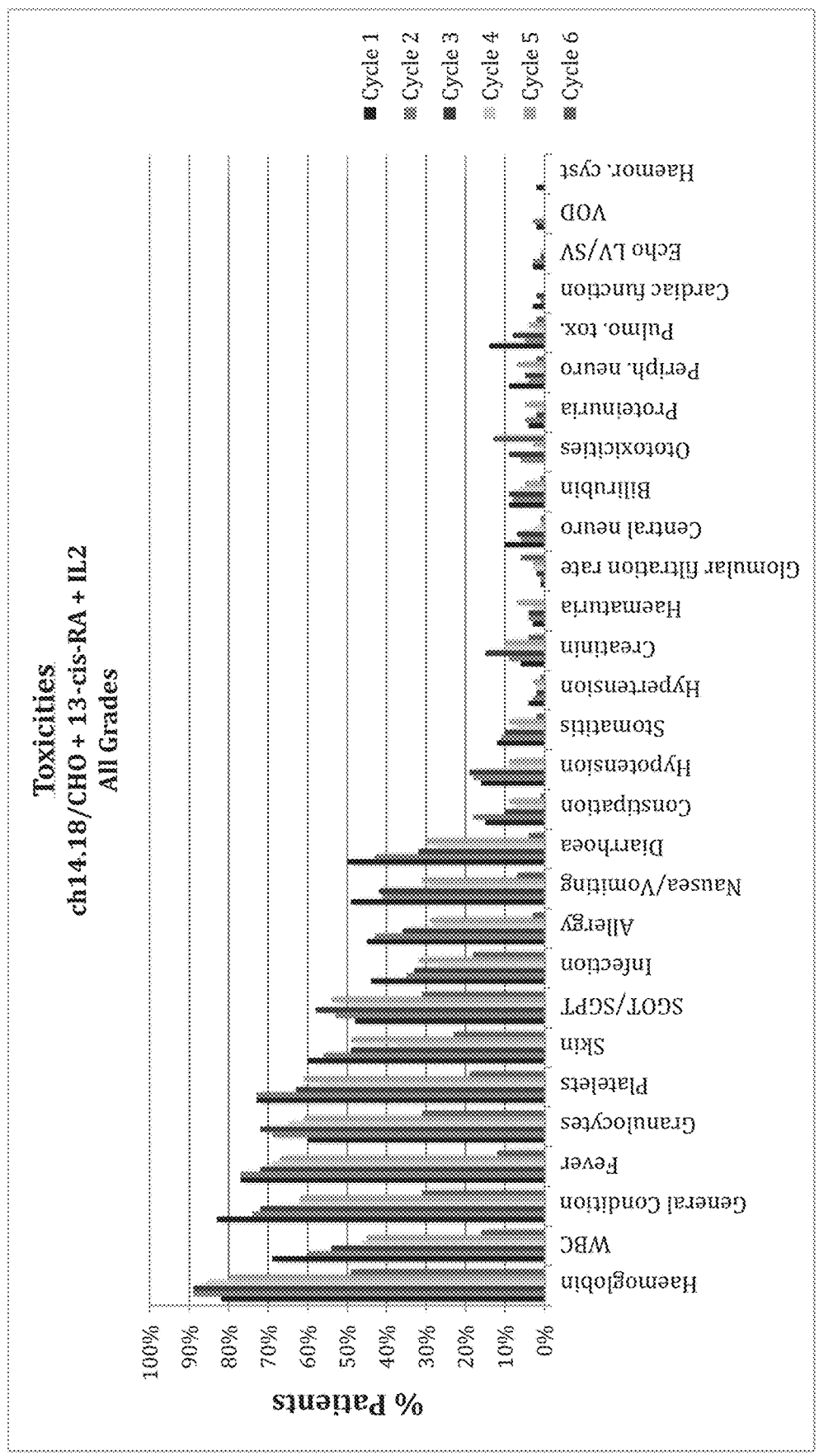
Figure 10:
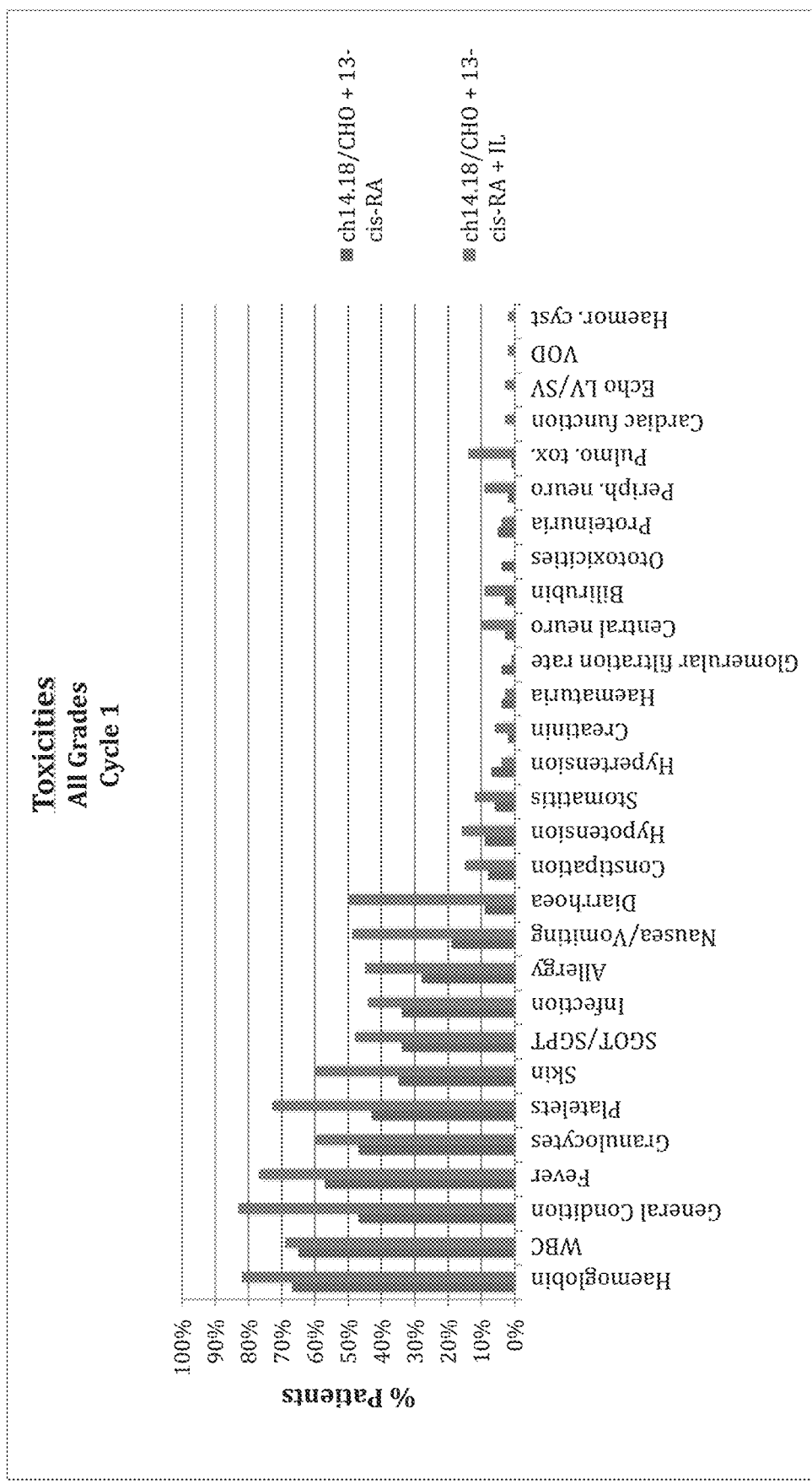
FIGS. 10 to 15 show charts of toxicities observed in the respective treatment cycle (FIG. 10: cycle 1, FIG. 11: cycle 2, FIG. 12: cycle 3, FIG. 13: cycle 4, FIG. 14: cycle 5, FIG. 15: cycle 6) in percent of total evaluated patients treated in the respective schedules with and without IL-2.
Figure 11:
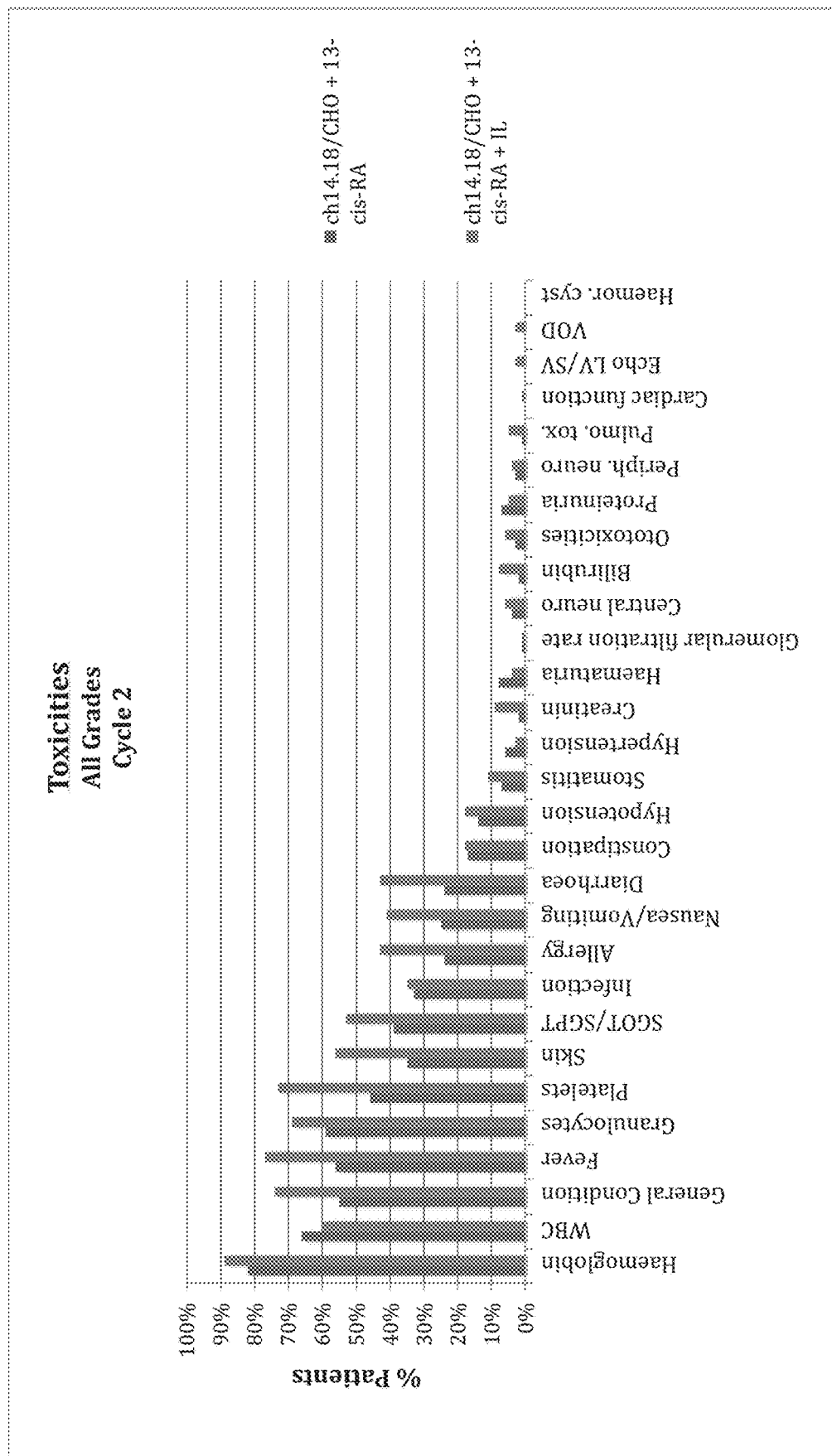
Figure 12:
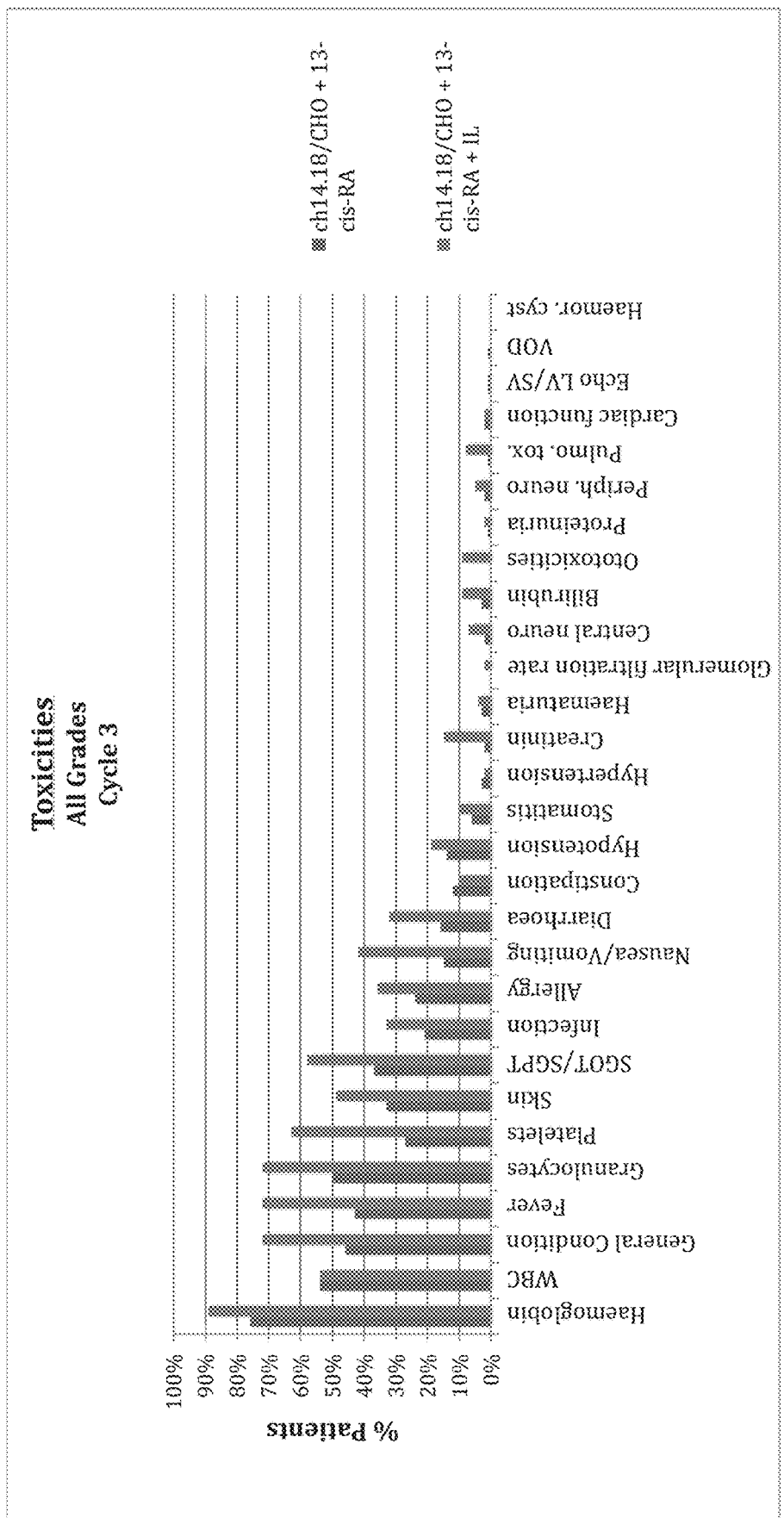
Figure 13:
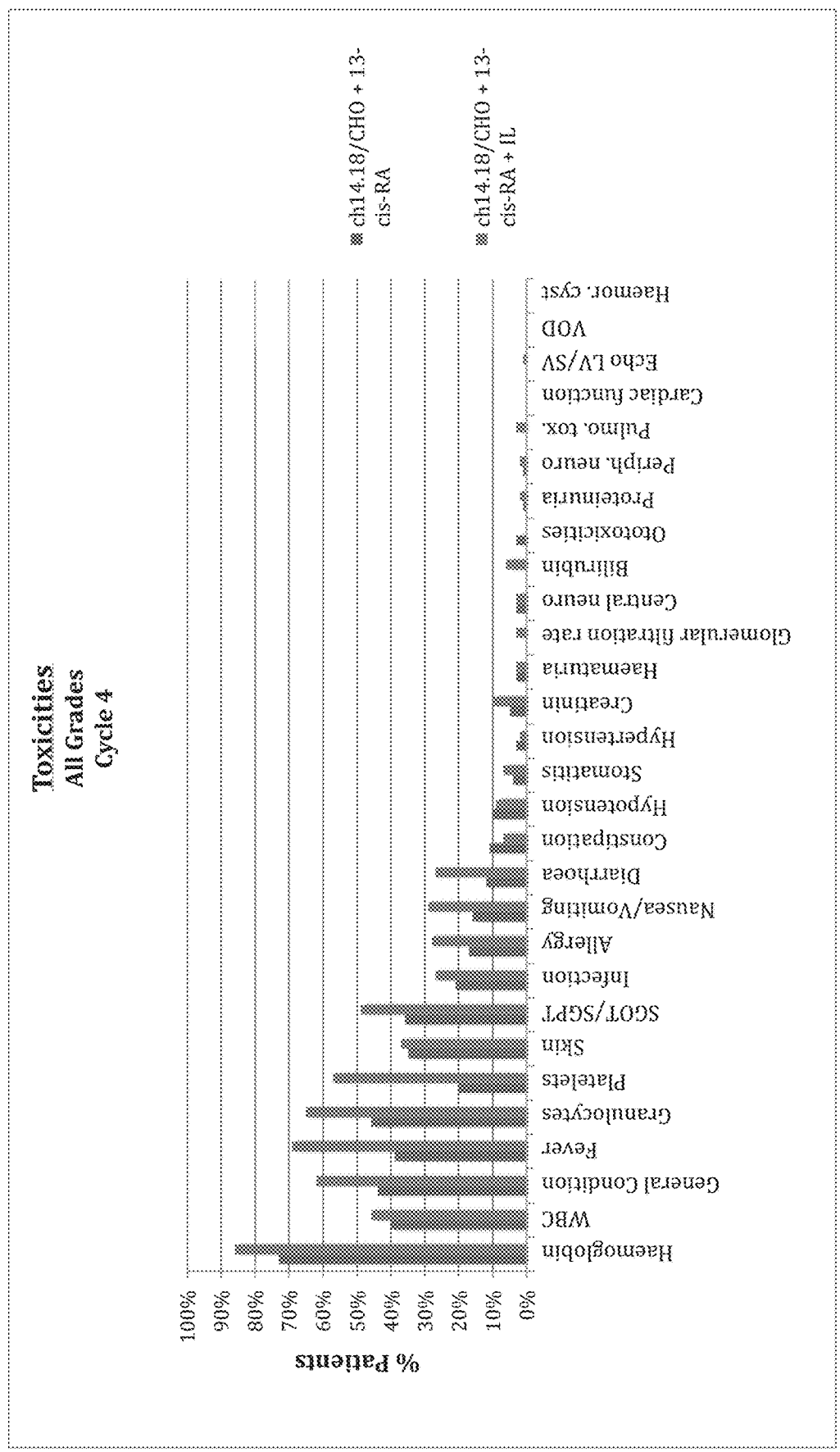
Figure 14:
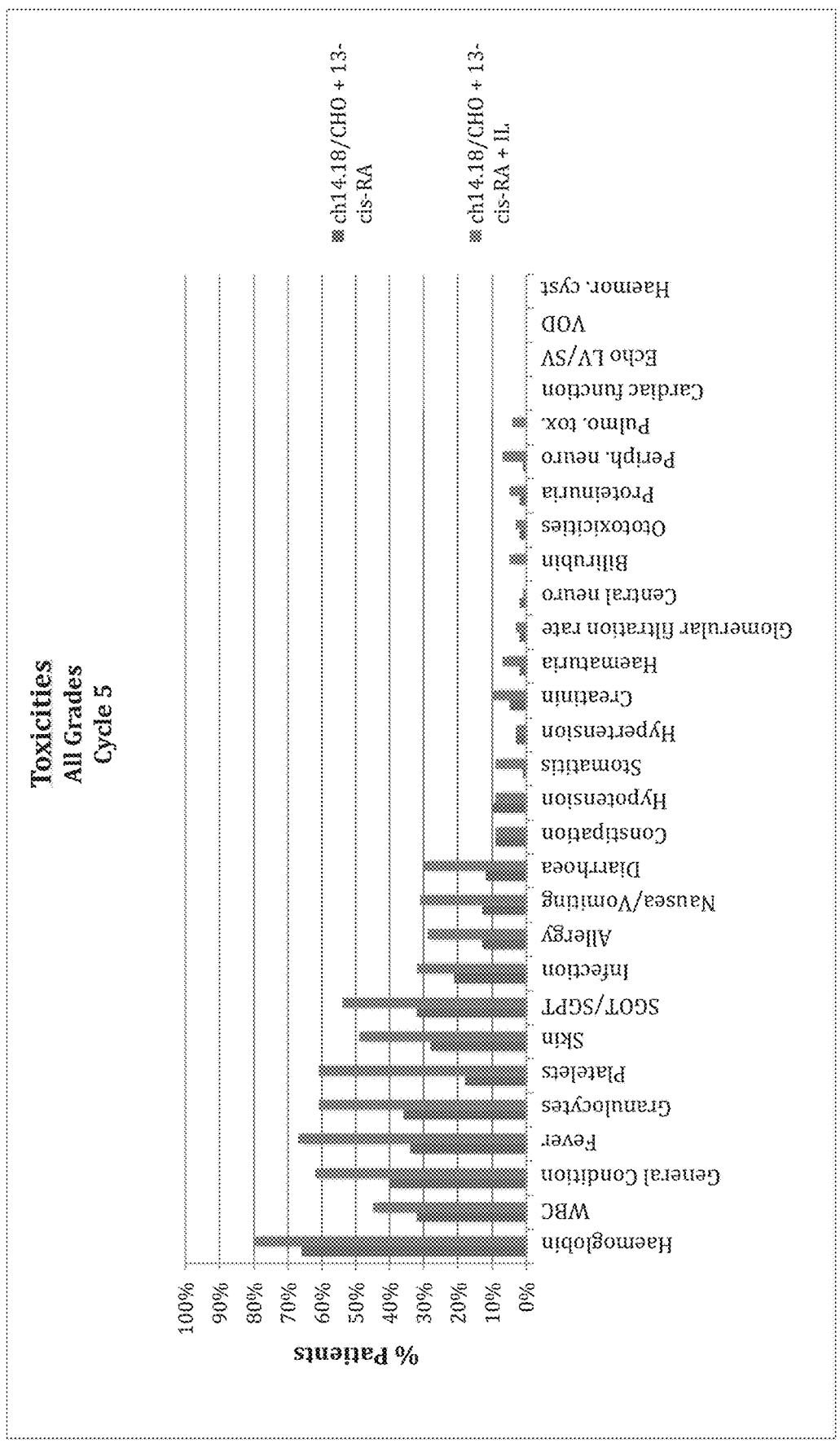
Figure 15:
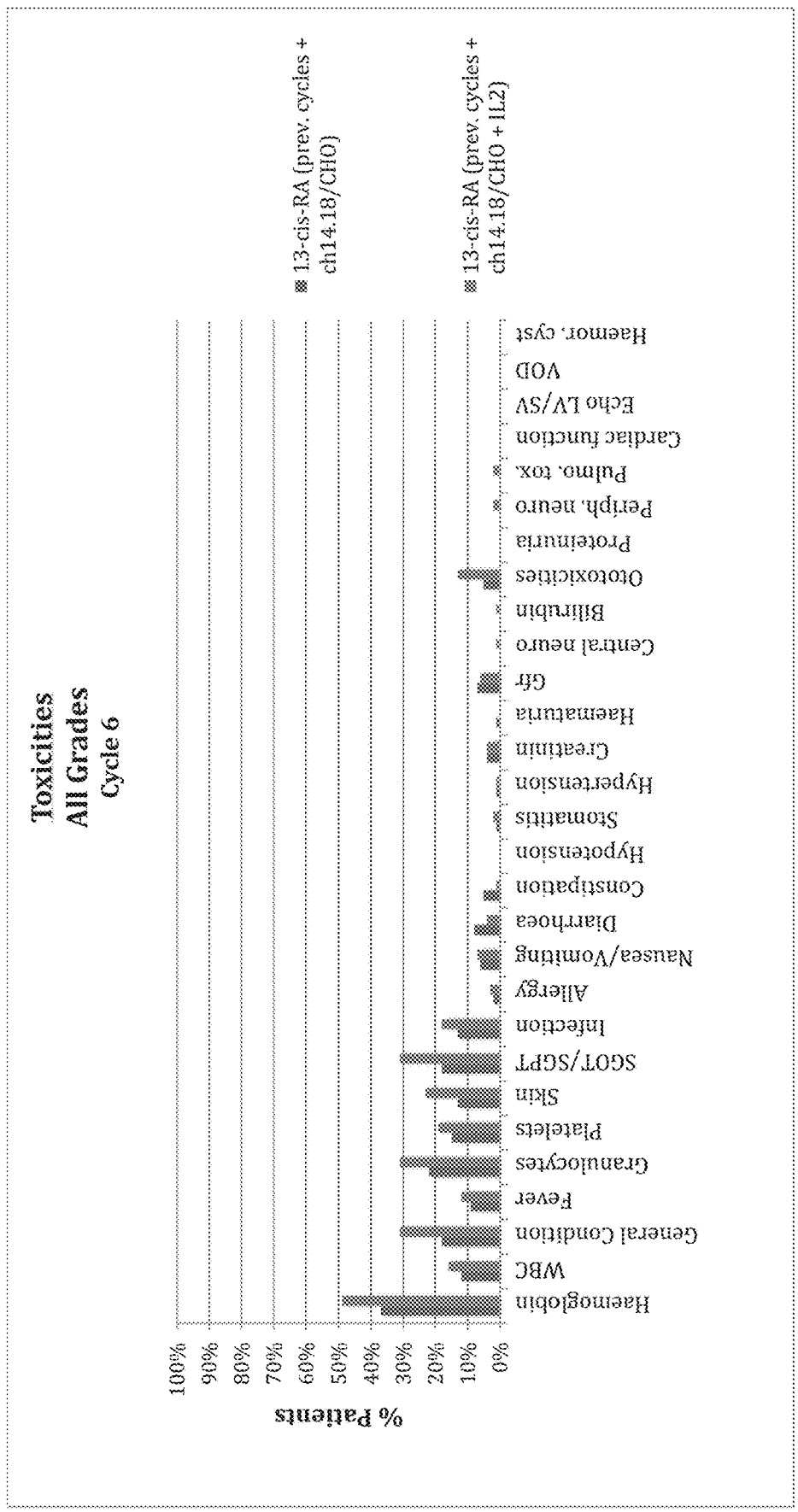

The results are also depicted in FIGS. 1, 2, and 3 (also in comparison to Yu et al.) and in FIGS. 4 to 15 (for further details about toxicities, i.e. adverse effects or side effects observed). According to these data, IL-2 does not contribute to the efficacy of anti-GD2 antibody treatment. However, concomitant IL-2 treatment substantially increases side effects and toxicities. APN311+cis-RA treatment of complete responders at start of immunotherapy leads to similar 2-year event-free and overall survival percentages and total survival curves than those found in the ch14.18/SP2-0+IL2+GM-CSF+cis-RA group of the NEJM 2010 study (Yu et al. 2010, cited above).

This suggests that the addition of both IL2 and GM-CSF are not needed to achieve the efficacy level of the combination treatment as described in NEJM 2010.

Both EFS and OS for APN311+cis-RA (complete responders at start of immunotherapy) compared to EFS and OS of patients of NEJM 2010 who received cis-RA only are improved (2y EFS: 70% versus 46%; 2y OS: 81% versus 75%; see also table 7). This indicates single agent efficacy of APN311.

In an overall assessment of risk and benefit, it is therefore concluded that APN311+cis-RA in complete responders at start of immunotherapy may be even superior to the 4-component immunotherapy as described in NEJM 2010, especially because of the substantially reduced side effect profile and reduced complexity of treatment due to omission of IL2 and GM-CSF, and because of the similar clinical efficacy in terms of EFS and OS.

Example 3: CDC and WBT Assay of a Neuroblastoma Patient Treated with Antibody A neuroblastoma patient has been treated with APN311 in a continuous infusion schedule, i.e. has received the antibody as a continuous infusion over 24 h per day for 10 consecutive days (on days 1-10 of a treatment cycle) in a dose of 10 mg/m$^2$/day for 6 subsequent cycles. Each treatment cycle comprised 35 days. During each treatment cycle and during the overall treatment time of said 6 subsequent cycles, the patient has only received antibody treatment and has not been treated with any cytokine nor retinoid.

Blood samples have been obtained from said patient at the indicated time points and have been analyzed in a CDC assay and WBT as described in Examples 4 and 5. The results are depicted in FIG. 16. FIG. 16 shows that antibody treatment without any cytokine treatment causes increased levels of tumor cell lysis. These levels of tumor cell lysis are comparable to the levels of patients treated with the antibody and IL-2 (one representative patient is shown in FIG. 17). The patient depicted in FIG. 17 has been treated with the same treatment schedule as the patient shown in FIG. 16, but has additionally been treated with s.c. IL-2 in a dose of 6×10$^6$ IU/m$^2$/day on days 1 to 5 and 8 to 12.

As can be seen especially in FIG. 16B, an increased level of target cell lysis in the whole blood test (WBT) is maintained even for time periods within the overall treatment time, where the patient is not treated with the preparation comprising an anti-GD2 antibody, i.e. in the intervals between the treatment periods with the preparation comprising an anti-GD2 antibody.

Example 4: CDC Assay Method

Principle for CDC (Complement Dependent Cytotoxicity)

Induction of tumor cell cytotoxicity of normal human serum or plasma in the presence of APN301 or APN311, or of patients' serum or plasma after infusion of one of these antibodies, to the GD2 antigen positive LAN-1 neuroblastoma cancer cell line (target cells) was determined in a $^{51}$Chromium release assay. The target cells were incubated with Na$_2$$^{51}$Cr(VI)O$_4$, which permeates the cell membrane and binds to cytoplasmatic proteins in the reduced Cr-III-valent form, thereby not leaking out anymore of an intact cell. When these cells are lysed after incubation with serum or plasma and antibodies or patients' serum or plasma, radioactivity is released into the supernatant dependent on the lytic capacity in the tested samples.

Spontaneous background lysis and total lysis (maximally achievable cell lysis or maximal possible target cell lysis) by a surfactant were determined in each individual experiment. After subtracting spontaneous lysis, the lysis induced by the tested samples was calculated as % of total lysis.

Serum or Plasma Sampling:

Whole blood from normal human donors or from patients was sampled using heparinized vacutainer vials for plasma or serum clotting vials for serum. Vials were centrifuged at 2000 g for 20 minutes. The supernatant plasma or serum could be used immediately for the assay or stored at −20° C. (no thawing and re-freezing allowed).

Labeling of Target Cells with $^{51}$Cr:

LAN-1 cells were cultivated in RPMI 1640 with 10% heat inactivated FCS. The day preceding the assay they were transferred into fresh flasks and fresh medium. The assay was carried out in a 96-well flat bottom cell culture plate, using 4×10$^4$ labeled cells per well with an activity of 800 nCi $^{51}$Cr per well. The needed amount of cells was harvested from the culture flasks, the suspension centrifuged and re-suspended in 1 ml of PBS def. with 0.1% EDTA and 1% FCS. The calculated volume of the $^{51}$Cr solution was added, cells were incubated for 90 minutes at 37° C. and 5% CO$_2$ under gentle rotation of the tube.

Then the cell suspension was washed twice with cell culture medium to remove radioactivity from outside the cells. This medium contained additionally 100 U/ml penicillin G and 100 µg/ml streptomycin sulphate. The pellet of labeled cells after the washing steps was resuspended to the wanted concentration of 4×10$^5$ cells per ml.

Assay Procedure:

For the assessment of cytolytic capacity of antibodies, the following was pipetted:
50 µl of the samples (antibody dilutions)
100 µl 1:4 pre-diluted normal human serum or plasma
100 µl $^{51}$Cr labeled cell suspension (4×10$^5$ per ml)

For the assessment of cytolytic capacity of patients' plasma or serum, the following was pipetted:
50 µl medium
100 µl 1:4 pre-diluted patients' plasma or serum
100 µl $^{51}$Cr labeled cell suspension (4×10$^5$ per mL)

Assay plates for CDC were incubated in a $CO_2$ incubator at 37° C., 5% $CO_2$, for 4 hours, or when compared directly to a WBT, for 20 hours.

In addition, an aliquot of each blood sample is preincubated with ganglidiomab, a monoclonal mouse anti-ch14.18 antibody (anti-idiotypic antibody), and further processed as described above. It binds specifically to the antibody present in the blood sample after administration of the antibody to the patient. Thereby, the anti-idiotypic antibody inhibits the ability of the antibody to lyse the tumor target cells in combination with blood cells (WBT) and/or plasma components (CDC). Residual lysis can be defined as a non-antibody mediated effect.

Then the supernatants of each well are harvested using harvesting frames with absorption cartridges and a harvesting press (skatron). These cartridges soaked with the cell supernatants are transferred into counting vials of the gamma counter. Radioactivity, which is proportional to the release of 51-chromium after a damage of the labeled target cells, is measured from all samples and expressed in counts per minute (cpm). Results are calculated as % lysis subtracting the cpms of spontaneous lysis from all sample values and relating to the cpm of the maximally achievable lysis with a surfactant which is 100%.

$$\frac{100 \times (\text{cpm sample minus cpm spontaneous lysis})}{\text{cpm maximal lysis minus spontaneous lysis}} = \% \text{ lysis of samples}$$

The above described CDC assay method has been used for the results as shown in FIG. 16 A.

Example 5: WBT Method

Principle for WBT (Whole Blood Test):

Induction of tumor cell cytotoxicity of normal human whole blood in the presence of APN301 or APN311, or of patients' whole blood after infusion of one of these antibodies, to the GD2 antigen positive LAN-1 neuroblastoma cancer cell line (target cells) was determined in a $^{51}$Chromium release assay.

The target cells were incubated with $Na_2^{51}Cr(VI)O_4$, which permeates the cell membrane and binds to cytoplasmatic proteins in the reduced Cr-III-valent form, thereby not leaking out of intact cells anymore. When these cells are lysed after incubation with whole blood and antibodies or patients' whole blood, radioactivity is released into the supernatant dependent on the lytic capacity in the tested samples.

Spontaneous background lysis and total lysis (maximally achievable lysis or maximal possible target cell lysis) by a surfactant were determined in each individual experiment. After subtracting spontaneous lysis, the lysis induced by the tested samples was calculated as % of total lysis.

Blood Sampling:

Whole blood from normal human donors or from patients was sampled using heparinized vacutainer vials.

Labeling of Target Cells with $^{51}$Cr:

LAN-1 cells were cultivated in RPMI 1640 with 10% heat inactivated FCS. The day preceding the assay they were transferred into fresh flasks and fresh medium. The assay was carried out in a 96-well flat bottom cell culture plate, using $4\times10^4$ labeled cells per well with an activity of 800 nCi $^{51}$Cr per well. The needed amount of cells was harvested from the culture flasks, the suspension centrifuged and re-suspended in 1 ml of PBS def. with 0.1% EDTA and 1% FCS. The calculated volume of the $^{51}$Cr solution was added, cells were incubated for 90 minutes at 37° C. and 5% $CO_2$ under gentle rotation of the tube.

Then the cell suspension was washed twice with cell culture medium to remove radioactivity from outside the cells. This medium contained additionally 100 U/ml penicillin G and 100 µg/ml streptomycin sulfate. The pellet of labeled cells after the washing steps was re-suspended to the wanted concentration of $4\times10^5$ cells per ml.

Assay Procedures:

For the assessment of cytolytic capacity of antibodies the following was pipetted:

50 µl of the samples (antibody dilutions)
100 µl 1:2 pre-diluted normal human whole blood
100 µl $^{51}$Cr labeled cell suspension ($4\times10^5$ per ml)

For the assessment of cytolytic capacity of patients' whole blood the following was pipetted:

50 µl medium
100 µl 1:2 pre-diluted patient's blood
100 µl $^{51}$Cr labeled cell suspension ($4\times10^5$ per ml)

Assay plates are incubated in a $CO_2$ incubator at 37° C., 5% $CO_2$, for 20 hours.

In addition, an aliquot of each blood sample is preincubated with ganglidiomab, a monoclonal mouse anti-ch14.18 antibody (anti-idiotypic antibody), and further processed as described above. It binds specifically to the antibody present in the blood sample after administration of the antibody to the patient. Thereby, the anti-idiotypic antibody inhibits the ability of the antibody to lyse the tumor target cells in combination with blood cells (WBT) and/or plasma components (CDC). Residual lysis can be defined as a non-antibody mediated effect.

Then the supernatants of each well are harvested using harvesting frames with absorption cartridges and a harvesting press (skatron). These cartridges soaked with the cell supernatants are transferred into counting vials of the gamma counter. Radioactivity which is proportional to the release of 51-chromium after a damage of the labelled target cells is measured from all samples and expressed in counts per minute (cpm). Results are calculated as % lysis subtracting the cpms of spontaneous lysis from all sample values and relating to the cpm of the maximally achievable lysis with a surfactant which is 100%.

100×(cpm sample minus cpm spontaneous lysis)=% lysis of samples cpm maximal lysis minus spontaneous lysis The above described WBT method has been used for the results as shown in FIG. 16 B.

The invention is further illustrated by the following embodiments, which can be readily combined with any one of the claims:

1. A preparation comprising an anti-GD2 antibody for use in the treatment of a GD2 positive cancer in a patient, wherein the preparation comprising an anti-GD2 antibody is administered to the patient without concomitantly administering IL-2, and wherein one or more treatment periods with the antibody is/are preceded, accompanied, and/or followed by one or more treatment periods with a retinoid.

2. A preparation comprising an anti-GD2 antibody for use in the treatment of a GD2 positive cancer in a patient, wherein the preparation comprising an anti-GD2 antibody is administered to the patient without concomitantly administering IL-2, and wherein one or more treatment periods with the antibody is/are preceded, accompanied, and/or followed by one or more treatment periods with a retinoid within the same treatment cycle.
3. A preparation comprising an anti-GD2 antibody for use in the treatment of a GD2 positive cancer in a patient, wherein the preparation comprising an anti-GD2 antibody is administered to the patient as a continuous infusion for one or more days, without concomitantly administering IL-2.
4. A preparation comprising an anti-GD2 antibody for use in the treatment of a GD2 positive cancer in a patient, wherein the preparation comprising an anti-GD2 antibody is administered to the patient as a continuous infusion for one or more days and for two or more treatment cycles, without concomitantly administering IL-2.
5. A preparation comprising a chimeric or humanized anti-GD2 antibody for use in the treatment of a GD2 positive cancer in a patient, wherein the preparation comprising an anti-GD2 antibody is administered to the patient as a continuous infusion for one or more days without concomitantly administering IL-2.
6. A preparation comprising an anti-GD2 antibody for use in the treatment of a GD2 positive cancer in a patient, wherein the preparation comprising an anti-GD2 antibody is administered to the patient as a continuous infusion without concomitantly administering IL-2, and wherein the anti-GD2 antibody is not a 14G2a antibody.
7. A method of treating a GD2 positive cancer in a patient comprising administering an anti-GD2 antibody to the patient without concomitantly administering IL-2, wherein a GD2 positive cancer is treated.
8. A method of treating a GD2 positive cancer by administering a preparation comprising an anti-GD2 antibody to a patient, wherein the patient is not concomitantly treated with IL-2, and wherein one or more treatment periods with the antibody is/are preceded, accompanied, and/or followed by one or more treatment periods with a retinoid.
9. A method of treating a GD2 positive cancer by administering a preparation comprising an anti-GD2 antibody to a patient, wherein the patient is not concomitantly treated with IL-2, and wherein one or more treatment periods with the antibody is/are preceded, accompanied, and/or followed by one or more treatment periods with a retinoid within the same treatment cycle.
10. A method of treating a GD2 positive cancer by administering a preparation comprising an anti-GD2 antibody to a patient, wherein the preparation comprising an anti-GD2 antibody is administered to the patient as a continuous infusion for one or more days without concomitantly administering IL-2.
11. A method of treating a GD2 positive cancer in a patient, wherein a preparation comprising an anti-GD2 antibody is administered to the patient as a continuous infusion for one or more days and for two or more treatment cycles, and wherein the patient is not concomitantly treated with IL-2.
12. A method of treating a GD2 positive cancer in a patient, wherein a preparation comprising a chimeric or humanized anti-GD2 antibody is administered to the patient as a continuous infusion for one or more days without concomitantly administering IL-2.
13. A method of treating a GD2 positive cancer in a patient, wherein the preparation comprising an anti-GD2 antibody is administered to the patient as a continuous infusion, wherein the patient is not concomitantly treated with IL-2, and wherein the anti-GD2 antibody is not a 14G2a antibody.
14. The preparation or method of any of the preceding embodiments, wherein the patient is not concomitantly treated with GM-CSF.
15. The preparation or method of one of the preceding embodiments, wherein the patient is not treated with a cytokine.
16. The preparation or method of one of the preceding embodiments, wherein the patient is not treated with said cytokine(s) within the same treatment cycle.
17. The preparation or method of one of the preceding embodiments, wherein the patient is not treated with said cytokine(s) within the same overall treatment time.
18. The preparation or method of one of the preceding embodiments, wherein the patient may have been treated with IL-2, GM-CSF, and/or one or more other cytokines in one or more previous treatment cycles and/or overall treatment times.
19. The preparation or method of one of the preceding embodiments, wherein the GD2 positive cancer is neuroblastoma, glioblastoma, medulloblastoma, astrocytoma, melanoma, small-cell lung cancer, desmoplastic small round cell tumor, osteosarcoma, rhabdomyosarcoma, and/or another soft tissue sarcoma.
20. The preparation or method of one of the preceding embodiments, wherein the GD2 positive cancer is neuroblastoma.
21. The preparation or method of one of the preceding embodiments, wherein the patient has been diagnosed with high risk neuroblastoma and/or stage 4 neuroblastoma.
22. The preparation or method of one of the preceding embodiments, wherein the patient has been diagnosed with minimal residual disease.
23. The preparation or method of one of the preceding embodiments, wherein the patient has been diagnosed with relapsed and/or refractory disease.
24. The preparation or method of one of the preceding embodiments, wherein the preparation comprising an anti-GD2 antibody is administered as a continuous intravenous infusion over 24 hours per day.
25. The preparation or method of one of the preceding embodiments, wherein the preparation comprising an anti-GD2 antibody is administered in a daily dose of 1 to 15, 1 to 20, 1 to 25, 1 to 30, 1 to 35, 1 to 50, or 1 to 60 mg/m$^2$.
26. The preparation or method of one of the preceding embodiments, wherein the preparation comprising an anti-GD2 antibody is administered in a daily dose of 1 to 30 mg/m$^2$, 1 to 35 mg/m$^2$, 1 to 50 mg/m$^2$, or 1 to 60 mg/m$^2$.
27. The preparation or method of one of the preceding embodiments, wherein the preparation comprising an anti-GD2 antibody is administered in a dose of 10, 20, 25, 50, 60, 65, 68, 70, 75, 80, 100, 120, 150, 200, 210, 250, or 300 mg/m$^2$/cycle.
28. The preparation or method of one of the preceding embodiments, wherein the preparation comprising an anti-GD2 antibody is administered by using a mini-pump.
29. The preparation or method of any of the preceding embodiments, wherein the anti-GD2 antibody is a 14.18 antibody.
30. The preparation or method of any of the preceding embodiments, wherein the anti-GD2 antibody is encoded by the amino acid sequence of SEQ ID No:3 and/or 4, or fragments or homologs thereof with the same or similar native qualitative activity.

31. The preparation or method of one of the preceding embodiments, wherein the anti-GD2 antibody is ch14.18/CHO or ch14.18/SP2/0.
32. The preparation or method of one of the preceding embodiments, wherein the preparation comprising the anti-GD2 antibody is APN311.
33. The preparation or method of one of the preceding embodiments, wherein the anti-GD2 antibody is dinutuximab.
34. The preparation or method of one of the preceding embodiments, wherein the preparation comprising an anti-GD2 antibody is administered in a dose of 7, 10, 15, 17.5, 20, or 25 mg/m$^2$/day.
35. The preparation or method of one of the preceding embodiments, wherein the preparation comprising an anti-GD2 antibody is administered for 4, 5, 10, 14, 15, or 21 consecutive days.
36. The preparation or method of one of the preceding embodiments, wherein the preparation comprising an anti-GD2 antibody is administered for 3, 4, 5, 6, 7, 8, or 9 or more treatment cycles.
37. The preparation or method of one of the preceding embodiments, wherein the preparation comprising an anti-GD2 antibody is APN311 and is administered in a dose of 10 mg/m$^2$/day for 10 consecutive days for 6 or more treatment cycles.
38. The preparation or method of one of the preceding embodiments, wherein the anti-GD2 antibody is ch14.18/SP2/0 and is administered in a dose of 25, 20, 17.5, or 15 mg/m$^2$/day for 4 consecutive days for 5 or more treatment cycles.
39. The preparation or method of one of the preceding embodiments, wherein the administration period of the preparation comprising an anti-GD2 antibody may be followed by an administration period of isotretinoin or another retinoid.
40. The preparation or method of one of the preceding embodiments, wherein the administration of the preparation comprising an anti-GD2 antibody is accompanied by the administration of morphine and/or one or more other analgesics.
41. The preparation or method of one of the preceding embodiments, wherein the administration of the preparation comprising an anti-GD2 antibody is accompanied by the administration of a reduced dose of morphine and/or one or more other analgesics.
42. The preparation or method of one of the preceding embodiments, wherein the administration of the preparation comprising an anti-GD2 antibody is not accompanied by the administration of morphine and/or one or more other analgesics.

The invention claimed is:

1. A method of treating a GD2 positive cancer in a patient comprising administering a preparation comprising an anti-GD2 antibody to the patient without concomitantly administering IL-2 within the same treatment cycle and/or within the same overall treatment period, wherein a GD2 positive cancer is treated in the patient, wherein the anti-GD2 antibody is a 14.18 antibody, and wherein the preparation is administered to the patient in a dose of 10 mg/m²/day for 10 consecutive days or in a dose of 15, 20, or 25 mg/m²/day for 4 consecutive days.

2. The method of claim 1, wherein the anti-GD2 antibody is a chimeric or humanized anti-GD2 antibody.

3. The method of claim 1, further comprising treating the patient one or more times with a retinoid within the same treatment cycle preceding, accompanying, and/or following the administration of the anti-GD2 antibody.

4. The method of claim 1, wherein the anti-GD2 antibody is ch14.18/CHO or ch14.18/SP2/0.

5. The method of claim 1, wherein the anti-GD2 antibody has the light chain amino acid sequence of amino acid residues 21 to 240 of SEQ ID NO:3 and the heavy chain amino acid sequence of amino acid residues 21 to 462 SEQ ID NO:4.

6. The method of claim 1, wherein the anti-GD2 antibody is administered to the patient in a dose of 50 to 150 mg/m²/cycle.

7. The method of claim 1, wherein the preparation is administered to the patient in a dose of 50, 60, 65, 68, 70, 75, 80, 100, 120, or 150 mg/m²/cycle.

8. The method of claim 1, wherein the anti-GD2 antibody is administered to the patient for two or more treatment cycles.

9. The method of claim 1, wherein the patient is not concomitantly treated with GM-CSF within the same treatment cycle and/or within the same overall treatment period.

10. The method of claim 1, wherein the patient is not concomitantly treated with a cytokine within the same treatment cycle and/or within the same overall treatment period.

11. The method of claim 1, wherein the GD2 positive cancer is neuroblastoma, glioblastoma, medulloblastoma, astrocytoma, melanoma, small-cell lung cancer, desmoplastic small round cell tumor, osteosarcoma, rhabdomyosarcoma, or another soft tissue sarcoma.

12. The method of claim 1, wherein the patient suffers from primary refractory or relapsed high-risk neuroblastoma, or from minimal residual disease in high-risk neuroblastoma.

13. The method of claim 1, wherein a morphine dose of the overall treatment time is lower than a morphine dose of the overall treatment time in an according administration schedule wherein the anti-GD2 antibody is administered to a patient in a dose of 1 to 25 mg/m$^2$/day and 50 to 150 mg/m$^2$/cycle as a continuous infusion for 24 hours per day concomitantly with IL-2, GM-CSF, and/or another cytokine.

14. The method of claim 1, wherein a dose of one or more analgesics is reduced within the overall treatment time, within a treatment cycle, during the antibody treatment period within a treatment cycle, from one antibody treatment day to the next antibody treatment day within a treatment cycle, and/or from one treatment cycle to the next.

\* \* \* \* \*